US008372808B2

(12) United States Patent
Messing et al.

(10) Patent No.: US 8,372,808 B2
(45) Date of Patent: Feb. 12, 2013

(54) SUPPRESSION OF GLIAL FIBRILLARY ACIDIC PROTEIN

(75) Inventors: Albee Messing, Madison, WI (US); Woosung Cho, Madison, WI (US); Jon Scott Thorson, Middleton, WI (US); Randal D. Goff, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 387 days.

(21) Appl. No.: 12/589,638

(22) Filed: Oct. 26, 2009

(65) Prior Publication Data

US 2010/0190705 A1 Jul. 29, 2010

Related U.S. Application Data

(60) Provisional application No. 61/110,356, filed on Oct. 31, 2008.

(51) Int. Cl.
*A61K 38/00* (2006.01)
*A61K 31/715* (2006.01)
*A61K 31/675* (2006.01)
*A61K 31/66* (2006.01)
*A61K 31/59* (2006.01)

(52) U.S. Cl. ............ 514/12.1; 514/61; 514/80; 514/118; 514/167; 514/182; 514/183; 514/217; 514/22.5; 514/256; 514/259.2

(58) Field of Classification Search .................. 514/12.1, 514/61, 80, 118, 167, 169, 182, 183, 217, 514/225.5
See application file for complete search history.

(56) References Cited

U.S. PATENT DOCUMENTS

| 4,912,096 | A * | 3/1990 | Sudilovsky ...................... 514/91 |
| 5,627,047 | A | 5/1997 | Brenner et al. |
| 6,403,816 | B1 * | 6/2002 | Jaggi et al. ...................... 552/510 |
| 6,569,842 | B2 * | 5/2003 | Pezzuto et al. ................. 514/169 |
| 2008/0025959 | A1 * | 1/2008 | Daneman et al. ............. 424/94.1 |
| 2010/0004262 | A1 * | 1/2010 | Wilding et al. ........... 514/253.07 |

OTHER PUBLICATIONS

Sakakihara et al. Brain & Development 1995; 17 291-3.*
Gorospe Neurology(2002) 58(10):1494-1500.*
Szymas et al. (Acta Neurochir (Wien) (1986) 83: 144-150 as applied to claims 1-4, 6, 9, 12-13 and 16-17 in view of Hwang et al. Acta Neuropathol. (Berl) 57:230-232.*
Hwang et al. Acta Neuropathol. (Berl) 57:230-232.*
Liu et al. Biochemica et Biophysica Acta 1723; 270-281, (2005).*
Rothenaiger et al AIDS (2007) 21;2271-2281.*
Fatemi et al Schizophrenia Research 69 (2004) 317-323).*
Zhang et al. (J. Huazhong University of Science and Tech. [Med Sci] 25(6);625-628 (2005).*
Bourekas et al. (AJR:179, Jul. 2002, 251-257).*
Annabi et al (Journal of Neurochemistry, 2005, 94, 906-916).*
Cheon et al. (RG 22(3) 2002; 461-475).*
Ahmed et al., "Colchicine Glycorandomization Influences Cytotoxicity and Mechanism of Action", J. Am. Chem. Soc., 2006, vol. 128, Issue 44, pp. 14224-14225.

Alexander et al., "Insulin Stimulates Glyceraldehyde-3-Phosphate Dehydrogenase Gene Expression Through Cis-Acting DNA Sequences", Proc. Natl. Acad. Sci. USA, 1998, vol. 85, pp. 5092-5096.
Balant-Gorgia et al., "Clinical Pharmacokinetics of Clomipramine", Clinical Pharmacokinetics, 1991, vol. 20, pp. 447-462.
Baldessarini, R. J., "Drug Therapy of Depression and Anxiety Disorders", Brunton et al., The Pharmacological Basis of Therapeutics, 11th ed., pp. 429-459, 2006, New York, McGraw-Hill.
Besnard et al., "Multiple Interacting Sites Regulate Astrocyte-Specific Transcription of the Human Gene for Glial Fibrillary Acidic Protein", The Journal of Biological Chemistry, Nov. 5, 1991, vol. 266, No. 28, pp. 18877-18883.
Brenner M., "Structure and Transcriptional Regulation of the GFAP Gene", Brain Pathology, 1994, vol. 4, pp. 245-257.
Brenner et al., "Mutations in GFAP, Encoding Glial Fibrillary Acidic Protein are Associated with Alexander Disease", Nature Genetics, Jan. 3, 2001, vol. 27, pp. 117-120.
Carlsson A., "Structural Specificity for Inhibition of [14C]-5 Hydroxytryptamine Uptake by Cerebral Slices", J. Pharm. Pharmacol., 1970, vol. 22, pp. 729-732.
Carlsson et al., "Effect of Antidepressant Drugs on the Depletion of Intraneuronal Brain 5-hydroxytryptamine Stores Caused by 4-methyl-ethyl-meta-tyramine", European Journal of Pharmacology, 1969, pp. 357-366.
Chen et al., "Reexpression of Glial Fibrillary Acidic Protein Rescues the Ability of Astrocytoma Cells to Form Processes in Response to Neurons", J. Cell Biol., 1994, vol. 127, No. 3, pp. 813-823.
Chiu et al., "Synthesis and Turnover of Cytoskeletal Proteins in Cultured Astrocytes", Journal of Neurochemistry, 1984, vol. 42, pp. 166-174.
Dearmond et al., "Turnover of Glial Filaments in Mouse Spinal Cord", Journal of Neurochemistry, 1986, vol. 47, pp. 1749-1753.
Eddleston et al., "Molecular Profile of Reactive Astrocytes—Implications for their Role in Neurologic Disease", 1993, Neuroscience, vol. 54, pp. 15-36.
Eng et al., "Astrocytes Cultured From Transgenic Mice Carrying the Added Human Glial Fibrillary Acidic Protein Gene Contain Rosenthal Fibers", J. Neurosci. Res., 1998, vol. 53, pp. 353-360.
Eng et al., "GFAP and Astrogliosis", Brain Pathology, 1994, vol. 4, pp. 229-237.
Eng et al., "Glial Fibrillary Acidic Protein: GFAP-Thirty-One Years (1969-2000)", Neurochemical Research, 2000, vol. 25, pp. 1439-1451.
Gauthier et al., "Glycosidation of Lupane-Type Triterpenoids as Potent in vitro Cytotoxic Agents", Bioorg Med Chem, 2006, vol. 14, Issue 19, pp. 6713-6725. Gomi et al., "Mice Devoid of the Glial Fibrillary Acidic Protein Develop Normally and are Susceptible to Scrapie Prions", Neuron, 1995, vol. 14, pp. 29-41.
Gorospe et al., Molecular Findings in Symptomatic and Pre-Symptomatic Alexander Disease Patients, Neurology, 2002, vol. 58, pp. 1494-1500.
Guthrie et al., "Alexander's Disease in a Neurologically Normal Child: A Case Report", Pediatric Radiology, 2003, vol. 33, pp. 47-49.
Hagemann et al., "Alexander Disease-Associated Glial Fibrillary Acidic Protein Mutations in Mice Induce Rosenthal Fiber Formation and a White Matter Stress Response", The Journal of Neuroscience, Oct. 25, 2006, vol. 26, No. 43, pp. 11162-11173.

(Continued)

*Primary Examiner* — Shirley V Gembeh
(74) *Attorney, Agent, or Firm* — Foley & Lardner LLP

(57) ABSTRACT

Provided herein are methods of decreasing glial fibrillary acidic protein (GFAP) levels in a cell. Such methods include administering an effective amount of a GFAP lowering compound to the cell. Also provided are compounds useful for the treatment of Alexander disease in subjects at risk of or diagnosed with Alexander disease and methods for the identification of such compounds.

17 Claims, 18 Drawing Sheets

OTHER PUBLICATIONS

Hagemann et al., "Gene Expression Analysis in Mice with Elevated Glial Fibrillary Acidic Protein and Rosenthal Fibers Reveals a Stress Response Followed by Glial Activation and Neuronal Dysfunction", Human Molecular Genetics, 2005, vol. 14, No. 16, pp. 2443-2458.

Heemskerk et al., "Teaching Old Drugs New Tricks", Trends in Neurosciences, 2002, vol. 25, pp. 494-496.

Hwang et al., "Inhibition of Glial Inflammatory Activation and Neurotoxicity by Tricyclic Antidepressants", Neuropharmacology, 2008, vol. 55, pp. 826-834.

Jankowsky et al., "Co-Expression of Multiple Transgenes in Mouse CNS: A Comparison of Strategies", Biomolecular Engineering, 2001, vol. 17, pp. 157-165.

Laping et al., "Glial Fibrillary Acidic Protein: Regulation by Hormones, Cytokines, and Growth Factors", Brain Pathology, 1994, vol. 4, pp. 259-275.

Li et al., "GFAP Mutations in Alexander Disease, Int. J. Dev. Neurosci., 2002, vol. 20, pp. 259-268.

Li et al., "GFAP Mutations in Infantile, Juvenile, and Adult Forms of Alexander Disease", Annals of Neurology, 2005, vol. 57, pp. 310-326.

Liedtke et al., "GFAP is Necessary for the Integrity of CNS White Matter Architecture and Long-Term Maintenance of Myelination, Neuron, 1996, vol. 17, pp. 607-615.

Liedtke et al., "Experimental Autoimmune Encephalomyelitis in Mice Lacking Glial Fibrillary Acidic Protein is Characterized by a More Severe Clinical Course and an Infiltrative Central Nervous System Lesion", American Journal of Pathology, Jan. 1998, vol. 152, No. 1, pp. 251-259.

McCall et al., "Targeted Deletion in Astrocyte Intermediate Filament (GFAP) Alters Neuronal Physiology", Proc. Natl. Acad. Sci. USA, Jun. 1996, vol. 93, pp. 6361-6366.

Meins et al., "Infantile Alexander Disease: A GFAP Mutation in Monozygotic Twins and Novel Mutations in Two Other Patients", Neuropediatrics, 2002, vol. 33, pp. 194-198.

Messing et al., "Fatal Encephalopathy with Astrocyte Inclusions in GFAP Transgenic Mice", American Journal of Pathology, Feb. 1998, vol. 152, No. 2, pp. 391-398.

Morrison et al., "Hormones and Growth Factors Include the Synthesis of Glial Fibrillary Acidic Protein in Rat Brain Astrocytes", Journal of Neuroscience Research, 1985, vol. 14, pp. 167-176.

Mucke et al., "Rapid Activation of Astrocyte-Specific Expression of GFAP-lacZ Transgene by Focal Injury", The New Biologist, 1991, vol. 3, pp. 465-474.

Okamoto et al., "Autosomal Dominant Palatal Myoclonus and Spinal Cord Atrophy, J. Neurol. Sci., 2002, vol. 195, pp. 71-76.

Overbeek et al., "Coinfection Strategy for Visual Identification of Transgenic Mice", Transgenic Res., 1991, vol. 1, pp. 31-37.

Pekny et al., "Astrocyte Activation and Reactive Gliosis", Glia, 2005, vol. 50, pp. 427-434.

Pekny et al., "Mice Lacking Glial Fibrillary Acidic Protein Display Astrocytes Devoid of Intermediate Filaments but Develop and Reproduce Normally", The EMBO Journal, 1995, vol. 14, No. 9, pp. 1590-1598.

Probst et al., "Atypical Focal MRI Lesions in a Case of Juvenile Alexander's Disease, Ann. Neurol., 2003, vol. 53, pp. 118-120.

Quinlan et al., "GFAP and Its Role in Alexander Disease", Exp Cell Res., Jun. 10, 2007, vol. 313, No. 10, pp. 2077-2087 (NIH Public Access, Author Manuscript, pp. 1-19).

Reichelt et al., "Formation of a Normal Epidermis Supported by Increased Stability of Keratins 5 and 14 in Keratin 10 Null Mice", Molecular Biology of the Cell, Jun. 2001, vol. 12, pp. 1557-1568.

Reilly et al., "Regulation of Astrocyte GFAP Expression by TGF-β1 and FGF-2", Glia, 1998, vol. 22, pp. 202-210.

Ross et al., "Inhibition of the Uptake of Noradrenaline and 5-Hydroxytryptamine by Chlorphentermine and Chlorimipramine", European Journal of Pharmacology, 1972, vol. 17, pp. 107-112.

Rothstein et al., "β-Lactam Antibiotics Offer Neuroprotection by Increasing Glutamate Transporter Expression", Nature, Jan. 6, 2005, vol. 433, pp. 73-77.

Rothstein et al., "Neuroprotective Strategies in a Model of Chronic Glutamate-Mediated Motor Neuron Toxicity", J. Neurochem., 1995, vol. 65, pp. 643-651.

Rozovsky et al., Transcriptional Regulation of Glial Fibrillary Acidic Protein by Corticosterone in Rat Astrocytes in Vitro Is Influenced 1995, Endocrinology, 136: 2066-2073.

Rutka et al., "Transfection of Human Astrocytoma Cells with Glial Fibrillary Acidic Protein Complementary DNA: Analysis of Expression, Proliferation, and Tumorigenicity", Cancer Research, Aug. 1, 1993, vol. 53, pp. 3624-3631.

Sawaishi et al., "Juvenile Alexander Disease with a Novel Mutation in Glial Fibrillary Acidic Protein", Neurology, 2002, vol. 58, pp. 1539-1543.

Wakabayashi et al., "Nonlethal Detection of Transgene Expression in the CNS of Founder Mice," Bio Techniques, 1999, vol. 26, pp. 302-307.

Walz, W., "Acetylcholine and Serotonin Receptor Activation", Kettenmann et al., Neuroglia, 1995, New York, Oxford University Press, pp. 346-353.

Wille et al., "Relevant Issues in the Monitoring and the Toxicology of Antidepressants", Crit. Rev. Clin. Lab. Sci., 2008, vol. 45, pp. 25-89.

Zhuo et al., "Live Astrocytes Visualized by Green Fluorescent Protein in Transgenic Mice", Dev. Biol., 1997, vol. 187, pp. 36-42.

* cited by examiner

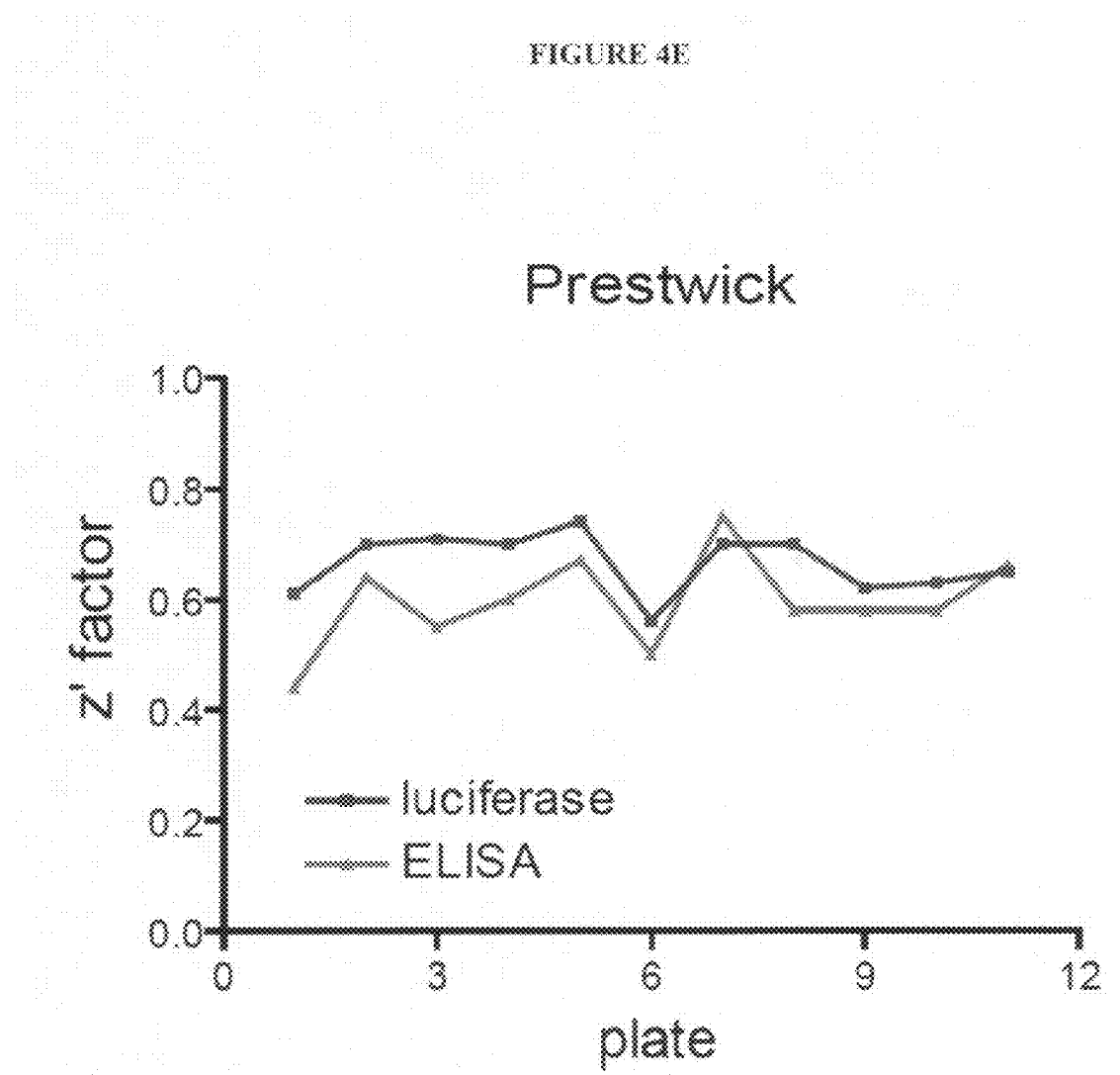

FIGURE 6
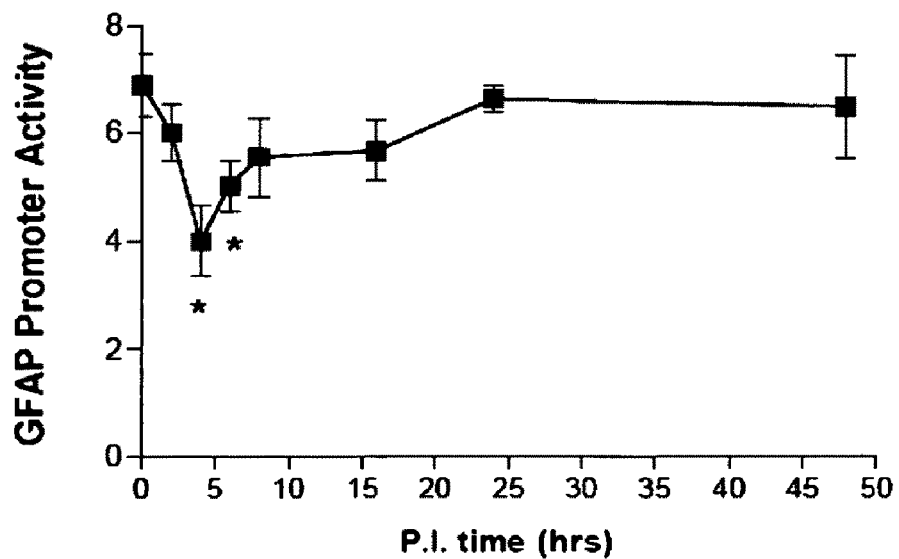
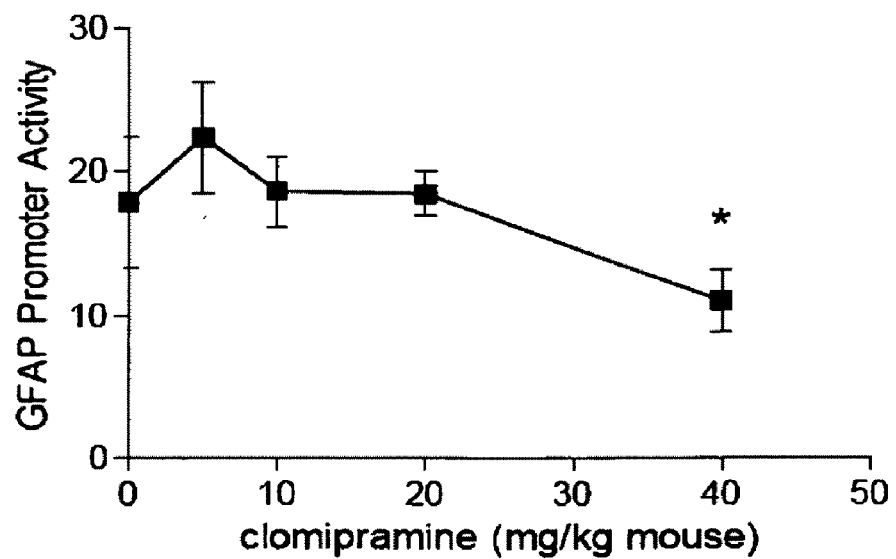

SUPPRESSION OF GLIAL FIBRILLARY ACIDIC PROTEIN

CROSS-REFERENCE TO RELATED PATENT APPLICATIONS

This application claims the benefit of U.S. Application No. 61/110,356 filed Oct. 31, 2008, which is incorporated herein by reference in its entirety.

GOVERNMENT SUPPORT

This invention was made with government support under HD046599 and NS060120 awarded by the National Institutes of Health. The government has certain rights in the invention.

BACKGROUND

Alexander disease is an uncommon but fatal central nervous system (CNS) disorder. Alexander disease usually affects children. In the most common form, Alexander disease begins its manifestations before the age of 2 years as megalencephaly and white matter loss, especially in the frontal lobes. Seizures and spasticity that are difficult to control are prominent symptoms, as are hydrocephalus and psychomotor developmental delay. The prognosis for individuals with Alexander disease is generally poor. Most children with the infantile form do not survive past the age of 6. In the juvenile form, death usually occurs within 10 years after the onset of symptoms.

The key diagnostic feature of the neuropathology in Alexander disease is widespread deposition of Rosenthal fibers in subpial, periventricular, and white matter astrocytes throughout the CNS. Morphologically, Rosenthal fibers consist of two components, bundles of intermediate filaments and surrounding irregular deposits of dense material. Biochemically, Rosenthal fibers are composed of a complex ubiquitinated mixture of the intermediate filament glial fibrillary acidic protein (GFAP) in association with other constituents, especially the small stress proteins αB-crystallin and HSP25. Rosenthal fibers are also found sporadically in several other settings, such as some astrocytomas and chronic gliosis; their original description was in a young adult with syringomyelia, but never to the extent seen in Alexander disease.

GFAP is the major structural protein in astrocytes, and the initiation of GFAP synthesis as astrocytes mature has traditionally been considered a key step in their differentiation. Studies in cultured astrocytes and cell lines of forced overexpression of GFAP or its antisense inhibition suggest that GFAP directly controls process outgrowth. Recent studies have also documented expression of GFAP at low levels in a multipotential stem cell that gives rise to both neurons and glia, as do later-forming radial glia. The transcriptional regulation of GFAP has been reviewed, and there are also several minor isoforms about which much less is known than the major GFAPa species of mRNA. One such isoform, termed GFAPE, arises by alternative splicing and produces a protein that interacts with presenilins in the brain, although the precise cell in which GFAPE is expressed is not yet clear. Other GFAP isoforms are expressed at low levels in several cells outside of the central nervous system, such as non-myelinating Schwann cells, enteric glia, lens epithelium, and hepatic stellate cells, but at much lower levels than the GFAPα in mature astrocytes. Given the breadth of cell types that express some form of GFAP, the consequences of GFAP-deficiency or deletion cannot easily be predicted.

In 1995-1996, generation of GFAP-null mice was reported by four different research groups. The consistent result was the surprising finding that GFAP-null mice are viable, with seemingly normal life spans, reproduction, and gross motor behavior. Ultrastructural studies in optic nerve and spinal cord suggested minor changes in astrocyte morphology, with shortening and thinning of astrocyte processes; this was supported with subsequent studies of dye-filled cells. With regard to neuronal function, subtle changes were identified in long-term depression in the cerebellum, and long-term potentiation in the hippocampus. There is some evidence for alterations in the blood brain barrier derived from cell culture models, and to a limited extent from studies in vivo. No defects have been found in any of the non-astrocytic cells that express minor GFAP isoforms.

The GFAP gene has been evaluated in at least 130 Alexander disease patients. Mutations are present in nearly all (~95%) cases of infantile Alexander disease, and at least a certain proportion of juvenile and adult cases. Remarkably, mutations at only two amino acids, Arg79 or Arg239, account for nearly half of all cases. All of the mutations are heterozygous, presumably acting in an autosomal dominant fashion. For all of the cases where parents were available for testing, the parents were normal (i.e. did not have the mutation present in their child), confirming that the mutations occurred de novo. Examples of GFAP mutations being inherited occurred in families of adult-onset cases, one being where a mother and two adult children were affected and carried the same mutation. The penetrance also approaches 100%, two exceptions being two children whose initial evaluation for other problems led to MRI diagnoses of leukodystrophy, with subsequent genetic analysis revealing GFAP mutations, and one of these children is now showing signs of Alexander Disease.

Many of the GFAP mutations occur within an amino acid sequence that is highly conserved among intermediate filament proteins. Mutations at the homologous sites of other intermediate filament proteins are also associated with human diseases involving blistering of the skin, cataracts, cardiomyopathies, and muscular dystrophies. Although homologous sites are affected, most of these other mutations lead to a dominant loss of function. GFAP mutations, on the other hand, appear to produce a dominant gain of function. For example, a loss of function is indicated for keratin mutations because both heterozygous mutations in humans and null mutations of the homologous gene in mice disrupt the keratin filament network and produce a similar blistering disease. In contrast, GFAP filaments are present in Alexander disease patients, and GFAP null mice are fully viable and their pathology does not resemble Alexander disease. Thus the GFAP mutations do not appear to act by reducing or eliminating normal GFAP function, but rather by producing a new, deleterious, activity.

Two studies have attempted to link GFAP deficiency with abnormalities of myelination. One of these reported that approximately half of the GFAP-null mice in their colony developed an adult onset degeneration of myelin, with resulting hydrocephalus. Grossly visible changes in cerebral white matter did not become apparent until mice were 18 months and older. The mechanism of this myelin degeneration has not been determined, and the possible contribution of background genetics (for instance, corpus callosum defects in 129 strain mice) has not been excluded. Furthermore, this finding has not been confirmed by any of the other groups working on GFAP-null mice. The second report determined that GFAP-null mice had increased susceptibility to experimental allergic encephalitis, with increased clinical scores and pathology.

However, inflammation is thought to play little role in the pathogenesis of Alexander disease.

Overall, the relevance of GFAP-null mice to Alexander disease remains uncertain. Such mice do not develop a severe leukodystrophy and have no Rosenthal fibers, two primary characteristics of the human disease. In addition, the GFAP-null mice do not exhibit developmental delay, spasticity, seizures, ataxia, or paralysis. It remains formally possible that some aspects of the Alexander phenotype reflect dominant negative effects, and studies with keratin 10 have shown that dominant negatives may sometimes produce more severe phenotypes than corresponding null mutations. However, for GFAP, most evidence suggests that a toxic gain of function may be implicated as the mechanism of action.

SUMMARY

Provided herein are methods of decreasing glial fibrillary acidic protein (GFAP) levels in a cell. The methods include administering an effective amount of GFAP lowering compound to the cell. The GFAP lowering compound may exhibit a cell-based GFAP protein level reduction of at least about 5% and/or may exhibit an hGFAP promoter luciferase reduction of at least about 10%. The GFAP lowering compound desirably exhibits a relatively low level of cell toxicity (in comparison to the dose levels required to suppress glial fibrillary acidic protein (GFAP) levels) and in certain embodiments may exhibit an MTDcc of at least about 10 µM. In some embodiments, the GFAP lowering compound may include a c-pendant amino tricyclic compound; a quinone compound; a triterpene derivative; and/or a polyphenol compound.

One embodiment provides a method to decrease the expression and/or protein level of a glial fibrillary acidic protein (GFAP) in a cell, which include administering to the cell a compound capable of downregulating the expression of a glial fibrillary acidic protein (GFAP) and/or decreasing the GFAP protein level. The compound may be antidepressant, antipsychotic, serotonin inhibitor or antihistamine. For example, the compound may be a tricyclic antidepressant, such as amitriptyline or clomipramine. The compound may be selected from the group consisting of diaziquone, clomipramine, chrysophanol, amitriptyline, tamoxifen, amlodipine, embelin, thioridazine, ritanserin, ketotifen, kanamycin, 4-acetamidophenyl salicylate, and/or terfenadine. In another embodiment, the compound may be a tricyclic compound having a pendant aminoalkyene or aminoalkenyene group (in which an oxygen or sulfer atom may be substituted for carbon atoms) connected to the central ring, such as amitriptyline, clomipramine, chlorprothixene and thioridazine. In the practice of the methods, the expression of the GFAP may decrease by at least 10% in comparison to the expression of the GFAP in a similar untreated cell. The cell may be in a subject.

Administering the compound may result in the amelioration of clinical symptoms associated with Alexander disease and/or may decrease: (i) the intensity of megalencephaly that is associated with Alexander disease, (ii) the amount of Rosenthal fibers, (iii) the intensity or frequency of seizures, or (iv) two or more of the above.

Provided are methods for treating Alexander disease. The methods include administering to a subject at risk of or with Alexander disease a therapeutically effective amount of a compound capable of downregulating the expression of a glial fibrillary acidic protein (GFAP) and/or decreasing the GFAP protein levels. The compound may be identified from a group of compounds that are already approved for human use by the FDA. The compound may be antidepressant, antipsychotic, serotonin inhibitor or antihistamine. The compound may be a tricyclic antidepressant such as amitriptyline, butriptyline, amoxapine, clomipramine, desipramine, dosulepin hydrochloride, doxepin, imipramine, dibenzepin, iprindole, lofepramine, nortriptyline, opipramol, protriptyline, and trimipramine. Alternatively, the compound may be selected from the group consisting of diaziquone, clomipramine, chrysophanol, amitriptyline, tamoxifen, amlodipine, embelin, thioridazine, ritanserin, ketotifen, kanamycin, 4-acetamidophenyl salicylate, and terfenadine.

Provided are methods of decreasing the intensity of megalencephaly in a patient with Alexander disease, comprising administering to the patient a therapeutically effective amount of a compound that suppresses or prevents the formation of glial fibrillary acidic protein (GFAP).

Provided are methods of decreasing the amount of Rosenthal fibers in a patient with Alexander disease, comprising administering to the patient a therapeutically effective amount of a compound that suppresses or prevents the formation of glial fibrillary acidic protein (GFAP).

Also provided herein are methods of decreasing glial fibrillary acidic protein (GFAP) in a cell, which include administering a therapeutically effective amount of GFAP lowering compound to the cell. In some embodiments, the cell is in a subject. In some embodiments, the subject is a human and the cell is a human cell.

Also provided herein are methods for decreasing the amount of GFAP in a human subject, which include administering a therapeutically effective amount of a GFAP lowering compound to the human subject.

In some embodiments, a GFAP lowering compound is administered to a subject who has been diagnosed with gliosis, and/or who is at risk or who has been diagnosed with Alexander disease. In some embodiments, administration of a GFAP lowering compound to a subject decreases one or more symptoms, such as the intensity of megalencephaly associated with Alexander disease, the amount of Rosenthal fibers, the frequency of seizures, and the intensity of seizures.

In some embodiments, suitable examples of GFAP lowering compounds include c-pendant amino tricyclic compounds, quinine compounds, triterpene derivatives and polyphenol compounds. By way of example, but not by way of limitation, in some embodiment the GFAP lowering compound comprises clomipramine. In other embodiments, the GFAP lowering compound comprises betulinic acid and/or a betulinic acid derivative.

In some embodiments, the GFAP lowering compound exhibits an hGFAP promoter luciferase reduction activity of at least about 10%. In other embodiments the GFAP lowering compound exhibits an hGFAP promoter luciferase reduction activity of at least about 20%, at least about 30%, at least about 35%, at least about 40%, at least about 50% or at least about 60%. In some embodiments the GFAP lowering compound exhibits an hGFAP promoter luciferase reduction activity of at least about 70%, or at least about 80%.

In some embodiments, the GFAP lowering compound exhibits a cell-based GFAP protein level reduction of at least about 5% or of at least about 6%. In other embodiments, the GFAP lowering compound exhibits a cell-based GFAP protein level reduction of at least about 8%, at least about 9%, at least about 10%, at least about 11%, at least about 12%, at least about 15%, at least about 18%, at least about 20%, or at least about 21%.

In other embodiments, the GFAP lowering compound exhibits a MTDcc of at least about 10 µM. In other embodiments, the GFAP lowering compound exhibits a MTDcc of at least about 7 µM, at least about 5 µM, or at least about 2.5 µM.

In further embodiments, the GFAP lowering compound exhibits a MTDcc of at least about 15 µM or at least about 20 µM.

In some embodiments, the GFAP lowering compound exhibits a desired hGFAP promoter luciferase reduction activity in conjunction with a desired cell-based GFAP protein level reduction and/or a desired MTDcc. For example, in some embodiments, the GFAP lowering compound has an MTDcc of greater than 15 µM and hGFAP promoter luciferase reduction activity of about 15%. In other embodiments, the GFAP lowering compound exhibits a cell-based GFAP protein level of greater than about 5% and a MTDcc of at least about 10 µM.

In some embodiments, the GFAP lowering compound includes one or more of diaziquone, clomipramine, chrysophanol, amitriptyline, chlorprothixene, EGCDG, tamoxifen, mundoserone, amlodipine, embelin, thioridazine, ritanserin, irigenol, fluccinonide, hexetidine, estradiol benzoate, ketotifen, clobetasol propionate, colecalciferol, fluphenazine, pyrogallin and kanamycin.

In other embodiments, the GFAP lowering compound includes one or more of diaziquone, clomipramine, chrysophanol, amitriptyline, tamoxifen, amlodipine, embelin, thioridazine, ritanserin, ketotifen, kanamycin, 4-acetamidophenyl salicylate, and terfenadine.

In further embodiments, the GFAP lowering compound includes one or more of diaziquone, clomipramine, chrysophanol, amitriptyline, chlorprothixene, EGCDG, mundoserone, amlodipine, ritanserin, irigenol, fluccinonide, hexetidine, estradiol benzoate, ketotifin, clobetasol propionate, colecalciferol, pyrogallin, kanamycin, azinphos methyl, 4-acetamidophenyl salicylate, oxotremorine, ritodrine, NPPB, chloramphenicol, phosphocreatine, betulinic acid, methylnorlichexanthone, and coumophos.

BRIEF DESCRIPTION OF THE DRAWINGS

FIGS. 4A-F show the results of a primary screening of 2880 bioactive molecules to identify suppressors of GFAP expression. FIGS. 4A and 4B show Scatter plots of response to compounds in the Prestwick and Spectrum libraries, presented as percent reduction in luciferase signal from GFAP-luciferase transgenic astrocytes after exposure to compounds at 10 µM for 48 hours. FIG. 4C shows a sample plate from the primary screen using a luciferase assay, with activity levels illustrated by Heat Map. Cells treated with compounds (columns 2-11) were compared to untreated cells (columns 1 and 12). Green represents maximal reduction, and red represents maximal activation, compared to control luciferase activity. FIG. 4D show a sample plate from the primary screen using cell-based ELISA, imaged using a Storm 860 phosphoimager. Cells treated with compounds (columns 2-11) were compared to untreated cells (column 12). Background was assessed in wells containing medium only (column 1). FIGS. 4E and 4F show the Z'-factor for each 96-well plate used in primary screening for both luciferase and cell-based ELISA assays. Eighty compounds were tested per plate. Plate numbers were arbitrary. The average Z'-factor for all luciferase plates in the Prestwick screen was 0.67, and in the Spectrum screen was 0.61. The average Z-factor for all cell-based ELISA plates in the Prestwick screen was 0.6, and in the Spectrum screen was 0.67.

FIG. 6A-B show the acute effects of clomipramine on GFAP promoter activity in vivo. FIG. 6A shows data from Tg172-9 mice (males, 3-4 month old) that were injected with clomipramine using a dose of 40 mg/kg, IP. Controls were injected with vehicle only. Brains were collected at various times post-injection, and analyzed for GFAP promoter activity using the Dual-Glo assay. Graphs present the mean±SEM (n=4 at each data point). Statistical significance was evaluated by unpaired t-test (* p<0.05). FIG. 6B shows data from Tg172-9 mice (females, 3-4 month old) that were injected with various doses of clomipramine, IP (5, 10, 20, or 40 mg/kg). Brains were collected at 6 hours post-injection and analyzed for GFAP promoter activity using the Dual-Glo assay. Graphs present the mean±SD (n=4 at each data point). Statistical significance was evaluated by unpaired t-test (* p<0.05).

FIG. 7A is a bar graph showing hGFAP promoter activity of clomipramine-treated mice. The mice show a 26% reduction in hGFAP promoter activity compared to vehicle-treated controls. FIG. 7B is a bar graph showing the GFAP protein levels of clomipramine-treated mice. The mice show a 57% reduction in total GFAP content compared to vehicle-treated controls. Graphs present the mean±SD (* p<0.05, ***p<0.001, unpaired t-test).

DETAILED DESCRIPTION

Figure 1:
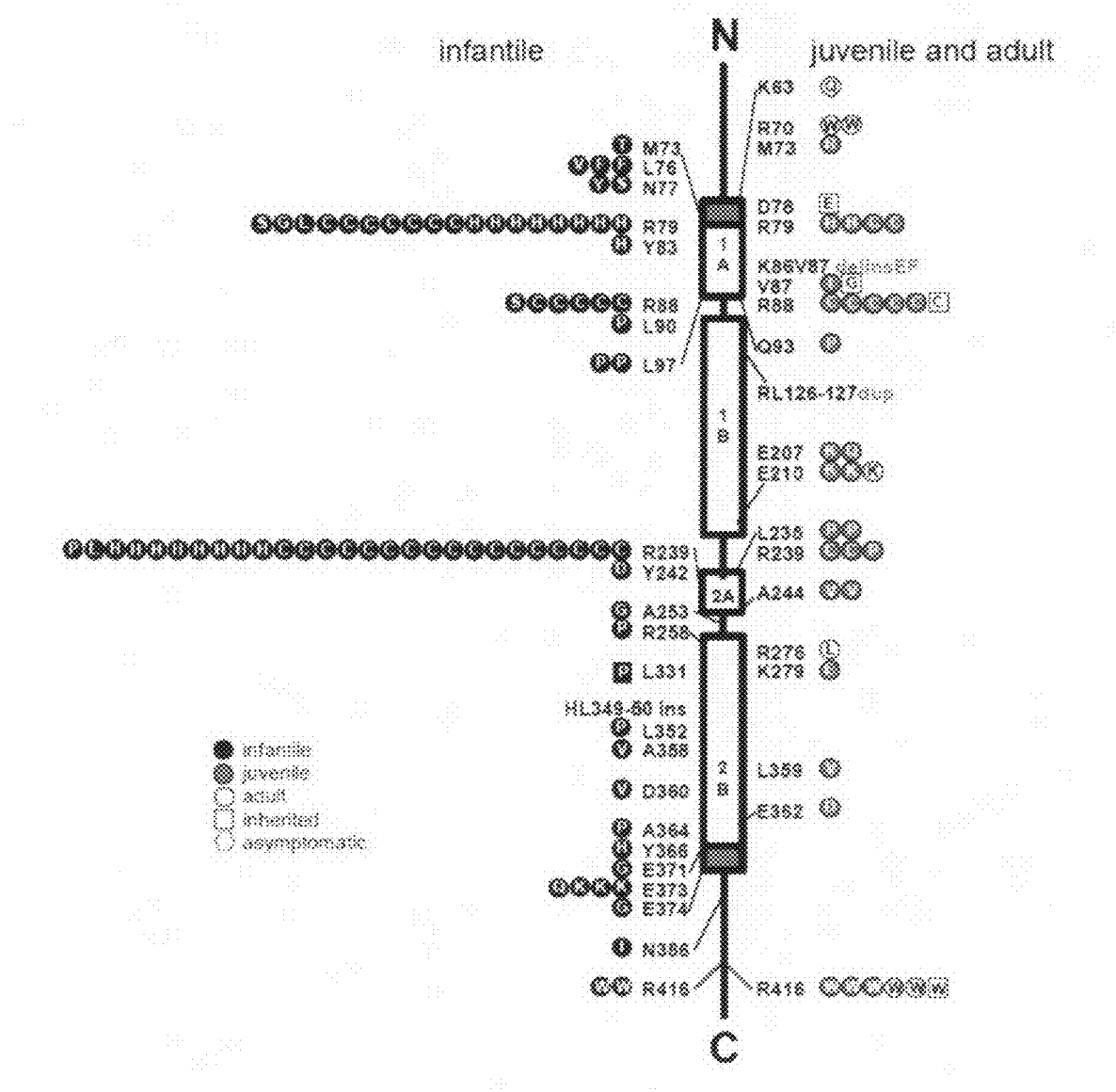
FIG. 1 is a schematic diagram of known Alexander disease associated mutations in GFAP in relation to protein domain structure of intermediate filaments.

Disclosed herein are methods and compositions for the decreasing GFAP levels in a cell. Also disclosed herein are methods and compositions for the treatment of gliosis, Alexander disease, and methods for the identification of such compounds.

"Drug" is used herein in its broadest sense as including any composition or substance that will produce a pharmacologic response, in particular with respect to Alexander disease.

Generally, the nomenclature and the laboratory procedures described below are those well known and commonly employed in the art. Standard techniques are used for DNA and RNA isolation, purification, amplification, and cloning. Enzymatic reactions involving DNA ligase, DNA polymerase, restriction endonucleases, and the like are generally performed according to the manufacturer's specifications. These techniques and various other techniques are generally performed according to Sambrook et al., 1989, Molecular Cloning—A Laboratory Manual, Cold Spring Harbor Laboratory Press, Cold Spring Harbor, N.Y.; Ausubel et al., 1993, Current Protocols in Molecular Biology, Volumes 1-3, John Wiley & Sons, Inc., New York, N.Y.; and Kriegler, 1990, Gene Transfer and Expression: A Laboratory Manual, Stockton Press, New York, N.Y., each of which is incorporated herein by reference in its entirety. Aspects of transcriptional and translational control of gene expression are also disclosed in Sonenberg et al., 2000, Translational Control of Gene Expression, Cold Spring Harbor Laboratory Press, Cold Spring Harbor, N.Y., which is incorporated herein by reference.

Various aspects related to the practice of the present methods, specifically gene expression systems in astrocyte cells, are disclosed in U.S. Pat. No. 5,627,047 ("Astrocyte-specific transcription of human genes"), which is herein incorporated by reference in its entirety.

In one aspect, the present application takes advantage of recent genetic studies, which have identified heterozygous missense mutations in GFAP, the major intermediate filament protein in astrocytes, as the cause of Alexander disease. These studies have transformed the view of this disorder and opened new directions for investigation and clinical practice. Rosenthal fibers, astrocyte dysfunction, and the severe secondary effects on other cells observed in Alexander disease all seem to arise from mutations in the astrocyte intermediate filament, GFAP. This led to this finding by initial studies in transgenic mice that were designed to constitutively overexpress wild type GFAP. These mice developed a lethal phenotype associated with formation of Rosenthal fibers which are indistinguishable morphologically and biochemically from human Rosenthal fibers. These findings have since led to the conclusion that formation of such complex inclusions could be initiated by a primary change in the expression level of GFAP. Hence, although the precise pathogenesis of Alexander disease remains unknown, the mutant GFAPs and the expression levels and/or activity of the GFAP protein present a compelling therapeutic target for intervention, i.e. for treatment of Alexander disease.

"Treating" or "treatment" as used herein refers to the treating or treatment of a disease or medical condition. "Preventing" or "prevention" as used herein refers to the preventing or prevention of a disease or medical condition. An example of a disease or a medical condition is Alexander disease. The term "treating" as used herein includes achieving a therapeutic benefit and/or a prophylactic benefit. The compositions and methods disclosed herein can be used for treatment and/or for prevention of Alexander disease. Therefore, as used herein, reference to "treatment of Alexander disease" is meant to also include the prevention of Alexander disease. Treating Alexander disease is meant to include decreasing the symptoms associated with Alexander disease, for example decreasing the frequency or intensity of seizures, improving acquisition of developmental milestones, or slowing loss of same milestones.

"Therapeutically effective amount" refers to an amount of an active ingredient sufficient to inhibit the development of symptoms and/or to alleviate the existing symptoms of a disease or condition in a subject.

"Down regulation" as used herein refers to the process by which a cell decreases the amount, number or activity of a cellular component, such as RNA or protein, in response to an external variable, e.g. drug. In particular, down regulation refers to the relative decrease in the expression of GFAP mRNA and/or protein. As used herein, down regulation of GFAP is also specifically meant to include a decrease in the amount or level of expressed or produced GFAP protein. Down regulation of GFAP is meant to include a decrease in GFAP protein level by at least 10% in comparison to the GFAP protein level in the absence of treatment, preferably a decrease in GFAP protein level by at least 20% in comparison to the GFAP protein level in the absence of treatment, and more preferably a decrease in GFAP protein level by at least 25%, 30%, 35%, 40%, 45%, or 50% in comparison to the GFAP protein level in the absence of treatment. Down regulation of the activity of a GFAP protein can be accomplished in a variety of ways, for example by decreasing the transcription and/or translation levels of GFAP, by inhibiting the activity of the protein, e.g. via binding to an inhibitor, and in other ways known in the art. For example, it is possible to down regulate GFAP by identifying a drug (e.g. an inhibitor) that binds to GFAP, and thus down regulates GFAP activity in one or more ways. As well, it is possible to target GFAP mRNA with antisense oligonucleotides with the express purpose of down-regulating the synthesis of GFAP protein.

In one aspect, this application takes advantage of discoveries from sequencing the GFAP gene in patients who had died of biopsy or autopsy-proven Alexander disease. Almost all of the examined patients carried non-conservative, heterozygous point mutations in the coding region of GFAP. The mutations altered seven different nucleotides, predicting changes in four different amino acids (all arginines). Following this initial report, a number of other studies have now confirmed and extended these findings.

FIG. 1 illustrates the locations of published Alexander disease associated mutations in GFAP in relation to protein domain structure of intermediate filaments. The boxes indicate the four α-helical sub-domains within the central rod domain, separated by non-helical linkers. Multiple independent occurrences of a mutation are indicated by the number of symbols shown to the right. Where more than one mutation has been reported at the same codon, the predicted amino acid change for each case is shown within the colored circle, square or hexagon. Classification of each case by age of onset is indicated by the color of the circle, square or hexagon (infantile=black; juvenile=gray; adult=open circle; inherited=open square; asymptomatic=open hexagon). N=N-terminal, C=C terminal. Detailed discussions of these mutations and other polymorphisms have been reported.

In one aspect, a embodiment take advantage of the discovery that mutant GFAP is the root cause of Alexander disease. Hence, reducing the levels or preventing GFAP expression (particularly mutant GFAP expression) can be used as an approach for treating the disease. An ideal drug might selectively prevent expression of just the mutant allele, but this is technically challenging and also involves approaches that have not yet reached clinical practice for any disease. Alternatively, and especially in light of the fact that complete absence of GFAP is such a mild phenotype in the mouse, an acceptable alternative would be suppression of GFAP expression from both alleles.

In some embodiments, devising treatment strategies for Alexander disease should strive to eliminate the mutant GFAP protein or prevent its expression in the first place. In one aspect, a method for treating Alexander disease by preventing and/or reducing the expression of GFAP is provided. It is expected that down regulation of GFAP should result in reduced megalencephaly in subjects that are susceptible to Alexander disease. "Megalencephaly" is a condition in which there is an abnormally large, heavy, and usually malfunctioning brain. In megalencephaly, the brain weight is greater than average for the age and sex of the subject (e.g. infant or child).

As used herein, the term "subject" encompasses mammals and nonmammals. Examples of mammals include, but are not limited to, any member of the mammalian class: humans (including patients and volunteers), non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like.

Provided are methods for identifying a down-regulator of glial fibrillary acidic protein (GFAP) expression. The methods include: providing GFAP; contacting the GFAP with a test compound; and determining whether the test compound down regulates GFAP. The methods may further include the step of determining whether the test compound binds to the GFAP, the binding being an indication that the test compound is effective for decreasing the intensity of a symptom associated Alexander disease. The GFAP may be provided by cells that express GFAP. The GFAP may be provided by expression in a glioma cell line, expression in astrocytes, or expression in a spinal cord slice. In the practice of the methods, the test compound may be FDA approved for human use. The test compound may also be identified from a library of natural products. The test compound may be an antidepressant, and preferably the test compound may be a tricyclic antidepressant. The test compound may be selected from the group consisting of diaziquone, clomipramine, chrysophanol, amitriptyline, tamoxifen, amlodipine, embelin, thioridazine, ritanserin, ketotifen, kanamycin, 4-acetamidophenyl salicylate, and terfenadine.

If the test compound is found to down regulate GFAP, the compound may be administered to a subject to determine if the compound decreases intensity of Alexander disease.

Testing of the compounds can be performed in vivo in several different ways. Typically the compounds are administered via one of several routes—oral, intraperitoneal, subcutaneous, or intravenous. Depending on the time course of drug entry into the central nervous system, as well as metabolism and excretion, the drugs may be administered at any of several intervals, such as 1-3 times per day, or 1-3 times per week, or every other day. The optimal dosing schedule is preferably determined empirically. The concentration(s) of the drug(s) to be used will be guided by the concentrations used in the initial drug screening that was performed in cell culture, where activity at 10 µM is defined as the criteria for a compound to merit further testing. Subsequent cell culture testing evaluates activity at higher and lower concentrations to determine, for example, toxic levels and lowest effective dose. Initial doses used for in vivo testing are based on doses known from publications to be tolerated in chronic dosing regimes with minimal side effects. Animals are treated for varying lengths of time, from 1 day through 6 months, before collection of brain and/or spinal cord for measurement of GFAP levels. Cerebrospinal fluid (CSF) is another potential biopsy site for measurement of GFAP protein that would be feasible to use in human patients. Efficacy is determined by the degree of reduction of GFAP protein in central nervous system tissue or CSF. If the initial doses do not produce a reduction in GFAP, higher doses can be tested after determining the Maximum Tolerated Dose for each compound (the dose that produces no significant side effects after short periods of administration).

Provided herein are compositions and methods that can be used for treatment of Alexander disease. Compounds that down regulate GFAP may be suitably identified from screens of compounds that are already approved for human use by the FDA. Thus, one embodiment, provides for the screening of collections of compounds that are already FDA-approved for unexpected but beneficial properties. Thus, for example, the NINDS Custom Collection or Spectrum Collection from MicroSource Discovery Systems, Inc. (Gaylordsville, Conn.), or the Prestwick Chemical Library® from Prestwick Chemical (Illkirch, France) can be screened for candidate compounds. Identified compounds can then be tested in suitable animal models. In some embodiments, drugs from this screen can be considered of interest if they show activity in more than one related assays.

Given the rare and likely orphan status of Alexander disease, an advantageous place to search for a GFAP-suppressing drug is among the collections that are already approved for human use by the FDA. This same strategy has yielded promising results in an NINDS-supported consortium to identify novel treatments for late-onset neurodegenerative diseases.

A variety of options exist for monitoring GFAP expression in cultured astrocytes or astrocyte-like cells; these vary in complexity and degree of similarity to astrocytes in vivo (the ultimate target population). In one example, using for a screen the available NINDS Custom Collection libraries, it is possible to, for example: 1) screen for suppression of GFAP expression in glioma cell lines; 2) screen for suppression of GFAP expression in primary astrocyte cultures; 3) screen for suppression of GFAP expression in explant cultures of spinal cord. Thus different types of cells can be used which express GFAP, and which can be tested for down regulation of GFAP with a variety of compounds.

"Glioma" is a tumor arising from glial cells, in the supporting tissue intermingled with the essential elements of nervous tissue especially in the brain, spinal cord, and ganglia.

"Astrocytes" (also known collectively as "astroglia") are characteristic star-shaped glial cells in the brain and spinal cord.

"Explant cultures of spinal cord" refer to explant cultures that are prepared using methods known in the art, e.g. as described in Rothstein and Kuncl, *J. Neurochem.* 65: 643-651 (1995), herein incorporated by reference.

One or more of these screens can be used to identify compounds that warrant further evaluation for reducing expression of mutant GFAPs and the pathology associated with Alexander disease. As described herein, mouse lines expressing some of the most common mutant GFAPs found in Alexander disease patients have been generated, thus offering an in vivo system in which promising compounds can subsequently be tested. In some examples, by restricting the focus to the FDA-approved list, successful identification of candidate drugs could offer immediate therapeutic benefit to Alexander disease patients.

It is contemplated that the examples described above include alternative embodiments. In the case of glioma cell lines (gliomas), not only human U251 cell lines but many other glioma cell lines that express GFAP may be used as well. In the case of primary astrocyte cultures, neural stem cells may be used as a source of purified astrocytes that express GFAP, or human embryonic stem cells may also be used for the production of astrocytes that express GFAP. Primary cultures of mouse brain are also a simple starting point. If use of proliferating cell cultures complicates interpretation of results due to drug effects on proliferation itself rather than on gene expression, it may be possible to use mitotically arrested cells instead. Fibroblasts that are mitotically arrested are already used as feeders for embryonic stem cells in the inventors' gene targeting experiments.

Once identified, drugs that show evidence of selective suppression of GFAP expression (such as in any of the three culture systems exemplified herein) can be considered suitable candidates for further study. Dose response curves can be obtained with the cultures, and then it may be possible to move to testing effects on GFAP expression in vivo, using mice or other lab animals.

Mouse models expressing both normal and mutant forms of GFAP that develop Rosenthal fibers, the hallmark pathological feature of the human disorder have been developed.

In one aspect, the methods of identifying drugs that reduce expression of GFAP in subjects can be practiced with primary cultures of mouse astrocytes in a 96-well format. Screens can be devised to detect changes in GFAP promoter activity, GFAP protein level, or both promoter activity and protein level. If desired, such screens can be applied on libraries enriched in compounds that are already approved for human use by the FDA. Identified compounds that are active at micromolar levels in suppressing expression of GFAP may be considered as potential drugs for Alexander disease. In one embodiment, assays using adapted primary cultures of mouse astrocytes were performed in a 96-well format. Screens were devised to detect changes in either GFAP promoter activity or protein levels for inhibitors of GFAP expression. A "Known Bioactives" library was successfully screened at the Keck-UWCCC Small Molecule Screening Facility (SMSF) through the Lead Discovery Initiative (LDI) program. This particular compound library consists of FDA approved drugs and is useful for identifying new indications, i.e. drug repurposing.

One embodiment relates to the identification of compounds that are selective in their effects on GFAP. General reductions in protein expression are not desirable, and there are some aspects of the molecular profile of Alexander astrocytes that may be worth enhancing rather than suppressing, such as the up-regulation of certain stress response genes, including αB-crystallin and HSP25, which may be a protective effort by the cell. Other astrocyte genes are thought to be critical for neuroprotection, such as the glutamate transporters, and it should be equally important to verify that their expression is not altered in deleterious ways.

Drug screening for treatment of Alexander disease offers several unique advantages that are of both practical and scientific interest. First, a single gene (GFAP) and biological process (gene expression) are targets. The disease is remarkably homogeneous from a genetic standpoint, with greater than 90% of patients carrying mutations in the same gene, and showing nearly 100% penetrance. Second, the null phenotype is likely to be mild, or at least far preferable to the disease, thus allowing pursuit of general inhibition of GFAP expression rather than attempt allele-specific strategies. Third, the inventors have prepared animal models that are available for in vivo testing of any drug candidates identified as part of the screening methods described herein. Last, Alexander disease is the first example of a primary disorder of astrocytes, a major glial cell in the vertebrate central nervous system, and developing novel pharmacological strategies for treating this disorder may promise new insights into how astrocyte dysfunction contributes to generalized CNS disease.

It is expected that down regulation of GFAP in subjects would provide a benefit to the subjects in the form of a reduction of symptoms associated with Alexander disease, and/or slowing in the progression of the disease.

As discussed above, the down regulation of GFAP can be effective as a treatment for Alexander disease. Thus, in accordance with the disclosed embodiments, compositions are provided that can down regulate GFAP expression and can thus be used for the treatment of Alexander disease. In some embodiments, these compositions include, but are not limited to, diaziquone, clomipramine, chrysophanol, amitriptyline, tamoxifen, amlodipine, embelin, thioridazine, ritanserin, ketotifen, and salicylate. It is expected that administering to the subject that is susceptible to Alexander disease one or more of the above compounds should decrease the intensity of a symptom associated with Alexander disease. These compositions can be optionally mixed with one or more pharmaceutical carriers know in the art, and can be administered to subjects in a variety of ways.

In other embodiments, compositions that can down regulate GFAP expression and can thus be used for the treatment of Alexander disease include, but are not limited to, antidepressant (antidepressant drugs), and/or antidepressants (antipsychotic drugs), such as tricyclic antidepressants ("TCAs").

TCAs are a class of antidepressant drugs first named after the drugs' molecular structure, which contains three ring structures, which may be the same or different. Suitable examples of TCAs include clomipramine, amitriptyline, butriptyline, amoxapine, desipramine, dosulepin hydrochloride, doxepin, imipramine, dibenzepin, iprindole, lofepramine, nortriptyline, opipramol, protriptyline, and trimipramine.

In some embodiments, the GFAP lowering compound may include betulinic acid and/or a betulinic acid derivative. Examples of suitable betulinic acid derivatives include 3-aminobetulinic acid (compound 4) and the other betulinic acid derivatives shown below (labeled as compounds 3, 7, ABA1, ABA2, BA1, and BA2).

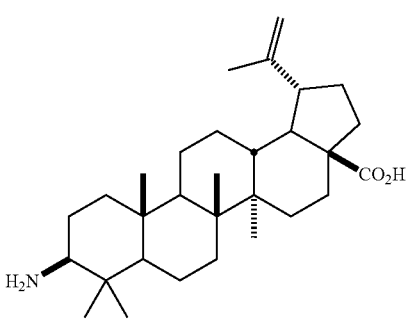

4

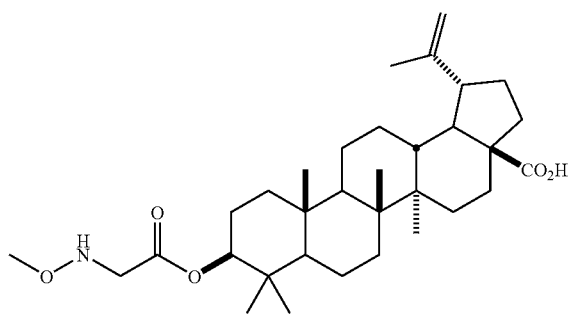

3

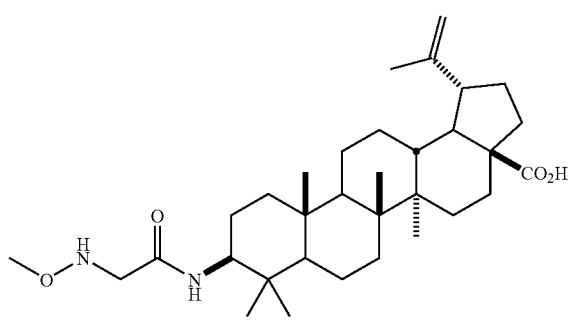

ABA1

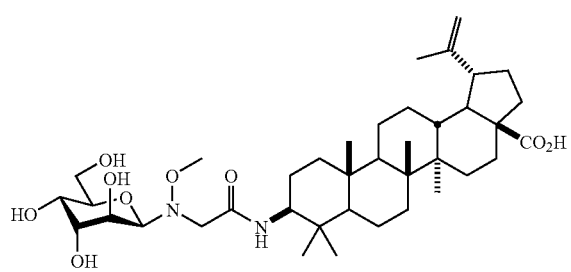

ABA2

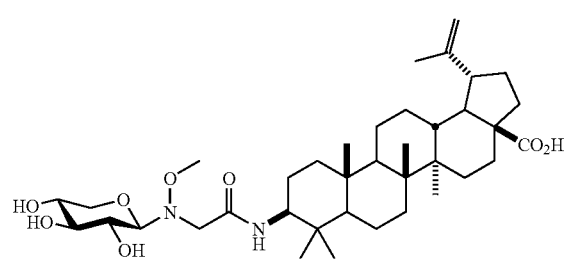

BA1

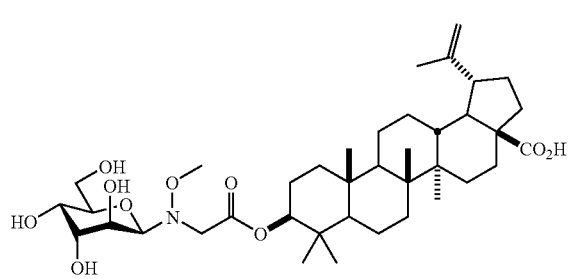

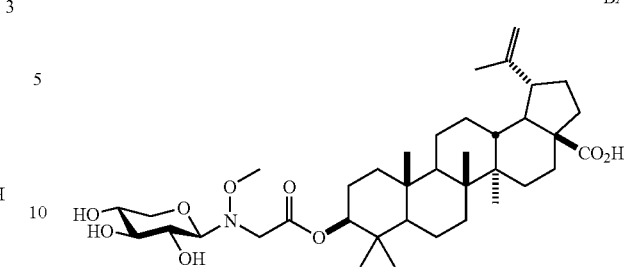

BA2

Suitable GFAP lowering compounds include betulinic acid derivatives such as 3-O—(N-glycosyl-N-methoxyglycyl) betulinic acids and N—(N'-glycosyl-N'-methoxyglycyl)-3-aminobetulinic acids. Suitable the 3-O—(N-glycosyl-N-methoxyglycyl)betulinic acids include 3-O—(N-pentosyl-N-methoxyglycyl)betulinic acids and 3-O—(N-hexosyl-N-methoxyglycyl)betulinic acids.

The 3-O—(N-glycosyl-N-methoxyglycyl)betulinic acids may include 3-O—(N-aldopentosyl-N-methoxyglycyl)betulinic acids and 3-O—(N-aldohexosyl-N-methoxyglycyl)betulinic acids. The 3-O—(N-pentosyl-N-methoxyglycyl) betulinic acids may include (3S)—O—(N-methoxy-N-D-altrosylglycyl)betulinic acid. The 3-O—(N-pentosyl-N-methoxyglycyl)betulinic acids may include 3-O—(N-methoxy-N-altrosylglycyl)betulinic acid. The 3-O—(N-aldohexosyl-N-methoxyglycyl)betulinic acids may include 3-N—(N'-methoxy-N'-xylosylglycyl)betulinic acid. The 3-O—(N-aldohexosyl-N-methoxyglycyl)betulinic acids may include (3S)—N—(N'-methoxy-N'-β-D-xylosylglycyl) betulinic acid.

The N—(N'-glycosyl-N'-methoxyglycyl)-3-aminobetulinic acids may include N—(N'-pentosyl-N'-methoxyglycyl)-3-aminobetulinic acids and N—(N'-hexosyl-N'-methoxyglycyl)-3-aminobetulinic acids. The N—(N'-glycosyl-N'-methoxyglycyl)-3-aminobetulinic acids may include N—(N'-aldopentosyl-N'-methoxyglycyl)-3-aminobetulinic acids and N—(N'-aldohexosyl-N'-methoxyglycyl)-3-aminobetulinic acids. The N—(N'-aldopentosyl-N'-methoxyglycyl)-3-aminobetulinic acids may include 3-N—(N'-methoxy-N'-altrosylglycyl)betulinic acid. The N—(N'-aldopentosyl-N'-methoxyglycyl)-3-aminobetulinic acids may include (3S)—N—(N'-methoxy-N'-□-D-altrosylglycyl)betulinic acid. The N—(N'-aldohexosyl-N'-methoxyglycyl)-3-aminobetulinic acids may include 3-N—(N'-methoxy-N'-xylosylglycyl)betulinic acid. The N—(N'-aldohexosyl-N'-methoxyglycyl)-3-aminobetulinic acids may include (3S)—N—(N'-methoxy-N'-β-D-xylosylglycyl)betulinic acid.

Suitable betulinic acid glycoside derivatives for use in the present methods may include those having the structure or -continued

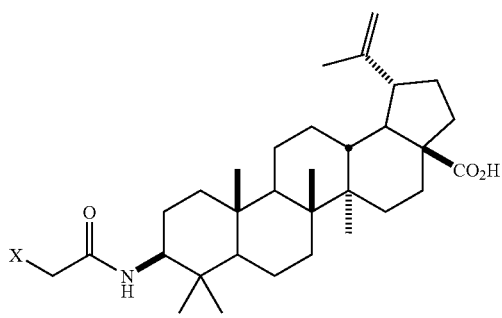

wherein "X" is selected from:

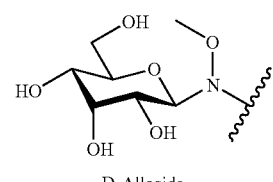
D-Alloside

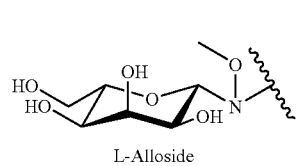
L-Alloside

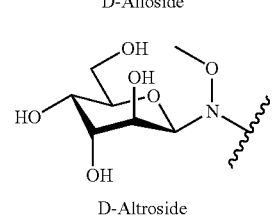
D-Altroside

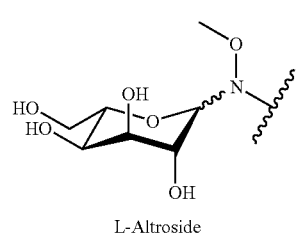
L-Altroside

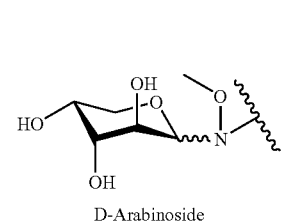
D-Arabinoside

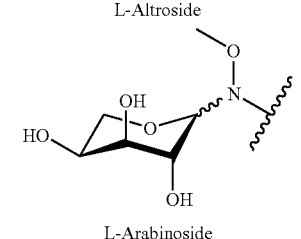
L-Arabinoside

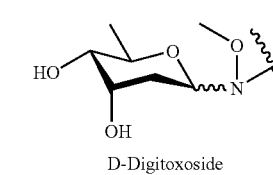
D-Digitoxoside

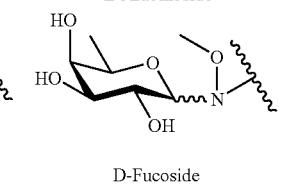
D-Fucoside

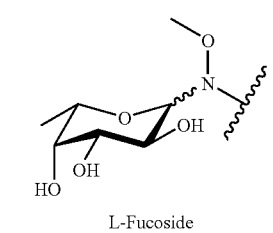
L-Fucoside

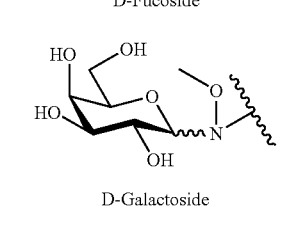
D-Galactoside

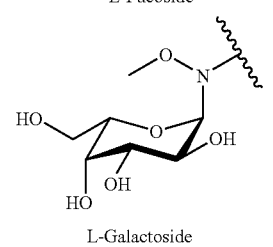
L-Galactoside

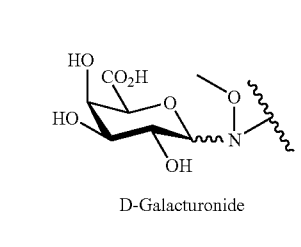
D-Galacturonide

-continued

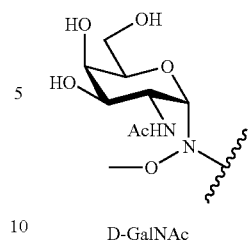
D-GalNAc

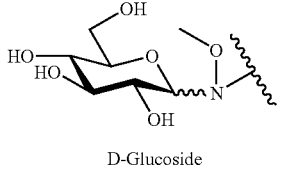
D-Glucoside

L-Glucoside

D-Glucoside, 2-fluoro

D-Glucoside, 3-deoxy

D-Glucoside, 6-deoxy

D-Glucoside, 3-O-Methyl

D-Glucuronide

D-Glucurono, 6,3-lactonide

D-Lyxoside

L-Lyxoside

D-Mannoside

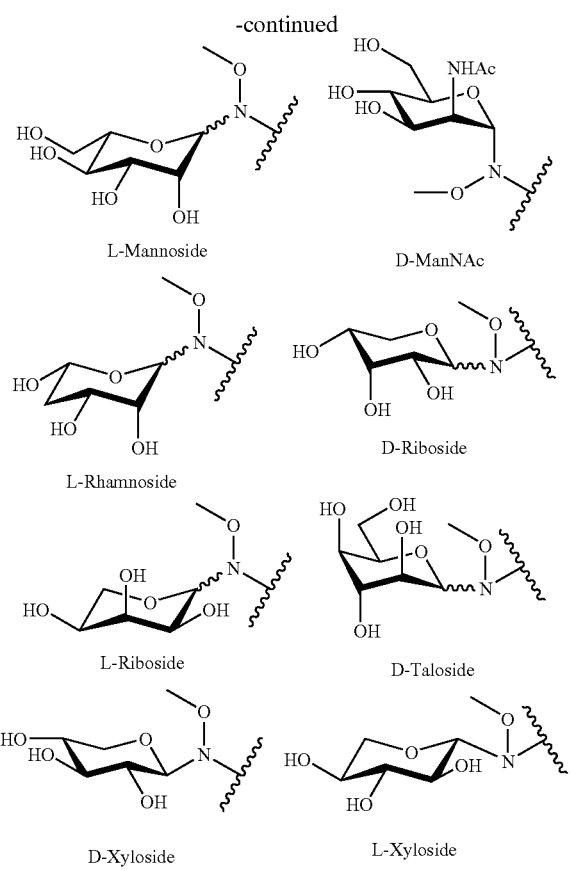

Administration of the compositions described herein can be performed in a variety of ways, e.g. orally, enterally, or parenterally. In some embodiments, administration of the compositions is provided in a daily dose.

In other aspects, administration of the compositions is provided in alternative schedules that are more frequent, such as, for example, twice a day, or less frequent, such as every other day, three times a week, or once a week.

Provided herein are pharmaceutical compositions. Such compositions include a therapeutically effective amount of a compound, and a pharmaceutically acceptable carrier. As used herein, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates; antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

Pharmaceutical compositions described herein generally contain a therapeutically effective amount of the compound, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

It will be appreciated that the present methods and compositions may find utility with populations of subjects that are susceptible to Alexander disease, including but not limited to infants, juveniles, and adults.

The compositions can be used in combination with other methods known in the art and used for down regulation of protein expression. For example, the compositions may be used in combination with GFAP antisense oligonucleotides. The use of antisense oligonucleotides for therapeutic purposes was first proposed in 1978. Antisense oligonucleotides can form a stable heteroduplex with the target GFAP mRNA, and this antisense oligonucleotide hybridization results in down regulation of the targeted synthesis of GFAP protein. Down regulation of a protein is functionally equivalent to a decrease in its activity, the mechanism of action of most traditional pharmaceutical drugs.

It is to be understood that the embodiments disclosed herein are not limited to the particular methodology, protocols, subjects, or reagents described, and as such may vary.

It is also to be understood that the terminology used herein is for the purpose of describing particular embodiments, and is not intended to be limiting.

EXPERIMENTAL EXAMPLES I

As detailed below, various types of culture systems and two types of assays can be used for evaluating expression of GFAP and screening for compounds of interest. Glioma cell lines are the easiest to grow but also least likely to resemble a normal astrocyte, whereas at the other extreme the explant cultures will preserve a substantial amount of anatomic integrity but are labor-intensive. Primary cultures of astrocytes are intermediate in both respects. Similarly, the ELISA assay for GFAP protein is well established (Messing et al., *Am. J. Pathol.* 152: 391-398 (1998); Hagemann et al., *Hum. Mol. Genet.* 14: 2443-2458 (2005); Hagemann et al., *J. Neurosci.* 26: 11162-11173 (2006)), highly quantitative, and ultimately it is a decrease in GFAP protein that is of interest, whether by transcriptional or posttranscriptional mechanisms or combinations thereof. For relatively stable proteins such as intermediate filaments, reporter gene assays may be better for detecting rapid decreases in gene expression.

A. Animal Models—General Considerations

Various animals can be used for these experiments. Non-limiting examples of animals that can be used for these experiments include mice of the FVB/N, 129S6, or C57BL/6J strains. The ages of the mice can be from newborn through adult. Both sexes can be used. Large numbers of animals are generally required in order to generate fertilized eggs and blastocysts for microinjection, for raising viable transgenic pups from injected embryos, and for maintaining breeding lines of animals once transgenics are produced. The experiments may require expression or mutation of genes in vivo through transgenic technology, and this technology is most advanced in the mouse system. The mice can be housed in an air-conditioned AALAC-accredited facility in a colony free of all known pathogenic rodent viruses. Before surgical procedures, mice are anesthetized with Avertin. Sacrifice is performed with an overdose of sodium pentobarbital or asphyxiation by $CO_2$. Both methods are approved by the Panel on Euthanasia of the American Veterinary Medical Association.

B. Screen for Suppression of GFAP Expression in Glioma Cell Lines

In this example, glioma cell lines are used due to their known expression of GFAP and their ease of culturing. Such lines have previously been used for studies of GFAP regulation. Although glioma cell lines have limitations, it may be appropriate to employ these cells as part of a balanced approach to screening for GFAP-suppressing drugs. Many of the detailed techniques (drugs, assays of gene expression) are similar for the examples disclosed herein.

1. Choice of Cell Lines

In one embodiment, the U251 human astrocytoma cell line can be used. This cell line expresses high levels of GFAP, roughly comparable to that found in primary cultures of rat astrocytes, and has been previously used (Besnard et al., *Biol. Chem.* 266:18877-18883 (1991)). Standard growth conditions for the U251 cells in 96-well formats can be established, plating 100-1000 cells per well, for example, using densities based on previous studies of proliferation using this cell line (Rutka and Smith, *Cancer Res.* 53:3624-3631 (1993)) and monitoring growth over a four day period to mimic the planned duration of drug treatment. In one embodiment, a plating density is chosen that maintains monolayer conditions but achieves near confluent levels by the end of the growth period, thus avoiding significant cell death.

2. Drug Library and Treatment

In one example, the NINDS Custom Collection from MSDiscovery (National Institute of Neurological Disorders and Stroke, National Institutes of Health, Bethesda, Md.) can be used. This library includes 1040 compounds selected based on FDA-approval and/or availability as controlled substances or natural products, and enriched for ability to cross the blood-brain barrier. The drugs are provided as 10 mM stocks in DMSO using 96-well plates. Cells can be plated at a desired density (e.g., 100-1000 cells per well) and grown in a standard medium consisting of Dulbecco's MEM containing 2 mM L-glutamine and 10% fetal bovine serum. At 24 hr after plating 0.5 µl of drug is added to each well for a final concentration of 50 µM (or DMSO alone as a control). This range of concentration (between about 10-100 µM) is a common starting point for high-throughput drug screening as these are blood concentrations typically reached in actual clinical use. The cells can be grown for another 72 hours at which time they are harvested for analysis of gene expression as detailed below.

3. Assays of GFAP Expression

A set of assays aimed at measuring GFAP protein level can be used. Alternatively, or in addition, another set of assays can be aimed at measuring transcription levels from the GFAP promoter.

GFAP protein level can also be measured in a variety of ways. For example, to assess GFAP protein level it is possible to perform a sandwich ELISA assay. This assay is sensitive and quantitative (Messing et al., *Am. J. Pathol.* 152: 391-398 (1998), herein incorporated by reference in its entirety). If performed in 96-well assay format, total protein can also be measured for all wells so that the GFAP levels are expressed per mg protein (to correct for non-specific toxicity). In addition, sensitivity and dynamic range can be modified and possibly improved over the existing method by switching to a luminescent substrate for the alkaline-phosphatase-conjugated secondary antibody.

GFAP transcription levels can be measured in a variety of ways. For example, to assess GFAP transcription one can employ the Dual-Glo assay system from Promega (Madison, Wis.). One skilled in the art can take advantage of reporter gene constructs that utilize the 2.2 kb human GFAP promoter, using e.g., lacZ (Brenner, *Brain Pathol.* 4: 245-257 (1994)), the S65T mutant of GFP (Zhuo et al., *Dev. Biol.* 187: 36-42 (1997)). Since reporters are relatively stable proteins with long half-lives, luciferase may be advantageously used. The Dual-Glo system (Promega) employs two types of luciferase that allow simultaneous correction for the possible artifacts of non-specific toxicity or generalized suppression of gene expression. Using the pGL3-Basic vector, the firefly luciferase can be placed under the control of the 2.2 kb human GFAP promoter. Second, the Renilla luciferase can be placed under the control of the ubiquitously expressed hGAPDH promoter murine ROSA26 promoter (Alexander et al., *Proc. Natl. Acad. Sci.* USA 85: 5092-5096 (1998)). This second construct can serve as the general indicator for overall gene expression.

Stable transfectants can be prepared by co-transfection of both plasmids together using standard techniques already successful with the U251 cell line (Chen and Liem, *J. Cell Biol.* 127: 813-823 (1994)). Briefly, cells are grown to 70% confluence, washed, and then treated with a mixture of 10 µg lipofectin (GIBCO-BRL), 10 µg plasmid DNAs, and 1 µg pSV2-neo per ml for 5 hrs at 37° C. The cells are then washed in complete medium, grown to confluence, and then given 500 µg/ml G-418 for positive selection. Resistant clones are isolated, and co-integration of both plasmids verified by PCR and Southern blotting. Stable transfectants can be chosen for future use once their properties are validated by showing expected responses to agents known to cause either up or down-regulation of GFAP mRNA, such as corticosterone, TGF-β, and FGF-2.

Cultures can be plated and treated with the NINDS drug collection as described above, and then each well measured for luciferase activity using a 96-well luminometer and Dual-Glo reagents. The ratio of GFAP-firefly luciferase to the R26-Renilla luciferase is then computed for each well.

In embodiments, these methods can be used to identify drugs that reduce levels of GFAP protein or GFAP transcription. For both the protein and reporter gene assays an arbitrary standard (for example, 2-fold reduction) can be set as a criterion that a particular drug warrants further study. One skilled in the art is also cognizant of the fact that GFAP expression in U251 cells is itself linked to cell density, so that GFAP expression typically drops to low levels immediately upon re-plating at low density and then reaches a peak at confluency after about 4 days. Higher levels of expression could be obtained simply by plating at a higher initial density. Controls for normalizing to mg protein or R26-luciferase levels in each well should take into account effects on growth rate and cell density. However, if a particular drug is found to reduce both GFAP and cell number in the initial screen, follow-up studies should examine effects on GFAP expression under conditions where cell densities are the same.

There are few published studies on the turnover rate of GFAP protein. Only one study has addressed the turnover of GFAP in vivo, and found it to be quite stable with a half-life of several weeks. However, in cultured cells turnover is faster. In primary rat astrocyte cultures, GFAP was degraded with dual kinetics, with 40% of the GFAP pool showing rapid turnover (t½~12-18 hrs.), and 60% of the GFAP pool showing much slower turnover (t½~8 days). Thus, assays for GFAP protein levels may be supplemented with assays for detecting changes in GFAP transcription, e.g. using reporter gene assays.

C. Screen for Suppression of GFAP Expression in Primary Astrocyte Cultures

Primary cultures of astrocytes are closer to normal astrocytes than are transformed cell lines, and reasonably easy to culture in large quantities. Potential drawbacks include increased labor in preparation, more variability, and the possibility of low-level contamination by other cell types. Nevertheless, use of primary cells represents a useful and eminently feasible alternative, or addition, to cell lines for screening response to drugs.

Primary cultures of neonatal mouse cerebral cortical astrocytes can be prepared as previously described (Eng et al., *J. Neurosci. Res.* 53: 353-360 (1998) herein incorporated by reference). Briefly, brains are removed from neonatal mice at P1-P3 (FVB/N strain), meninges stripped by rolling on filter paper, and the cortex dissected free from hippocampus, brain stem, and cerebellum. The tissues are mechanically dissociated and grown in T-75 flasks (3-4 brains per flask) for 24 approximately 1 week, then shaken overnight to remove loosely attached oligodendrocytes and microglia. The adherent cells (predominantly astrocytes) are then trypsinized and re-plated. This procedure typically results in cultures that are 95% pure based on GFAP staining (for astrocytes) or Mac1 staining (for microglia). For drug screening, it is possible to plate directly into 96-well plates. As with the U251 studies (above), initial experiments can be performed to determine the optimal plating density for cells to grow to confluence within a week and yield suitable levels of GFAP expression within the planned time period of drug exposure.

1. Drugs and Assay for GFAP Protein

The choice of library, drug concentration, treatment period, and ELISA assay for GFAP protein can be identical to that described above for the U251 studies. The assays for GFAP gene transcription can, for example, use the same reporter genes described for U251 cells. First, transgenic mouse lines that integrate and express both Dual-Glo luciferase constructs can be made. Transgenic founders can be generated using standard protocols, in the FVB/N inbred background. The two luciferase constructs can be co-injected, which typically leads to co-integration at a single chromosomal site. Conceivably co-integration might lead to one promoter influencing the other, but this does not appear to have happened in practice. Founders can be identified by PCR of DNA isolated from tail biopsies. Mice carrying both transgenes are then screened for expression without the need for sacrifice, exploiting the utility of retinal astrocytes as indicators of astrocyte expression throughout the CNS as previously described (Wakabayashi et al., *BioTechniques* 26: 302-307 (1999)). This approach allows efficient identification of relevant founders without the time and expense of expanding each one into a line. Once lines are established, tissue and cell-specificity can be verified using RT-PCR and immunohistochemistry (e.g., using a polyclonal antibody specific for the firefly luciferase such as the commercially available antibody from Promega). Quantitation of luciferase activity in cell culture extracts can be measured using the same Dual-Glo system.

In some embodiments, drugs that produce a certain level of reduction (for example, 2-fold) in GFAP expression can be identified. This can be determined through protein and/or reporter gene assays, or combinations thereof. The drawbacks to the use of primary cultures compared to cell lines are the extra labor (for personnel) and cost (for animals). These potential problems may be outweighed by the relative normalcy of primary cells (compared to transformed cell lines), the ready access to mouse tissues (as opposed to human, which would be much more difficult to procure on a regular basis), and the options mice offer for use of genetically engineered lines carrying reporter gene constructs. In the event that a particular drug shows promise based on the primary astrocytes but shows no effect in the glioma cell lines as described above, greater weight can be placed on the results from the primary cells. In the event that a particular drug leads to reduced expression in the glioma cells but not in the primary astrocytes, a wider dose response range in the primary astrocytes can be explored, to be sure that a biologically significant effect has not been missed. For example, the single high dose planned for the initial screen may cause nonspecific toxicity or suppression in the primary astrocytes that would mask any specific effect that could be achieved at lower doses. Alternatively, a higher dose of a compound may be required to detect the effects of the drug in the assay, or a longer incubation period may be necessary for drug activity to be noted.

While the GFAP protein studies can be done using cultures derived from conventional mice, the reporter gene assays require new luciferase transgenics. The transgenic mice described above can be suitably used in these experiments.

D. Screen for Suppression of GFAP Expression in Explant Cultures of Spinal Cord

Organotypic explants are currently the closest to a normal astrocyte without using live animals. Protocols have recently been developed for quickly generating large numbers of equivalent explants that are suitable for testing toxicity or neuroprotection of various drugs. Such a system has been utilized for drug screening to protect against glutamate excitotoxicity in the spinal cord (Rothstein and Kuncl, *J. Neurochem.* 65: 643-651 1995)), and even applied a similar system for screening the large number of compounds in the FDA drug library.

In this example, explant cultures of P7-8 mouse spinal cord can be established, through the adaptation of the methods described for rat spinal cord by Rothstein and colleagues (Rothstein and Kuncl, *J. Neurochem.* 65: 643-651 (1995); Jackson et al., *Current Protocols in Neuroscience* 9.13.1-9.13.20 (2002)). Briefly, 350 µm transverse slices from the lumbar cord are cut using a McIlwain tissue chopper and grown on Millicell CM 12-mm membranes in 24-well tissue culture plates, one explant in each well. The explants are allowed to grow (and recover) for 7 days before treatment with drugs begins. The recovery period is important to allow trauma to neurons and astrocytes to subside, and presumably allow GFAP expression levels to return to a basal level. If desired, in initial experiments the optimal recovery period for astrocytes can first be verified. For assays of GFAP protein using the ELISA, inbred FVB/N mice can be used. For assays of GFAP transcription, the luciferase transgenics (in the same FVB/N background) made as above can be used. It is possible to obtain approximately 5-10 explants from each mouse, or roughly 1-2 plates per litter of mice.

The choice of library and drug concentration can vary. In some embodiments, the choice of library and drug concentration can be as described above. Explants can be treated for 7 days with one re-feeding at 3 days, instead of the shorter treatment periods used for the cultures above. However, fewer compounds can be tested in each set of cultures because each plate only provides 24 wells. Depending on the variability of the explants, it may be possible to use as few as two per drug and screen roughly 12-24 drugs from each litter of mice. At this rate screening an entire NINDS library as referenced herein would require 87 separate experiments (i.e. litters). In some examples, it may be possible to start with candidate drugs identified through the literature (e.g., dexamethasone, quercetin) and any that show positive results in the assays of the examples described above. Assays for GFAP protein and GFAP gene transcription—GFAP ELISA and luciferase assays—can be performed as described above for the primary astrocyte cultures.

The stability of GFAP protein could make it difficult to detect the effects of acute drug treatments. In addition, GFAP half-life has not been studied before in organotypic explants, and may be closer to the long half-life reported for astrocytes in vivo. One alternative is to extend the period of drug treatments, although this may be more costly in terms of reagents given the volume of media that is required. A second issue has to do with anatomic variability. An assumption of this experimental design is that the explants are reasonably consistent in the amount of GFAP that they produce (or are capable of producing). To achieve this goal of consistency requires choosing an anatomical region that exhibits minimal variability in cell populations, both neuronal and glial. In the studies of Rothstein and colleagues using rats, sufficient numbers of slices were obtained per animal that one litter (10 pups) yielded 150 slices, and they typically placed five slices per well for screens involving small numbers of drugs and two slices per well for the NINDS screen of 1040 drugs. Alternatives to spinal cord that have been widely used for explants are cerebellum and hippocampus, and these can be considered if spinal cord does not yield sufficient numbers of slices per animal or are too variable.

EXPERIMENTAL EXAMPLES II

The examples below detail the testing of various compounds for the ability to reduce the amount of GFAP protein and GFAP promoter activity in neuronal cells and in mouse brain. Four different cell-based screens were performed to identify compounds that would reduce GFAP protein levels and/or GFAP promoter activity. Toxicity and long term effects of a subset of the compounds was also evaluated. In addition, eight different betulinic acid derivatives were tested for the ability to reduce the amount of GFAP protein in cells and decrease GFAP promoter activity.

One exemplary compound, clomipramine, was also tested in transgenic mice to evaluate GFAP protein levels and promoter activity after either acute or chronic treatment.

A. Cell-Based Assays—Four Screens

Cell-based assays were performed as four different screens using enriched cortical primary astrocyte cultures developed from transgenic mice expressing both firefly and Renilla luciferase reporter genes were generated. Briefly, the 'firefly luciferase was placed under the control of a 2.2 kb human GFAP promoter to monitor GFAP transcription, and the Renilla luciferase was placed under the control of a 0.5 kb human GAPDH (glyceraldehyde 3-phosphate dehydrogenase) promoter to monitor transcription of a housekeeping gene for signal normalization. See section B, below for more detail regarding the development of transgenic mouse strains. Cells used in the following examples (e.g., the cortical primary astrocyte cells termed "172.9 cells," described below) were developed from the transgenic mice described in section B.

Enriched cortical primary astrocyte cultures were obtained from FVB-Tg(GFAP-luc,GAPDH-luc)172.9Mes/J mice (JR#9638) at post-natal days 1-2 as follows. Briefly, the cortices from individual pups were freed of meninges and placed into DMEM (Gibco) without serum, mechanically disassociated into single cells, suspended in medium containing DMEM supplemented with 10% fetal bovine serum (FBS; Hyclone), 100 U/ml penicillin, 100 µg/ml streptomycin (Gibco), seeded into T25 flasks (one brain per flask), and maintained in a humidified 5% $CO_2$ atmosphere at 37° C. At 48 hours the serum was reduced to 1% FBS. Medium was changed every 3 days. At 14-16 days in vitro (DIV), the flasks were shaken overnight at 200 rpm to remove oligodendrocytes and microglia. The adherent astrocyte population was detached by incubating briefly in 0.25% trypsin-EDTA (Gibco). The cells were then suspended in DMEM with 10% FBS and plated ("passage 2") on either 35 mm dishes, E-well plates, or 96-well plates (Corning) as needed. Cells were grown for varying days in vitro (DIV) at passage 2 and then used for various experiments. Tissue culture dishes and plates were pre-coated with 100 µg/ml poly-L-lysine for 1 h in a humidified 5% $CO_2$ atmosphere at 37° C., and then allowed to air dry. After 2-3 weeks, cultures were treated with 0.25% trypsin-EDTA (Invitrogen) to yield a single cell suspension and washed 5 times with DMEM (Invitrogen). Cell density was measured with the Vi-CELL cell counter (Beckman Coulter) or hemocytometer by the trypan-blue exclusion method. For simplicity, cells are referred to as "172.9 cells."

As noted above, 172.9 cells were plated in poly-D-lysine coated white 96-well plates (Becton Dickinson) for luciferase activity assay, or poly-D-lysine coated black-wall/clear-bottom 96-well plates (Beckton Dickinson) for cell-based ELISA assay. Under these conditions, the cell cultures typically consist of >95% GFAP-positive cells.

Pilot experiments optimized cell density, time in culture, and assay conditions. Signals in the luciferase assay consistently yielded values that were 4000-fold above background (established from non-transgenic mice). Signals in the ELISA assay were 10-fold above background (i.e. no cells, or astrocytes derived from GFAP null mice).

Each of the four screens is described below.

1. Primary Screen

To identify compounds that decrease GFAP promoter activity and/or reduce GFAP protein levels, the Known Bioactive Library (KBA01) prepared by the UW-Small Molecule Screening Facility (University of Wisconsin, Madison) was screened. The KBA01 library consists of 2880 compounds comprising the combined collections of two original small molecule libraries: the Prestwick Chemical Library® and the Spectrum collection. Most compounds in the Prestwick Chemical Library® are marketed drugs with known safety and bioactivity in humans. The Spectrum collection provided a wide range of biological activities and structural diversity of clinically useful drugs, natural products and non-drug chemicals. Compounds in both libraries are available as 10 mM stocks in DMSO. These stocks were further diluted to 1 mM in DMSO for long-term storage. For simplicity of presentation, all members of these two libraries will be referred to as "compounds."

For the primary and secondary screens, cells were plated in 96-well plates at a density of 5000 cells/well in 100 μmedia with the Biomek FX liquid handler (Beckman Coulter) at the Small Molecule Screening Facility (University of Wisconsin-Madison). Cells were maintained in DMEM supplemented with 10% (v/v) fetal bovine serum, 100 U/ml penicillin, 100 μg/ml streptomycin.

For both the primary and secondary screens, 80 compounds were screened per 96-well plate. Two columns (8 wells each) were reserved as controls. In the luciferase assay, these two columns served as positive controls (i.e. maximum GFAP signal), consisting of astrocytes grown in the absence of any compound. In pilot studies it was found that background in the luciferase assay (either from empty wells, or wells containing non-transgenic astrocytes), was essentially zero, so no negative control wells were deemed necessary. In the cell-based ELISA, one column served as positive controls (again, astrocytes grown in the absence of compounds), and one column as negative controls (no astrocytes). Pilot studies using cells from GFAP-null mice showed that approximately 10% of the signal obtained from wells with wild type astrocytes represented background. For simplicity in the primary screen empty wells were used to define signal from background.

Treatment with compounds commenced at 24 hours after dispersion into the 96-well plates (passage 2), and continued for 48 hrs, at a single concentration of 10 μM in medium with 1% DMSO. The final concentration of DMSO used after dilution for the primary screen (1% in DMEM) had no effect on the luciferase or cell-based ELISA results.

a. hGFAP Luciferase Expression Assay

For detection of luciferase activity, the manufacturer's protocol (E 2610, Promega) was modified and optimized to give reliable signal intensities in a 96-well format. Briefly, 172.9 cells were plated on poly-L coated white 96-well plates at a density of 5000 cells per well, in 100 μl DMEM with 10% FBS. At twenty-four hours, cells were exposed to the different compounds at a final concentration of 10 μM (diluted from a 50 mM stock) prepared in new medium (DMEM with 10% FBS). Cells were exposed to the compound for 48 hours. After exposure to compounds, luciferase activity in the primary and secondary screenings was determined by adding 30 μl of Bright-Glo™ reagent (Promega) to the 100 μl of media and cells of each well in the white 96-well plates with the Biomek® FX liquid handler (Beckman Coulter). After incubation for 1 minute at room temperature, signals were measured with the Safire 2 plate reader using Magellan™ software (Tecan). Other specific methods and equipment are known in the art and can be used to measure luciferase expression levels. This assay method is termed the "hGFAP promoter luciferase activity assay." A reduction in luciferase expression as determined by this assay is termed "hGFAP promoter luciferase reduction." For some assays that were aimed at confirming results of the initial screens, the same amount of Bright-Glo™ reagent was applied to each well in 96-well plates and signals were detected with the GloRunner™ Microplate Luminometer (Turner Biosystems) using the Dual-Glo® luciferase assay according to the manufacturer's recommendations (E1910, Promega).

b. Cell Based ELISA for Quantitation of GFAP

For the primary and secondary screens, 5000 172.9 cells were plated per well in poly-D-lysine coated clear-bottom/black-wall 96-well plates (Becton Dickinson), in 100 μl DMEM with 10% FBS. At twenty-four hours, cells were exposed to the compounds for 48 hours (final concentration of the compound was 10 μM prepared in new medium (DMEM with 10% FBS; 100 μl per well). After 48 hours of exposure to the compound, cells were fixed with 100% methanol for 20 minutes at RT. Cells were then rinsed five times with 0.1% Triton X-100/PBS for 5 minutes per wash. After blocking with LI-COR Odyssey blocking Buffer® (LI-COR Biosciences) at RT for 1.5 hrs, cells were incubated with rabbit anti-GFAP antibody (1:5000, DAKO) diluted in Odyssey blocking Buffer® overnight at 4° C. Plates were rinsed five times with 0.1% Tween-20/PBS for 5 min per wash and incubated with IRDye™ 800CW goat anti-rabbit (1:800, LI-COR Biosciences) diluted in Odyssey blocking Buffer® containing 0.5% Tween-20 for 1 hr at RT. Cells were washed five times for five minutes each with 0.1% Tween-20/PBS. Plates were scanned with the Odyssey® Infrared Imaging System (LI-COR Biosciences) using the 800 nm channel. Liquid handling was performed using the μFill reagent dispenser (Bio-Tek Instruments, Inc.). This assay method is termed the "cell-based GFAP protein level assay." A reduction in GFAP protein level as determined by this assay is termed "cell-based GFAP protein level reduction."

c. Results

For the results of luciferase assays, heat maps (Java Treeview) were generated to indicate the percent reduction in GFAP promoter activity. Percent reduction was displayed by decrease in luminescent signals of compound treated wells compared to untreated controls with the Java Treeview 1.1.1 software (General Public License).

A total of 72 plates was used to conduct the primary screen. Background in the luciferase assay was so low (<0.1%) that no correction was applied. Signals in the cell-based ELISA were corrected for background as determined in wells with medium only. Z'-factors were calculated for each plate in the screen, using the following formula from Zhang et al. (1999) (standard deviation (σ) and mean (μ) signals for positive (pos) and negative (neg) controls):

$$z' = 1 - \frac{(3\sigma_{pos} + 3\sigma_{neg})}{|\mu_{pos} - \mu_{neg}|}$$

The Z'-factors averaged 0.64 for the luciferase assay and 0.63 for the cell-based ELISA, well above the recommended minimum of 0.5. Aggregate results, and examples of plates for both assays, are shown in FIG. 4. Our criterion for a hit was a 50% or greater reduction in the luciferase or GFAP protein signals after exposure to compounds.

Overall, the primary screen identified 356 (12.4%) compounds that qualified as hits (see Table 1 below and FIG. 4). Table 1 shows a summary of results from a primary screen of the 2880 compounds in both the hGFAP promoter luciferase activity assay and the cell-based GFAP protein level assay. No corrections were made for potential effects on cell survival in the primary screen.

TABLE 1

| | Primary Screen of 2880 Compounds | | |
|---|---|---|---|
| library | % reduction | hGFAP promoter luciferase activity assay compounds n (%) | cell-based GFAP protein level assay compounds n (%) |
| Prestwick | <50 | 772 | 856 |
| | 50-75 | 37 (4.2%) | 20 (2.3%) |
| | 75-90 | 30 (3.4%) | 4 (0.5%) |
| | 90-100 | 41 (4.6%) | 0 |
| Spectrum | <50 | 1752 | 1964 |
| | 50-75 | 105 (5.3%) | 33 (1.7%) |

TABLE 1-continued

Primary Screen of 2880 Compounds

| library | % reduction | hGFAP promoter luciferase activity assay compounds n (%) | cell-based GFAP protein level assay compounds n (%) |
|---|---|---|---|
| | 75-90 | 52 (2.6%) | 3 (0.1%) |
| | 90-100 | 91 (4.5%) | 0 |

2. Secondary Screen

To determine whether any of the hits identified in the first round of screening reflected non-specific toxicity, 356 compounds noted above plus an additional 44 compounds (for a total of 400) were subjected to repeat cell treatments and hGFAP promoter luciferase activity assay and the cell-based GFAP protein level assay, and to measured cell viability. Criterion for acceptable viability was >70% survival.

In the secondary screen, cells were plated in a 96-well plate as described above for the primary screen. Compounds were added at 10 μM beginning 24 hours after plating; cells were again exposed to a given compound for 48 hours. Compounds that resulted in >70% cell survival were then tested in a tertiary screen.

Cell viability was determined as follows. After exposure to each compound (duplicate wells per compound), 50 μl of CellTiter-Glo Luminescent Cell Viability Assay reagent (G7571, Promega) was added to the 100 μl of media present in each well, and the luminescent signal (reflecting intracellular ATP level) was detected with either a Victor 3-V plate reader (Perkin Elmer) or GloRunner Microplate Luminometer (Turner Biosystems). Cell viability was expressed as a percent of non-treated control cells.

a. Results

Under these conditions, 14 compounds reduced the luciferase signals by >50% without causing toxicity, while 21 compounds reduced the ELISA signals by >50% without causing toxicity (Table 2). The number of compounds achieving >50% reduction in GFAP signal is shown on the left, and the number of those compounds that also allowed >70% cell survival is shown on the right. Six compounds (diaziquone, EGCDG, mundoserone, irigenol, amlodipine besylate, 7-desacetoxy-6,7-dehydrogedunin) exhibited significant suppression in both the promoter and protein assays. None of these six compounds was cytotoxic.

TABLE 2

Secondary Screen of 400 Compounds

| assay | >50% reduction | >70% viability |
|---|---|---|
| promoter screen | 30 (4%) | 14 (2%) |
| protein screen | 42 (7%) | 21 (3.4%) |

3. Tertiary Screen

To further validate these results, dose-response curves for 39 compounds were performed (35 compounds selected from the secondary screen plus 4 additional compounds), using independently purchased stocks. Some compounds were unavailable outside of the library collections, and could not be further tested. The luciferase, cell-based ELISA, and cell viability assays were repeated after exposures for 48 hours to 0-20 μM of each compound.

A dose-response curve was created for each compound (0.1, 0.5, 1, 5, 10, 15, 20 μM) using 48 hr exposures. The MTDcc ("maximum tolerated dose—cell culture") indicates the highest concentration that retained at least 70% cell viability. Each compound and concentration was analyzed in quadruplicate wells. EGCDG: epigallocatechin 3,5-digallate; NPPB: 5-nitro-2-phenylproplyaminobenzoic acid. As used herein, MTDcc refers to the MTD as determined by this assay under the above conditions.

a. Results

Of these 39 compounds, more than half resulted in sufficiently significant levels of inhibition to warrant further study. At the MTDcc (see below), eight of the compounds again achieved >50% reductions in GFAP promoter activity, although none of the compounds caused >50% reductions in GFAP protein. Table 3 provides the results of these assays for the 39 compounds, ranked according to percent reduction in GFAP promoter activity. At the highest doses, some compounds displayed cytotoxicity. The maximum tolerable dose for cell culture ("MTDcc") is presented as the highest concentration of drug showing acceptable cell viability (i.e. >70%).

TABLE 3

Results from tertiary screen of 39 compounds

| | | % GFAP reductions | |
|---|---|---|---|
| Compounds | MTDcc (μM) | luciferace expression from hGFAP promoter | mGFAP protein via ELISA |
| diaziquone | >20 | 86 | 9.5 |
| clomipramine | 12.5 | 66 | 20.6 |
| chrysophanol | 12.5 | 66 | 18.6 |
| amitriptyline | >20 | 63 | 12.2 |
| chlorprothixene | 17.5 | 60 | −3.6 |
| EGCDG | 17.5 | 57 | 4.5 |
| tamoxifen citrate | 7.5 | 52 | 21.6 |
| mundoserone | >20 | 50 | 1.6 |
| amlodipine | 12.5 | 44 | 12.7 |
| embelin | 7.5 | 37 | 10.8 |
| thioridazine | 5 | 37 | 17.7 |
| ritanserin | 12.5 | 29 | 9.6 |
| irigenol | >20 | 28 | 1.8 |
| fluccinonide | >20 | 28 | −2.2 |
| hexetidine | >20 | 26 | 6.4 |
| estradiol benzoate | >20 | 26 | −2.8 |
| ketotifen | >20 | 25 | 8.6 |
| clobetasol propionate | >20 | 25 | −7.6 |
| colecalciferol | >20 | 24 | −4.9 |
| fluphenazine | 7.5 | 23 | −6.7 |
| pyrogallin | >20 | 22 | 3.3 |
| kanamycin | >20 | 22 | 11.3 |
| azinphos methyl | >20 | 18 | 4.7 |
| 4-acetamidophenyl salicylate | >20 | 17 | 8.6 |
| oxotremorine | >20 | 16 | 2.7 |
| ritodrine | >20 | 16 | 5.2 |
| 5-nitro-2-phenylpropyl-aminobenzoic acid (NPPB) | >20 | 16 | 0.4 |
| chloramphenicol | >20 | 16 | 0.9 |
| terfenadine | 2.5 | 14 | 11.2 |
| phosphocreatine | >20 | 13 | 3.8 |
| betulinic acid | >20 | 13 | 6.3 |
| methylnorlichexanthone | >20 | 10 | 0.6 |
| coumophos | >20 | 10 | 0.4 |
| swietenolide-3-acetate | >20 | 8 | 0.7 |
| decarbazine | >20 | 7 | 2.4 |
| veratic acid | >20 | 6 | −0.8 |
| pantothenic acid | >20 | 6 | −3.5 |
| neamine | >20 | 5 | −0.8 |

One of these compounds (clomipramine) was tested in a mouse model (see section B below). Betulinic acid derivatives were evaluated in 172.9 cells and in R263H cells (described below in section 5).

4. Quaternary Screen

To evaluate the possibility that the observed reductions in GFAP promoter or protein depend on length of treatment, a dose-response for each compound with 10 days of exposure was performed. Compounds were tested at eight different concentrations ranging from 0-20 µM. In addition, GFAP protein levels were measured using a sandwich ELISA, which has greater sensitivity and is more accurate than the cell-based ELISA used in the primary screens.

a. Sandwich ELISA for Quantitation of GFAP Protein

Cells grown in poly-D-lysine coated clear-bottom 96-well plates (Becton Dickinson) were washed 3× in PBS and then lysed at RT in 1% SDS/PBS, 2 mM EDTA, and 50 mM Tris, pH 7.5, supplemented with Complete Proteinase Inhibitor Cocktail (Roche Applied Biosciences, cat. #11836145001). The extracts were harvested from each well and the total GFAP content of each well was measured by a sandwich ELISA as described below. Briefly, separate microtiter plates were coated with SMI-26 anti-GFAP mouse monoclonal antibody cocktail (1:1000, Covance, diluted in PBS) overnight at 4° C., rinsed 3 times in PBS, and then blocked with Blotto (5% nonfat milk/PBS) for 2 h at RT. Samples from the astrocyte cell lysate (20 µl per well) were loaded onto the plates and brought up to 100 µl with 0.5% Triton X-100/PBS (a buffer used for subsequent antibody incubations and rinses), and incubated with a rabbit polyclonal anti-GFAP antibody (1:5000, DAKO) overnight at 4° C. The plates were rinsed three times and then incubated with HRP-conjugated goat anti-rabbit IgG (1:30,000, Sigma) for 2 h at RT. After three final rinses, peroxidase activity was detected using the Super Signal Femto maximum Sensitivity Substrate (Pierce) with a GloRunner microplate luminometer (Turner Biosystems). The GFAP content in the samples was determined from a standard curve generated using serial dilutions of purified GFAP (Research Diagnostics). The ELISA signals were normalized to total protein concentration of comparable wells from replicate 96-well plates, lysed in 1% SDS-proteinase K, using the BCA Protein Assay Kit (Thermo Scientific).

b. Results

Figure 5:
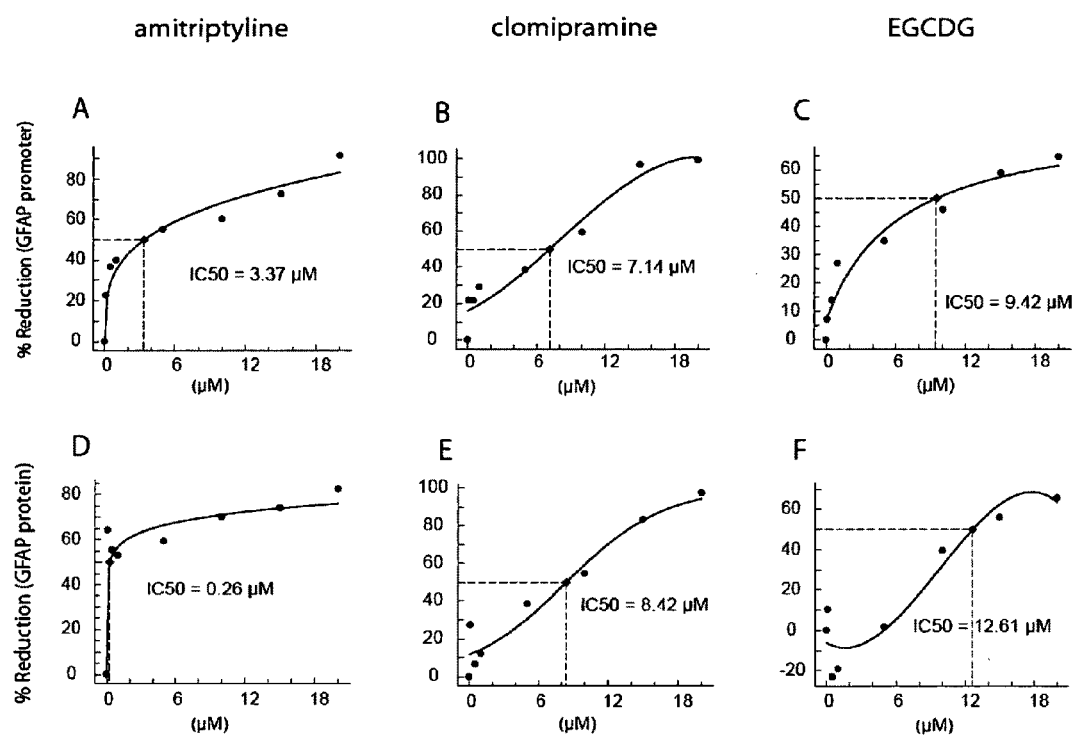
FIGS. 5A-F show dose-response curves for amitriptyline (A and D), clomipramine (B and E), and epigallocatechin 3,5-digallate (EGCDG) (C and F) evaluated for percent reduction in hGFAP promoter (top row) or protein levels (bottom row). Astrocytes from hGFAP-luciferase transgenic mice were exposed to a each compound at 0-20 µM for 10 days. IC50's were calculated from fitted curves. Each point represents the mean of triplicate wells.

Cytotoxicity was observed between 15-20 µM for every compound tested (compounds were tested in triplicate wells at eight different concentrations ranging from 0-20 µM). However, consistent reductions in luciferase activity and GFAP protein levels with acceptable cell viability were observed in cells exposed to amitriptyline, clomipramine and epigallocatechin 3,5-digallate (EGCDG) (FIG. 5). IC50's (the half maximal inhibitory concentrations) were typically in the low micromolar range, and little or no activity was observed at nanomolar concentrations. Potency of drugs referred to as IC50 was calculated by generating percent reduction curves fitted for the plots with the XLfit Software (IDBS). For comparing two groups, statistical significance was considered if $p<0.05$ by t-test or two-way ANOVA (Prism 3.02, GraphPad).

Figure 8:
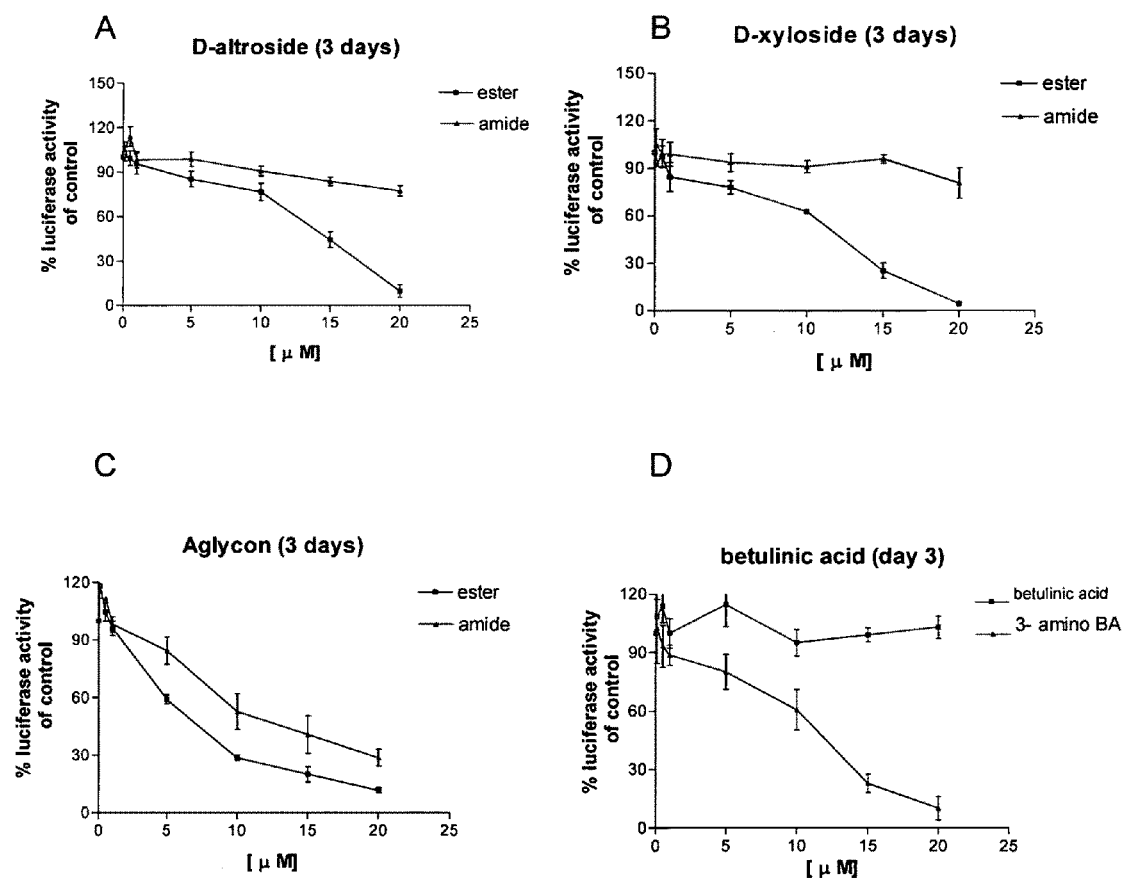
FIGS. 8A-D are graphs showing the effects of betulinic acid and betulinic acid derivatives on luciferase expression driven by the hGFAP promoter in 172.9 cells after 3 days of treatment. In the graphs, ester and amide forms of various compounds are paired for comparison.
Figure 9A:
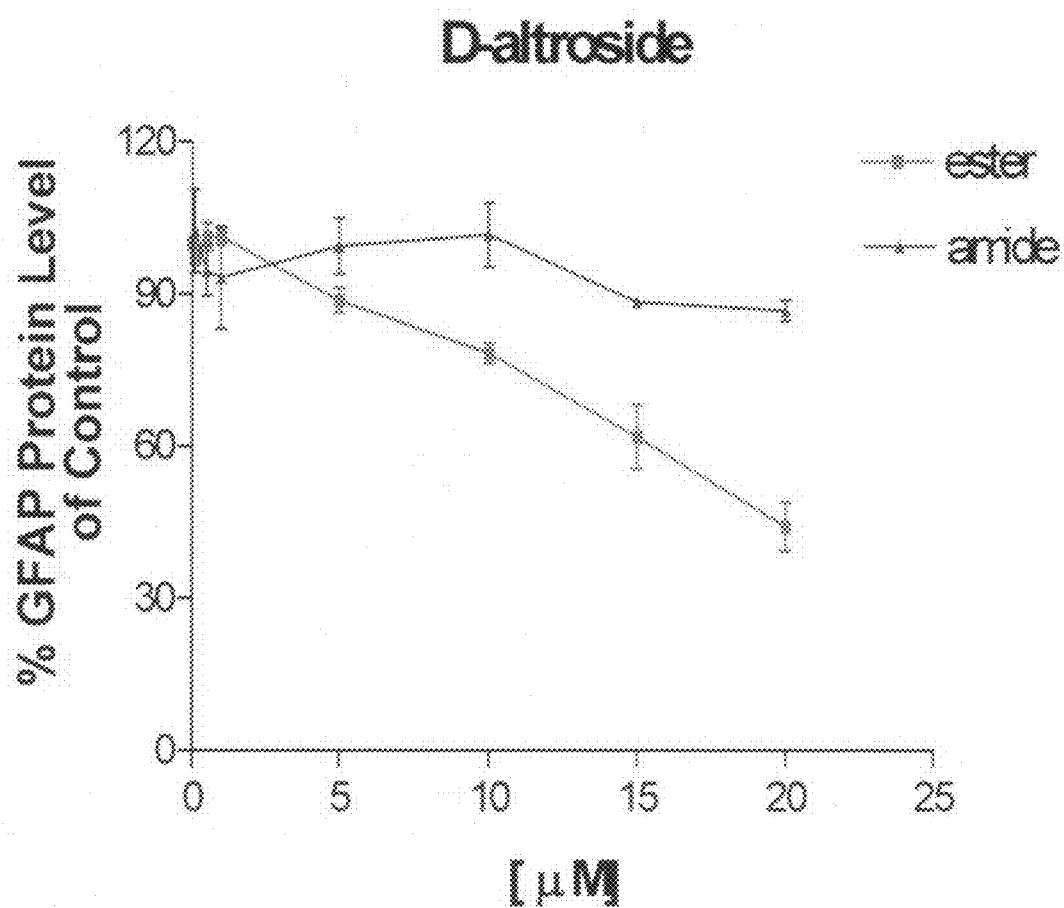
FIG. 9A-D are graphs showing the effects of betulinic acid and betulinic acid derivatives on mGFAP protein levels in 172.9 cells after 7 days of treatment. In the graphs, ester and amide forms of various compounds are paired for comparison. The arrow in FIG. 9C indicates the ester form of aglycone has minimal effect on mGFAP protein levels, yet decreased luciferase expression driven by the hGFAP promoter (see FIG. 8C).
Figure 9B:
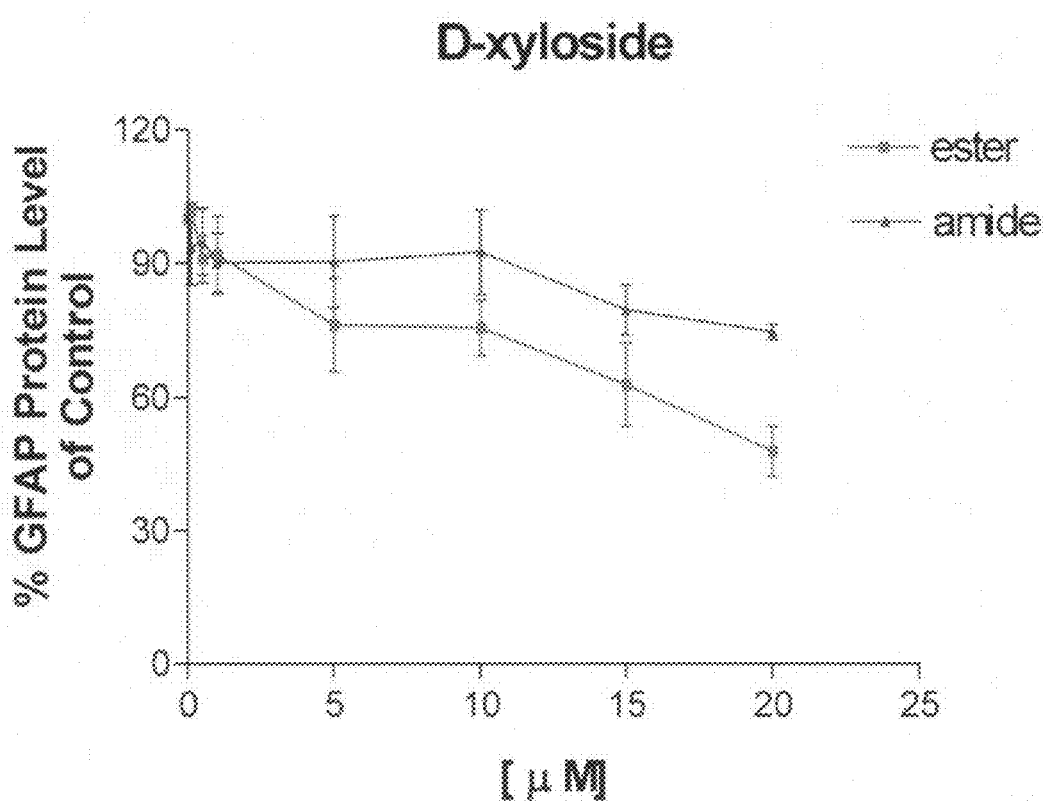
Figure 9C:
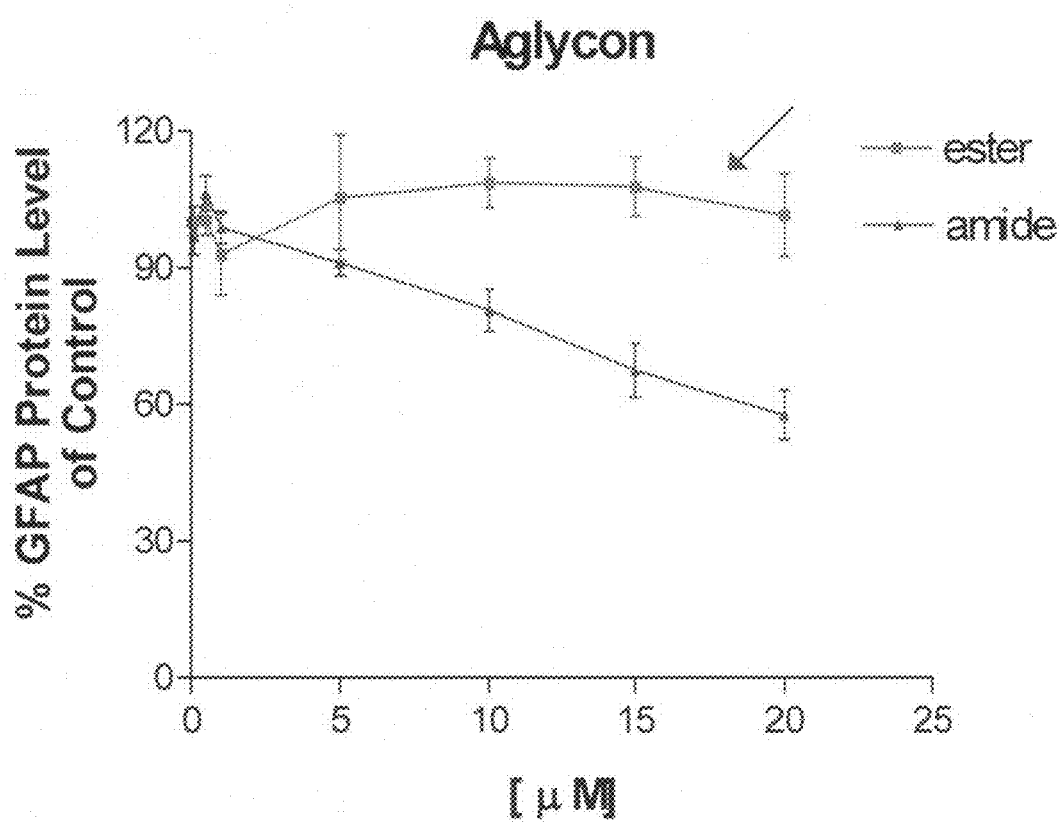
Figure 9D:
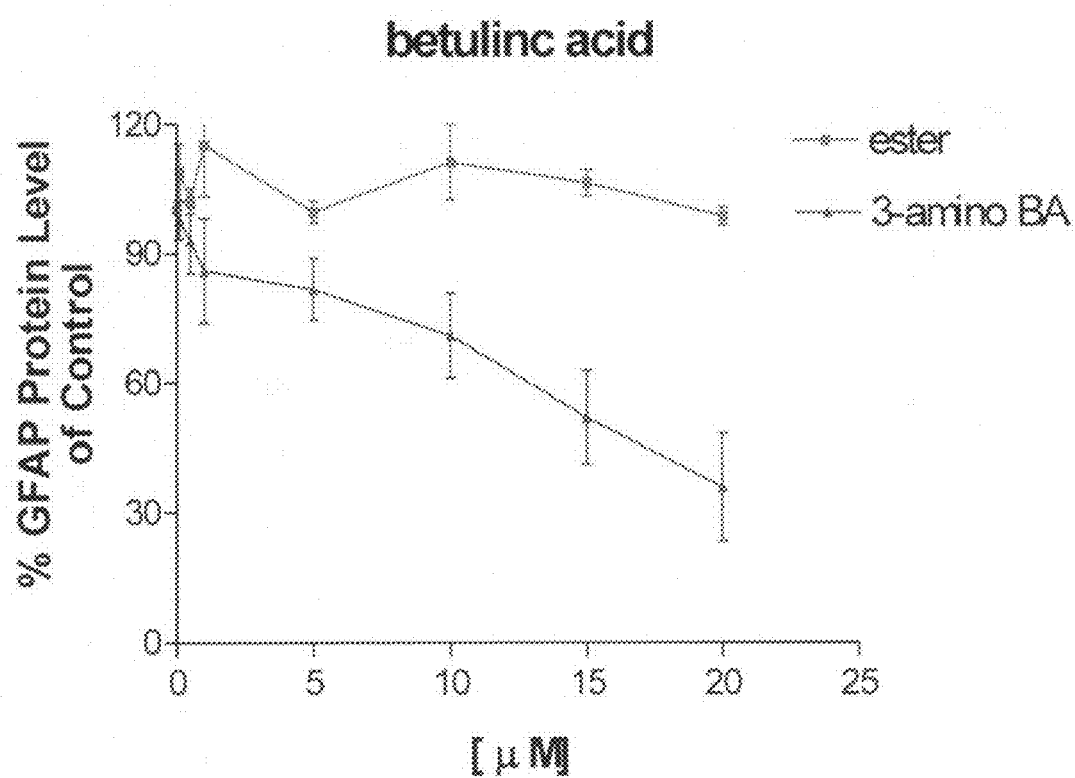

5. Test of Betulinic Acid and Betulinic Acid Derivatives on 172.9 and R236H Cells 172.9 cells were used to test the effects of betulinic acid and betulinic acid derivatives on GFAP promoter activity and GFAP protein levels. Experiments were performed as previously described. Each of eight compounds (D-altroside (ester); D-altroside (amide); D-xyloside (ester); D-xyloside (amide); aglycon (ester); aglycon (amide); betulinic acid; 3-amino betulinic acid) was tested at a concentration of 0 µM, 0.1 µM, 0.5 µM, 1 µM, 5 µM, 10 µM, 15 µM, and 20 µM. Luciferase activity was measured after 1 day of treatment (data not shown) with a given compound and after 3 days of treatment with a given compound, while GFAP protein levels were measured after 7 days of treatment with a given compound by ELISA. Toxicity of the compounds was also evaluated. While aglycon (ester) and 3-amino betulinic acid appeared to have a slightly toxic effect at high concentrations (e.g., in the 20 µM range, see FIG. 10), the other six compounds appeared to be non-toxic to the 172.9 cells at the concentrations and times of exposure tested. The compounds tested, the effect on GFAP promoter activity after 3-days of treatment and the effects on GFAP protein levels after 7 days of treatment are shown in FIGS. 8 and 9.

For D-altroside and D-xyloside, the ester form resulted in a more dramatic decrease in GFAP promoter activity than the amide form. For aglcyon, both the ester and amid forms resulted in similar levels of decrease in GFAP promoter activity. For betulinic acid, the 3-amino form resulted in a decrease in GFAP promoter activity. With respect to protein levels, the ester form of D-altroside and D-xyloside reduced GFAP protein levels more than the amide form. For aglycon, the amide form reduced GFAP protein levels more than the ester form, and for betulinic acid, the 3-amino form reduced GFAP protein levels more than the ester form.

Figure 10:
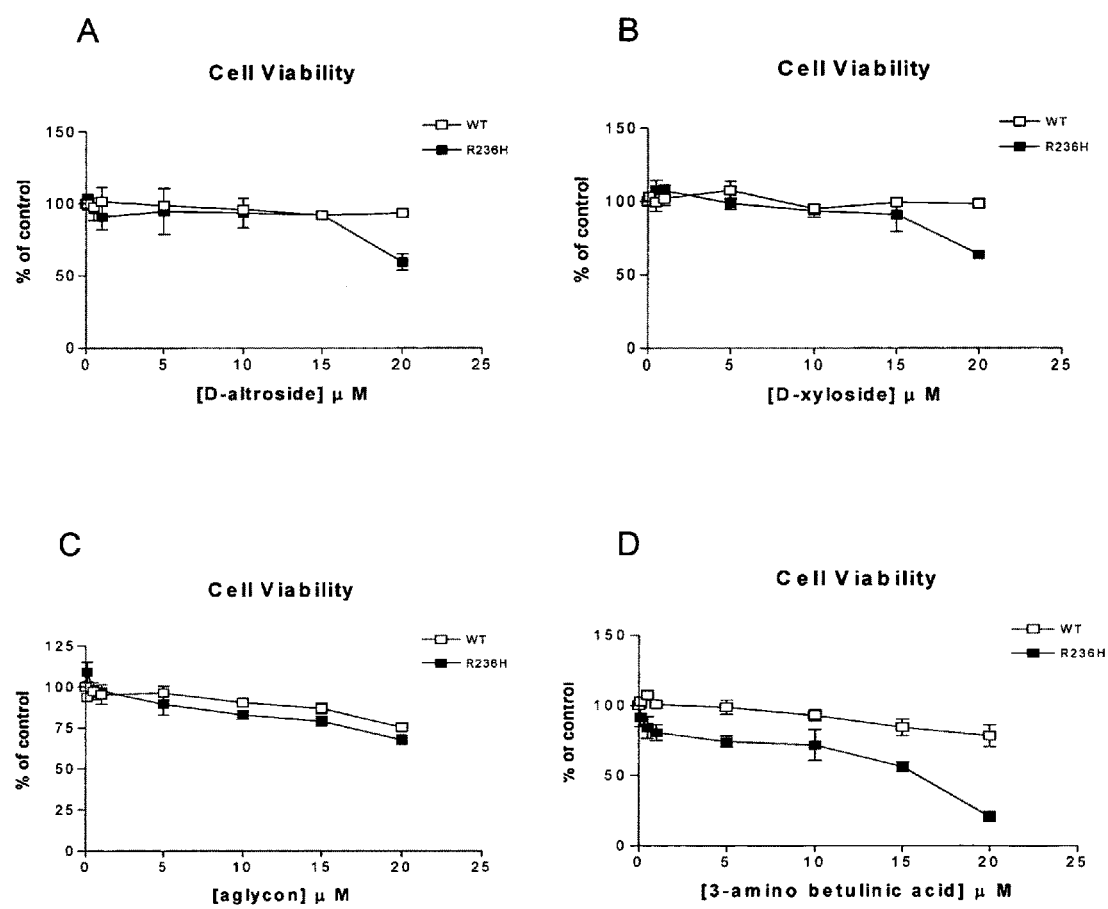
FIGS. 10A-D are graphs comparing the cell viability of 172.9 cells and R236H cells after exposure to four different betulinic acid derivatives for 3 days.
Figure 11:
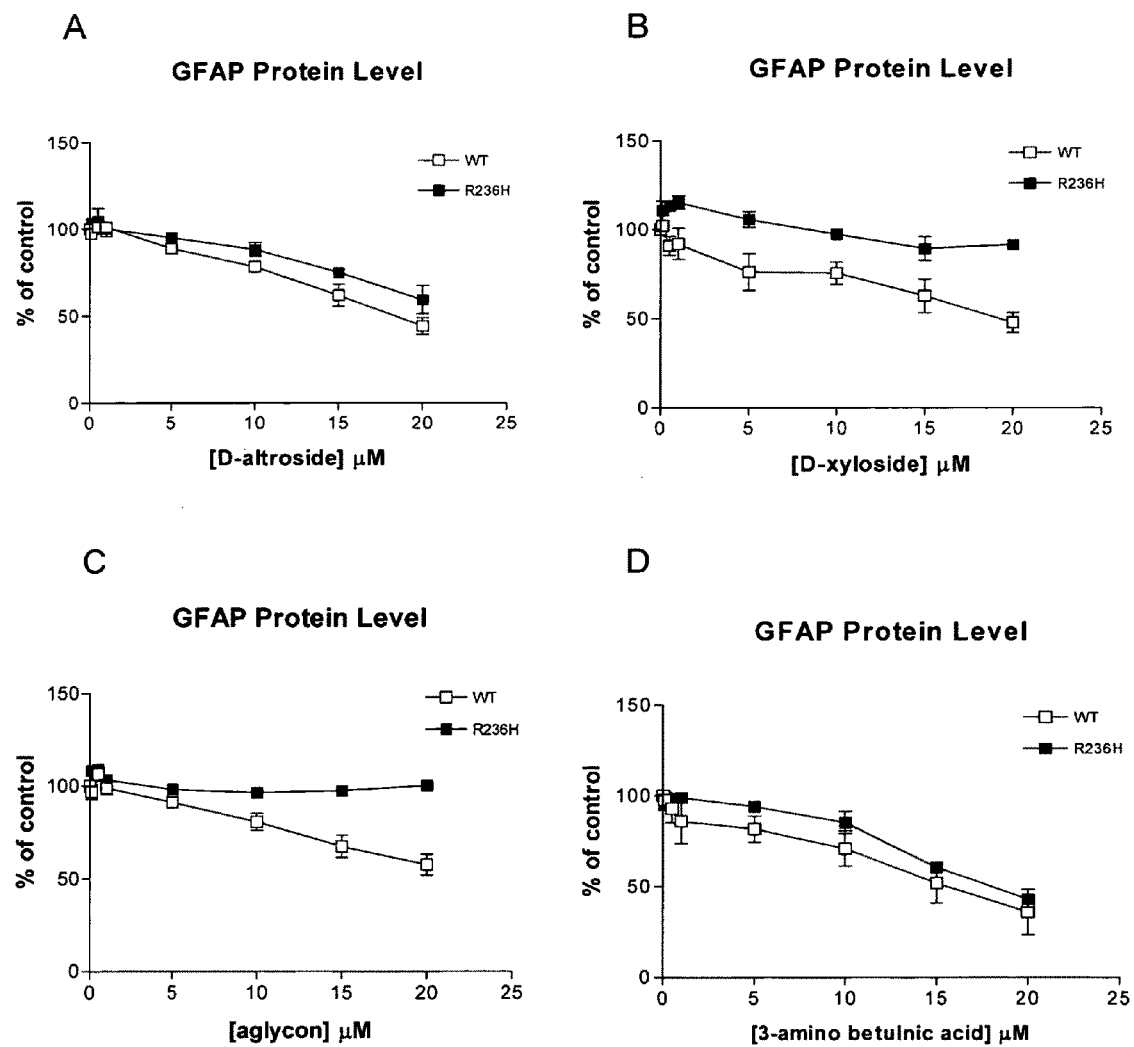
FIGS. 11A-D are graphs comparing the effect of four different betulinic acid derivatives on mGFAP protein levels in 172.9 cells and R236H cells after 7 days of treatment.

Four of these compounds, D-altroside (ester), D-xyloside (ester), aglycon (amide) and 3-amino betulinic acid, were also tested in primary astrocytes grown from mice expressing the equivalent of one of the point mutant forms of GFAP found in Alexander disease patients, the R2369H mutation; the equivalent mutation in mouse is the R236H mutation. These mutant mouse cells are termed "R236H cells." Experiments were performed as previously described. As shown in FIG. 10, some of the compounds appear to have a slightly more toxic effect at higher concentrations on the R263H cells than on the 172.9 cells. The effect of these four compounds on GFAP protein levels in the 172.9 cells and the R263H cells is shown in FIG. 11.

B. In Vivo Assays

1. Construction of Dual Transgenic Reporter Mice as a Tool for Monitoring Expression of GFAP (FVB-Tg (GFAP-luc,GAPDH-rluc)172.9MES/J Mouse Strain To facilitate study of the transcriptional regulation of GFAP expression under dynamic conditions, transgenic mice expressing both firefly and Renilla luciferase reporter genes were generated. The transgenes were constructed as follows. Transgenes expressing firefly luciferase regulated by the GFAP promoter (GFAP-fLuc), utilized the 2.2 kb human GFAP promoter derived from the GFAP-lacZ transgene described by Brenner et al., *J. Neuroscience*, 14:1030-1037 (1994). The GFAP promoter fragment (−2163 to +47) was subcloned into the Bgl II site in the pGL-3 basic vector (Promega, Madison, Wis., USA) containing the firefly luciferase gene. In parallel, a transgene expressing the Renilla luciferase regulated by the human glyceraldehyde 3-phosphate dehydrogenase (GAPDH) promoter (Alexander et al., *Proc. Natl. Acad. Sci. USA*, 85:5092-5096 (1988) was prepared (GAPDH-RLuc), using a 0.5 kb fragment (−488 to +21) isolated from genomic DNA obtained from a human blood sample. Oligonucleotide primers were designed to generate XhoI and EcoRI restriction sites in the GAPDH PCR fragment (527 bp) that was amplified from the genomic DNA. The fragment was subcloned into XhoI and EcoRI restriction sites in the phRL-null vector (Promega) containing the Renilla luciferase gene. Both transgenes were sequenced to confirm correct orientation and sequence. Transgene fragments were isolated free of plasmid sequence and purified for microinjection using the Gene Clean Turbo kit (Q-Biogene, Carlsbad, Calif., USA).

The dual transgenic reporter mice (FVB-Tg(GFAP-luc, GAPDH-luc)172.9Mes/J mice (JR#9638)) were developed as follows. The two transgenes were co-injected at equimolar ratios into the pronuclei of fertilized eggs on either FVB/N or FB6F1 hybrid backgrounds, using a combined concentration of 3 ng/μL. Genotyping was performed by PCR on genomic DNA isolated from tail biopsies at weaning, using the following conditions: one cycle at 95° C. 3 min, 32 cycles of 95° C. 40 s, 58° C. 30 s, 72° C. 1 min and a final extension step at 72° C. for 5 min. The primers used for detection of the GFAP-fLuc transgene were 5'-TCTCTAAGGAAGTCGGG-GAAGC-3' (forward) and 5'-CAGCGGGAGCCACCTGAT-AGCCTT-3' (reverse), and for detection of the GAPDH-RLuc transgene were 5"-CTCCCATCGGGCCAATCTCAGTCC-3' (forward) and 5'-GCGTTTGCGTTGCTCGGGGTCGTA-3' (reverse). The predicted sizes for the PCR fragments are 403 bp for the GFAP-fLuc transgene, and 551 by for the GAPDH-RLuc transgene. Nine founder mice were identified that contained both transgenes, and were mated to FVB/N mice to establish lines. (The Tg172-9 line of mice has been donated to the Jackson Laboratory (West Grove, Pa., USA) for unrestricted distribution (stock #JR9638). The GAPDH (glyceraldehyde 3-phosphate dehydrogenase) promoter was used to monitor transcription of a housekeeping gene for signal normalization.

The GFAP-luciferase was highly expressed in brain compared to other tissues, whereas the GAPDH-luciferase was more widely expressed. Expression of the GFAP-luciferase was significantly higher in astrocyte-enriched compared to neuronal enriched primary cultures, suggesting that expression was limited to astrocytes. In brain extracts, normalization of the GFAP signal to the GAPDH signal reduced the assay variability compared to using the GFAP signal alone. The GFAP/GAPDH ratio correctly reflected the natural differences in GFAP levels that exist in FVB/N compared to FVBB6F1 mice, and also the up-regulation of GFAP that occurs following retinal degeneration in the FVB/N mice due to the rd mutation. Following kainic-acid induced seizures, changes in the GFAP/GAPDH luciferase ratio precede those in total GFAP protein. These results indicate that dual reporter transgenic mice are a useful tool for studying regulation of the GFAP promoter in vivo.

2. Transgenic Mice Expressing Mutant GFAP Protein

Figure 3:
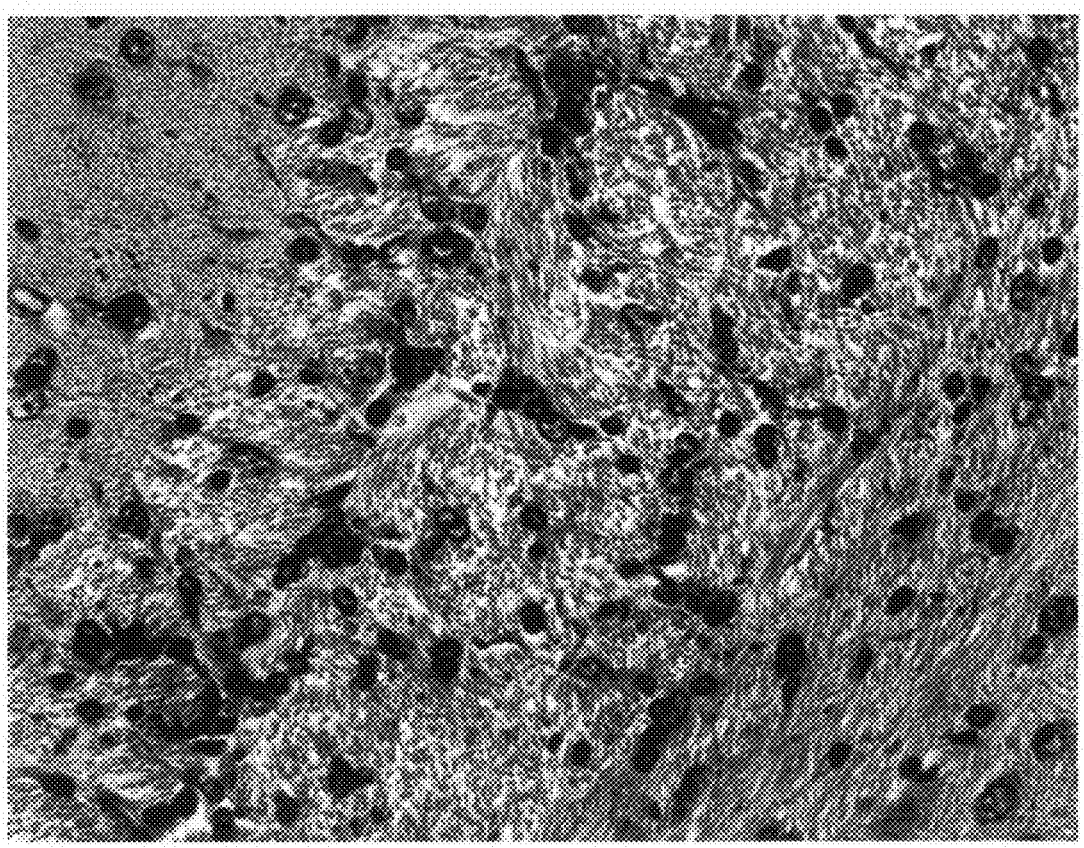
FIG. 3 a micrograph of cerebral white matter from mouse expressing R236H mutation in GFAP (equivalent mutation to the R239H in human GFAP).
Figure 4A:
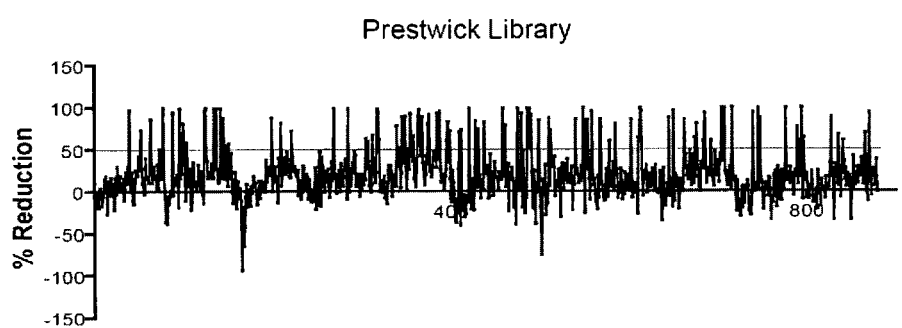
Figure 4B:
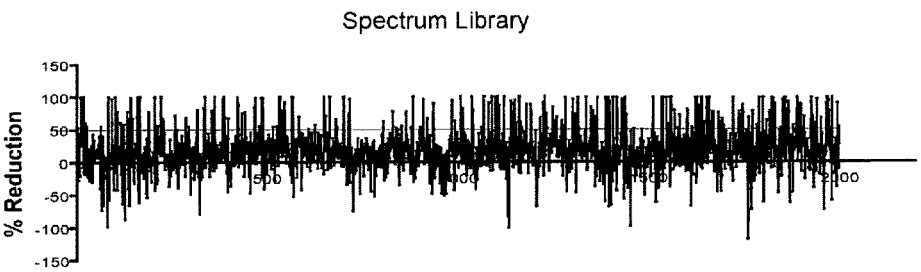
Figure 4C:
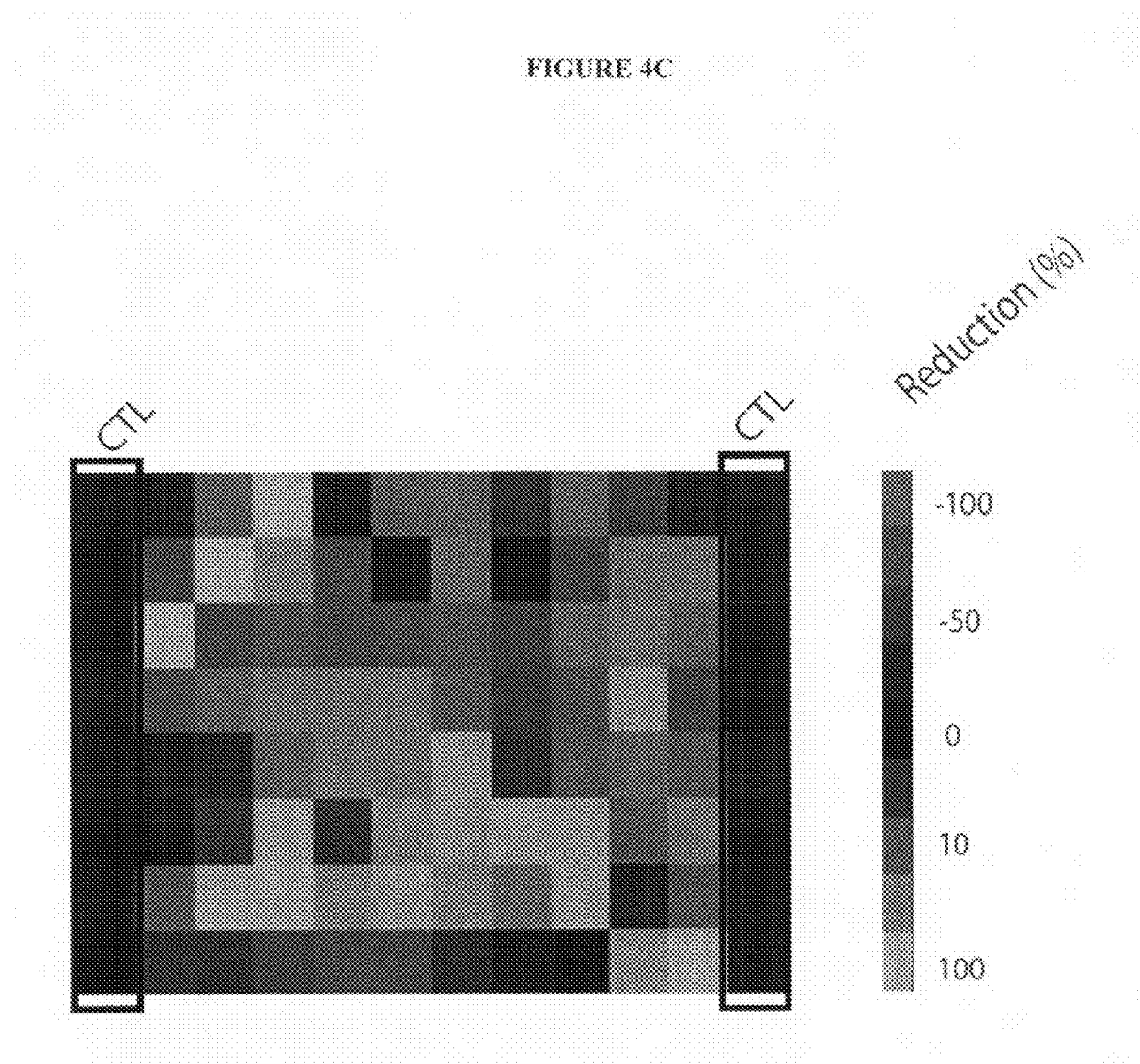
Figure 4D:
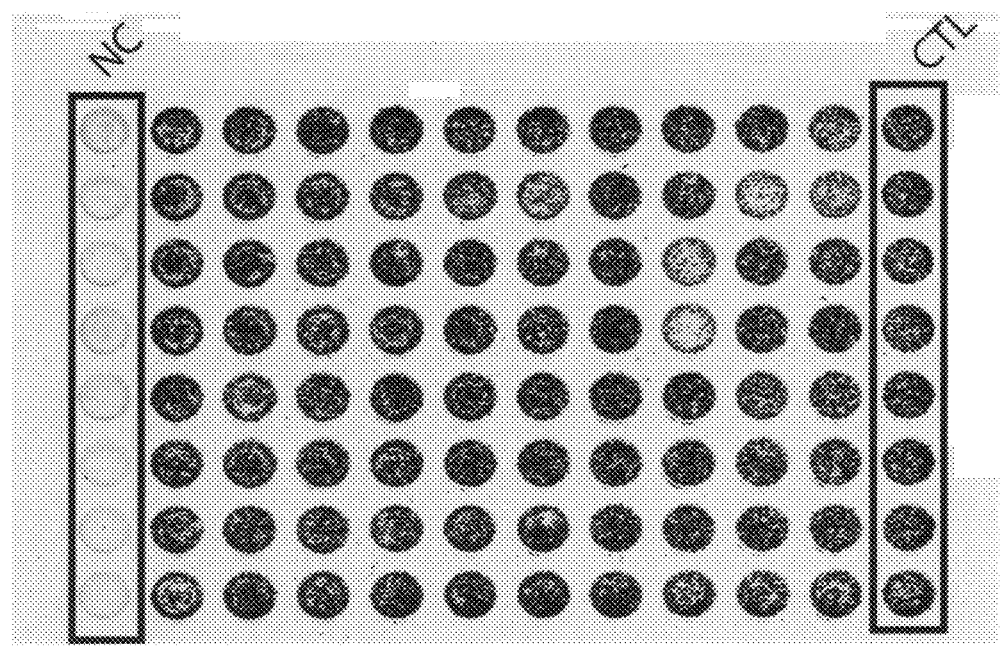
Figure 4F:
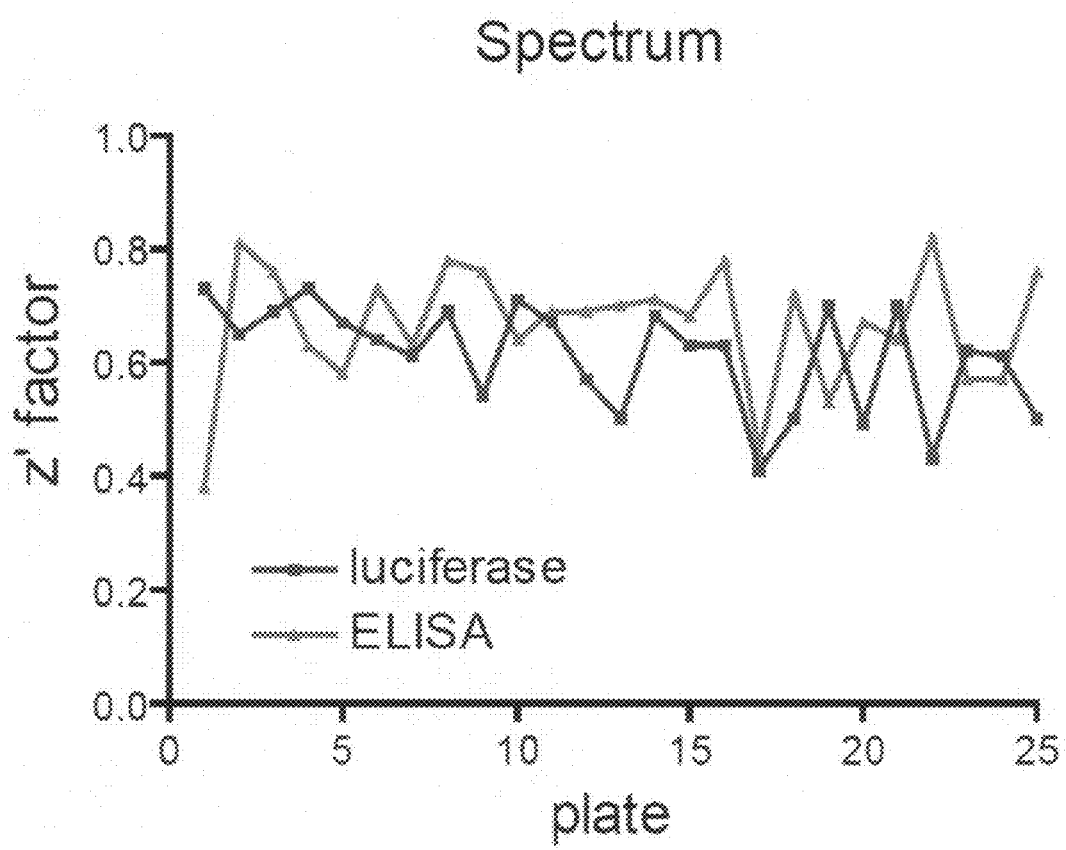

Another transgenic mouse model was developed as described in Hagemann et al., *J. Neourscience,* 26:11162-73 (2006), which includes a GFAP mutation equivalent to the R239H mutation found in human Alexander disease patients. FIG. 3 shows a histologic preparation of hippocampus from these mice. Note the prominent bright eosinophilic Rosenthal fibers in nearly all astrocytes, which supports the long-term value these mice can have as an in vivo test system for evaluating candidate drugs identified according to the methods described herein.

Figure 2:
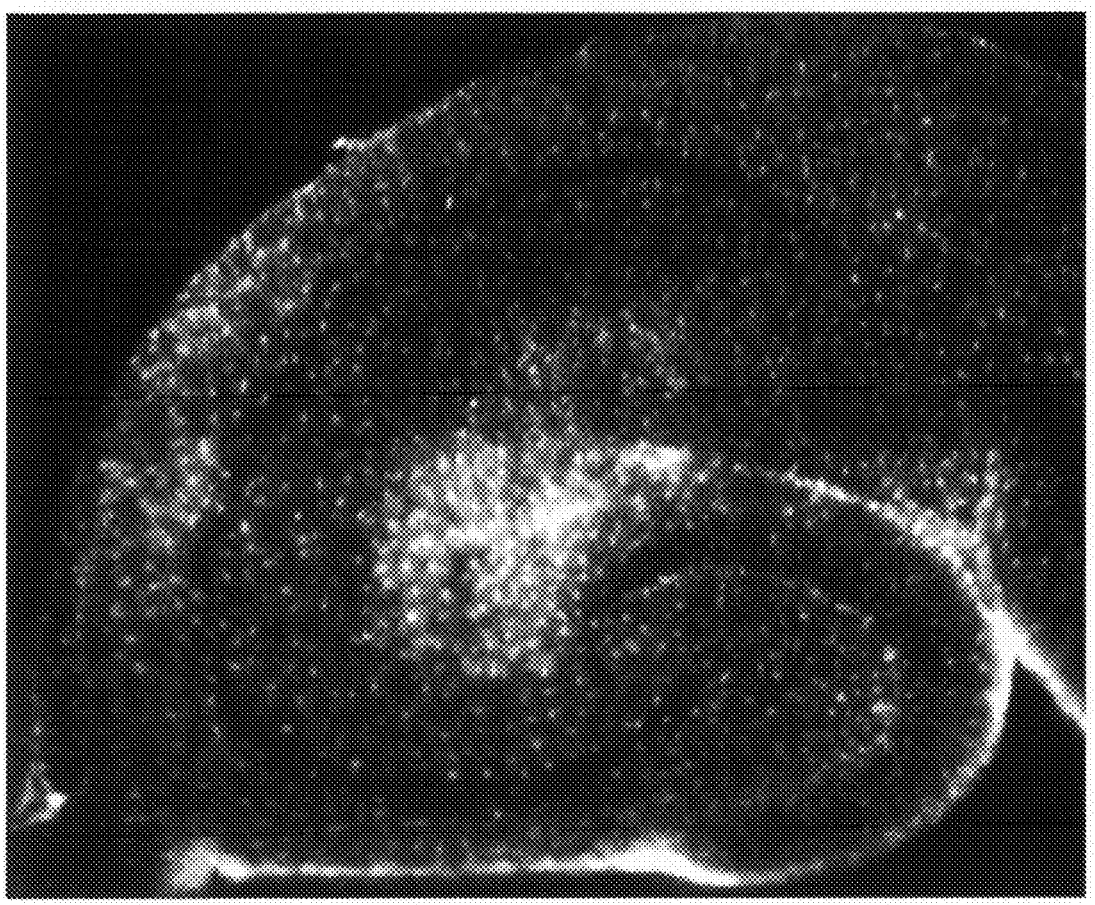
FIG. 2 is a micrograph of a hippocampal slice from adult hGFAP-gfp mouse, visualized by conventional FITC fluorescence microscopy. (hGFAP-gfp=human GFAP promoter; gfp=green fluorescent protein).

3. Transgenic Mice Expressing Green Fluorescent Protein Under Control of the GFAP Promoter FIG. 2 shows a live hippocampal slice from a transgenic mouse that express green fluorescent protein under the control of the human GFAP promoter (Zhuo et al., *Dev. Biol.* 187: 36-42 (1997)). As shown in the Figure, the promoter reliably directs astrocyte-specific expression in vivo.

4. In Vivo Assays Using Transgenic Mouse Strain FVB-Tg (GFAP-luc,GAPDH-rluc)172.9MES/J a. Acute Treatment of FVB-Tg (GFAP-luc,GAPDH-rluc) 172.9MES/J Mice with Clomipramine All animal studies were approved by the University of Wisconsin-Madison Institutional Animal Care and Use Committee.

Clomipramine was administered to live mice to determine whether GFAP promoter activity and protein levels in the brain would be affected. In acute dosing studies, adult mice from the TgGFAP/GAPDH-DualGlo line (Tg172.9, FVB/N background) (males, 3-4 months old) were treated once with 0-40 mg/kg clomipramine (Sigma, C7291) dissolved in water, via intra-peritoneal injections. At various times after injection, from 0-48 hours, brains were harvested for measurement of GFAP promoter activity using the Dual-Glo luciferase assay, and GFAP protein using a sandwich ELISA.

As shown in FIG. 6A, clomipramine treatment caused a transient reduction in promoter activity that peaked at 4-6 hours after injection. Promoter activity returned to normal by 24 hours. There were no changes in GFAP protein levels during this brief time period (data not shown).

Dual luciferase mice were also treated with varying doses of clomipramine (0-40 mg/kg, IP), and brains were collected at 4 hours after injection for measurement of GFAP promoter activity. As shown in FIG. 6B, a single injection of 40 mg/kg produced a 38% reduction in promoter activity, whereas doses of 5-20 mg/kg were without effect.

Clomipramine concentrations were determined in plasma and brain following single IP injections of the 40 mg/kg dose. Samples were collected from axillary arteries, and HPLC analysis was performed at the Pharmacokinetics Core Facility of the UW-Madison Comprehensive Cancer Center. Both plasma and brain levels peaked at 1 hour following injection (brain>plasma), in a range comparable to that found effective in cultured astrocytes (6 and 3 μM for brain and plasma, respectively).

b. Chronic Treatment of FVB-Tg (GFAP-luc,GAPDH-rluc)172.9MES/J Mice with Clomipramine In chronic dosing studies, adult mice of the same transgenic line described above (females, 2-4 month old at the onset of treatment) were given IP injections of clomipramine at 40 mg/kg, every other day for three weeks. Injections were given in the afternoon, between 3-5 PM. Controls were transgenic littermates injected with vehicle alone. At the end of the three week course of injections (and one day after the last injection), brains were harvested for analysis of GFAP promoter activity and protein levels as described above.

To achieve significant reductions of GFAP protein in vivo may require chronic treatments, given the slow turnover of this protein. However, pilot studies using daily injections of 40 mg/kg clomipramine resulted in weight loss after 2 weeks, and were discontinued. Instead, dual luciferase mice with 40 mg/kg clomipramine, intraperitoneally, every other day for 3 weeks. Controls were injected with vehicle alone. One day after the last injection, brains were harvested and assayed for both GFAP promoter activity and GFAP protein.

Figure 7:
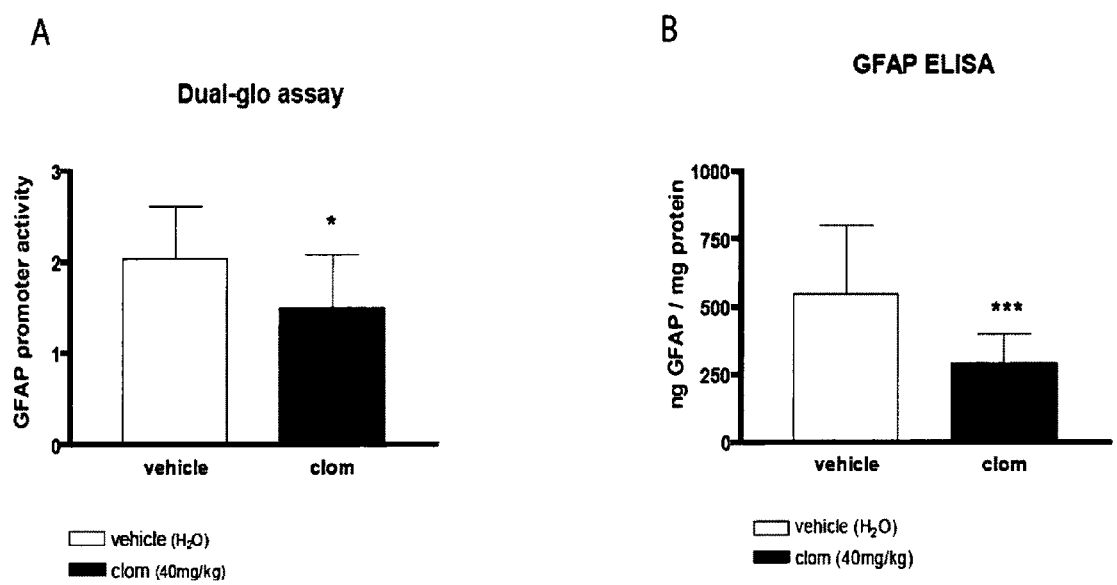
FIGS. 7A-B show the long-term effects of clomipramine on GFAP promoter activity and protein levels in vivo. Tg172.9 mice were injected with 40 mg/kg clomipramine in $H_2O$, intraperitoneally, every other day for 21 days (n=16). Another group of mice were injected with the same volume of vehicle alone (n=15). Brains were bisected sagittally with one half analyzed for GFAP promoter activity using the Dual-Glo assay, and the other half analyzed for GFAP protein using the sandwich ELISA.

Clomipramine-treated mice displayed a 26% reduction in GFAP promoter activity (FIG. 7A, *p<0.05, unpaired t-test). These same mice displayed a 57% reduction in GFAP protein (FIG. 7B, *** p<0.001, unpaired t-test). There was no significant change in the activity from the housekeeping GAPDH promoter in the same mice (data not shown).

Clomipramine is currently approved by the FDA for the treatment of obsessive-compulsive disorder, but a number of off-label uses exist including enuresis, narcolepsy/cataplexy, premature ejaculation, depression, and anxiety. Clomipramine can have numerous potential side effects, including a spectrum of anti-cholinergic effects and induction of seizures. Some side effects, such as hyperglycemia, could reflect direct actions on serotonin receptors, some of which astrocytes are known to possess.

The concentrations of clomipramine found effective in cultured astrocytes is 5-10 μM. The concentration of clomipramine in brain at least transiently reaches this range following IP injection. The plasma concentration of clomipramine (sometimes considered in combination with the active metabolite, desmethyl-clomipramine) that is considered therapeutic in humans is in the range of 0.3-1.75 µM, which is close to the levels necessary for suppression of the GFAP promoter in mice.

If GFAP is similar to other intermediate filament proteins in being long-lived, lengthy periods of time may have to elapse before significant reductions in protein take place, even in the face of substantial reductions in synthetic rate. The actual turnover rate of GFAP has been documented only three times, with inconsistent results. Using primary cultures of rat astrocytes, Chiu and Goldman found biphasic kinetics of GFAP degradation, with half-times on the order of ~18 hours and 6 days, whereas others have found only monophasic kinetics, with a half-life of 7.5 days. Perhaps of significance for eventual therapeutic applications is that GFAP turnover may be considerably slower in vivo. This question has only been addressed once, in mouse spinal cord, where GFAP displayed a half-life of approximately 9 weeks.

In this light of the finding that only 3 weeks of treatment with clomipramine leads to a ~50% reduction in GFAP protein is surprising. The results suggest either that GFAP half-life in vivo is considerably shorter than previously observed in the one reported study, or that turnover varies by anatomic site. Alternatively, clomipramine may effect both synthesis and degradation so as to accelerate the drop in total protein levels.

EXPERIMENTAL EXAMPLES III

A number of betulinic acid derivatives were synthesized from betulinic acid using the synthetic routes illustrated in Scheme A.

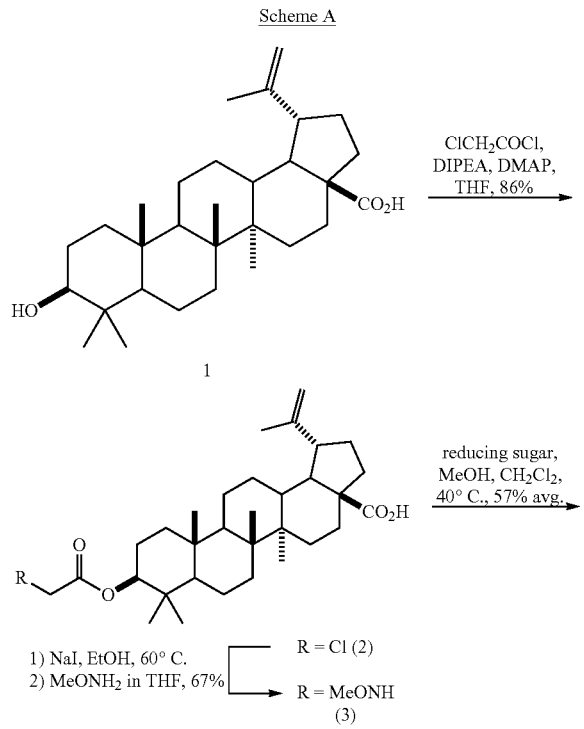

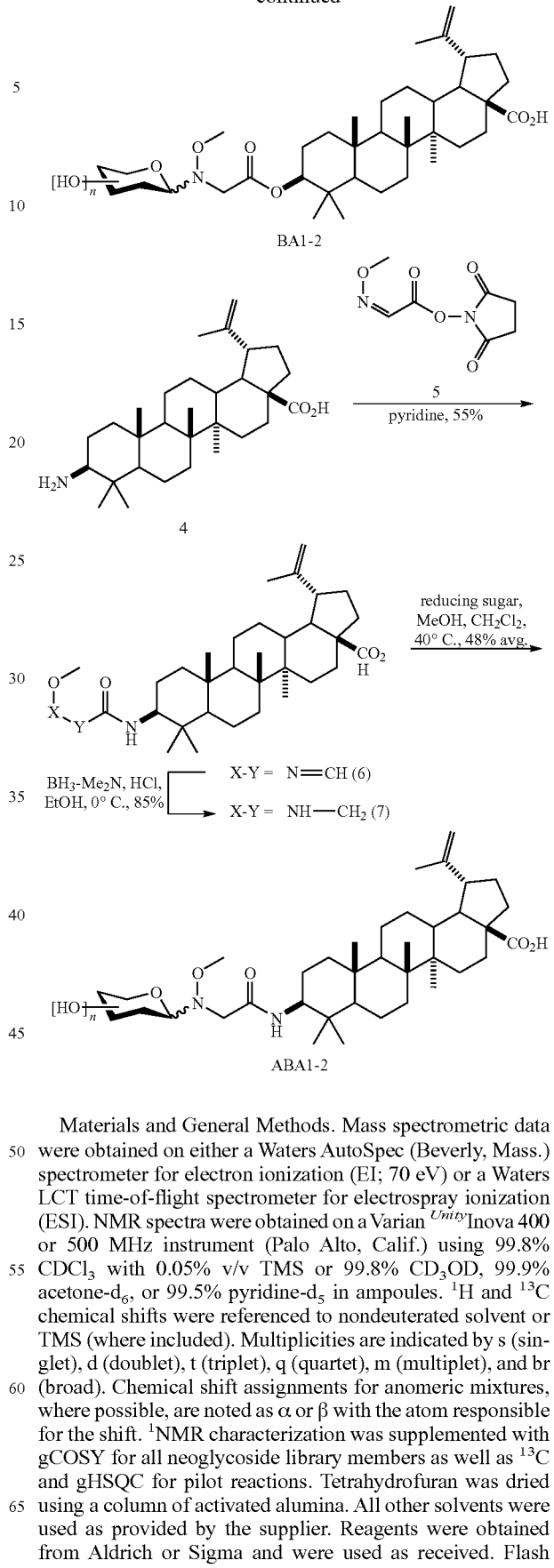

Materials and General Methods. Mass spectrometric data were obtained on either a Waters AutoSpec (Beverly, Mass.) spectrometer for electron ionization (EI; 70 eV) or a Waters LCT time-of-flight spectrometer for electrospray ionization (ESI). NMR spectra were obtained on a Varian $^{Unity}$Inova 400 or 500 MHz instrument (Palo Alto, Calif.) using 99.8% $CDCl_3$ with 0.05% v/v TMS or 99.8% $CD_3OD$, 99.9% acetone-$d_6$, or 99.5% pyridine-$d_5$ in ampoules. $^1H$ and $^{13}C$ chemical shifts were referenced to nondeuterated solvent or TMS (where included). Multiplicities are indicated by s (singlet), d (doublet), t (triplet), q (quartet), m (multiplet), and br (broad). Chemical shift assignments for anomeric mixtures, where possible, are noted as α or β with the atom responsible for the shift. $^1$NMR characterization was supplemented with gCOSY for all neoglycoside library members as well as $^{13}C$ and gHSQC for pilot reactions. Tetrahydrofuran was dried using a column of activated alumina. All other solvents were used as provided by the supplier. Reagents were obtained from Aldrich or Sigma and were used as received. Flash chromatography was performed using 40-63 μm particle sized silica gel. Thin layer chromatography was performed on aluminum-backed, 254 nm UV-active plates with a silica gel particle size of 60 μm.

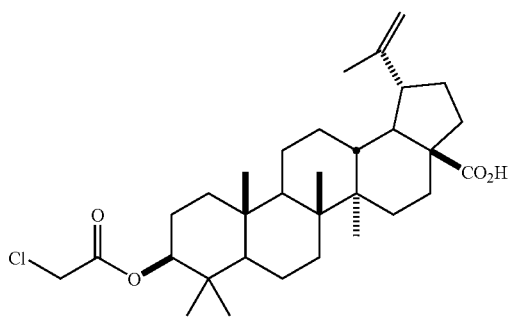

(3S)—O-Chloroacetylbetulinic acid (2). Betulinic acid (1, 335 mg, 0.734 mmol) and DMAP (9 mg, 0.07 mmol) were dissolved in anhydrous THF (20 mL) under Ar. Diisopropylethylamine (190 μL, 1.09 mmol) was added followed by dropwise addition of chloroacetyl chloride (120 μL, 1.51 mmol), soon after which the reaction became cloudy. After stirring for 2 h, absolute ethanol (500 μL) was used to quench the reaction. The solvent was removed in vacuo and the resulting crude solid was adsorbed onto silica gel, after dissolving in $CH_2Cl_2$ (5 mL), then purified by column chromatography ($SiO_2$, EtOAc:Hex 1:5) to give the desired chloroacetate as a white solid (338 mg, 86%, $R_f$=0.57 EtOAc:Hex 1:4). $^1$NMR ($CDCl_3$, 400 MHz) δ 4.74 (d, J=1.9 Hz, 1 H), 4.62 (t, J=1.3 Hz, 1 H), 4.57 (m, 1 H), 4.05 (d, J=2.4 Hz, 2 H), 3.01 (td, J=10.9, 4.7 Hz, 1 H), 2.28 (dt, J=12.5, 3.1, 1 H), 2.19 (td, J=12.6, 3.3 Hz, 1 H), 2.03-1.94 (m, 2 H), 1.74-1.58 (m, 10 H), 1.55-1.47 (m, 3 H), 1.46-1.34 (m, 9 H), 1.33-1.25 (m, 2 H), 1.21-1.16 (m, 1 H), 0.98 (s, 3 H), 0.94 (s, 3 H), 0.87 (s, 3 h), 0.85 (s, 3 H), 0.82-0.78 (m, 1 H); $^{13}$C NMR ($CDCl_3$, 100 MHz) δ 182.10, 167.36, 150.56, 109.98, 83.58, 56.60, 55.59, 50.60, 49.50, 47.16, 42.66, 41.47, 40.92, 38.62, 38.53, 38.24, 37.33, 34.42, 32.36, 30.77, 29.90, 28.15, 27.14, 25.63, 21.08, 19.56, 18.33, 16.62, 16.39, 16.25, 14.89; HRMS (ESI) m/z for $C_{32}H_{49}ClNaO_4$ ([M+Na]$^+$) 555.3209, calc. 555.3217.

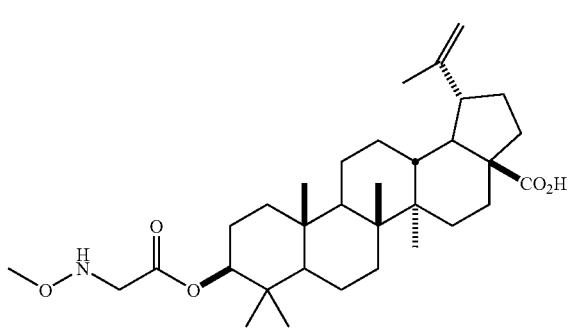

(3S)—O—(N-Methoxyglycyl)betulinic acid (3). Procedure A (<500 mg batches): Chloroacetate 2 (177 mg, 0.333 mmol) was dissolved in absolute ethanol (16 mL) along with NaI (160 mg, 1.07 mmol) under Ar. After stirring at room temperature for 40 min, a solution of $MeONH_2$ in THF (1.7 M, 2 mL, 3.4 mmol; made by mixing $MeONH_3Cl$ in a NaOH/ THF slurry for 16 h) was added, the inert gas line removed, and the reaction heated to 60° C. After 14 h, and again at 16 h, another equivalent of $MeONH_2$ reagent was added. At 19 h total, the solvent was removed in vacuo and the crude solid was purified by column chromatography ($SiO_2$, EtOAc:Hex 1:3) to give the desired aglycon as a white sticky solid (120 mg, 67%, $R_f$=0.26 EtOAc:Hex 1:3). Procedure B (≧500 mg batches): Chloroacetate 2 (1.20 g, 2.25 mmol) was dissolved in absolute ethanol (100 mL) along with NaI (1.01 g, 6.75 mmol) under Ar. After stirring at room temperature for 2 h, a solution of $MeONH_2$ in THF (2.4 M, 1.9 mL, 4.56 mmol) was added, the inert gas line removed, and the reaction heated to 60° C. Two hours after base addition, the reaction was cooled to room temperature and another aliquot of $MeONH_2$ in THF (2 eq.) was introduced followed by reheating to 60° C. This additive process was repeated roughly every 2 h until the reaction had progressed sufficiently (based upon TLC, EtOAc:Hex 1:3) which occurred after ~24 h of total reaction time. The solvent was removed and the product purified as described above (610 mg, 50%). $^1$H NMR ($CDCl_3$, 400 MHz) δ 4.71 (s, 1 H), 4.58 (s, 1 H), 4.55 (m, 1 H), 3.60 (d, J=4.4 Hz, 2 H), 3.51 (s, 3 H), 2.98 (td, J=10.5, 4.4 Hz, 1 H), 2.25 (d, J=2.7 Hz, 1 H), 2.16 (td, J=12.5, 3.2 Hz, 1 H), 2.00-1.89 (m, 2 H), 1.72-1.53 (m, 11 H), 1.52-1.45 (m, 2 H), 1.44-1.32 (m, 6 H), 1.25-1.21 (m, 1 H), 1.18-1.12 (m, 1 H), 1.04-0.99 (m, 1 H), 0.95 (s, 3 H), 0.91 (s, 3 H), 0.83 (s, 6 H), 0.81 (s, 3 H), 0.80-0.75 (m, 1 H); $^{13}$C NMR ($CDCl_3$, 100 MHz) δ 181.31, 170.97, 150.50, 109.78, 82.17, 61.52, 56.43, 55.47, 53.14, 50.48, 49.32, 46.99, 42.50, 40.78, 38.43, 37.96, 37.18, 37.14, 34.30, 32.26, 30.65, 29.78, 27.99, 25.52, 23.80, 20.95, 19.42, 18.23, 16.57, 16.25, 16.05, 14.74; HRMS (ESI) m/z for $C_{33}H_{53}NaNO_4$ ([M+Na]$^+$) 566.3820, calc. 566.3821.

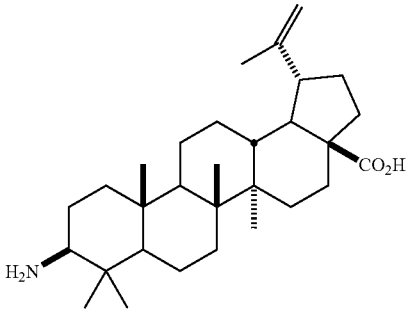

(3S)-Aminobetulinic acid (4). Betulonic acid (650 mg, 1.43 mmol) was dissolved in methanol (25 mL) with strong agitation. Ammonium acetate (1.11 g, 14.4 mmol) and NaC-NBH$_3$ (61 mg, 0.97 mmol) were then combined to the reaction vessel. After 8 h, the clear reaction solution turned to a cloudy mixture, which remained until 40 h when the reaction was quenched with conc. HCl to a pH of 2. The methanol was removed in vacuo and the aqueous remainder diluted with 25 mL of deionized water. The mixture was extracted with $Et_2O$ (20 mL), resulting in an emulsion that required separation by centrifugation (4000 rpm, 4 m). After removal of the organic layer, the process of $Et_2O$ extraction and centrifugation was repeated twice more. The pH of the combined aqueous layer and resulting solid mass was adjusted to 10 with KOH flakes, inducing the appearance of more white precipitate. Further centrifugation separated the desired product as a solid mass, which dried to a fluffy white powder (651 mg, >99%, $R_f$=0.26 EtOAc:Hex 2:1). $^1$H NMR (pyridine-d$_5$:acetone-d$_6$ 9:1, 400 MHz) δ 4.96 (d, J=1.9 Hz, 1 H), 4.79 (q, J=2.2, 1.3 Hz, 1 H), 3.54-3.48 (m, 1 H), 3.04 (dd, J=11.7, 4.2 Hz, 1 H), 2.77-2.69 (m, 1 H), 2.64-2.58 (m, 1 H), 2.27-2.21 (m, 2 H), 2.02-1.93 (m, 2 H), 1.92-1.77 (m, 6 H), 1.74-1.68 (m, 1 H), 1.63-1.56 (m, 8 H), 1.32-1.19 (m, 3 H), 1.15 (s, 3 H), 1.13-1.05 (m, 8 H), 0.91 (s, 3 H), 0.90-0.87 (m, 1 H), 0.82 (s, 3 H); $^{13}$C NMR (pyridine-$d_5$:acetone-$d_6$ 9:1, 100 MHz) δ 179.04, 151.62, 110.07, 69.12, 56.85, 56.57, 51.31, 49.98, 47.97, 43.10, 41.37, 39.59, 38.82, 37.92, 37.79, 35.05, 33.09, 31.42, 30.50, 29.27, 26.36, 25.80, 21.39, 19.65, 18.90, 17.99, 16.80, 16.60, 15.10; HRMS (EI) m/z for $C_{30}H_{49}NO_4$ ([M]$^{+\cdot}$) 455.3750, calc. 455.3763. δ

5

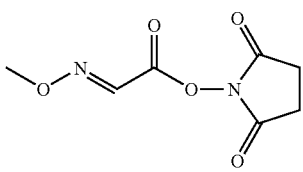

N'-Succinimidyl-N-methoxyiminoacetate (5). N-Methoxyiminoacetic acid (1.10 g, 10.7 mmol) was dissolved in 1:1 p-dioxane:$CH_2Cl_2$ (10 mL) followed by the addition of N-hydroxysuccinimide (1.35 g, 11.7 mmol). The reaction was cooled to 0° C. then 1,3-diisopropoylcarbodiimide (1.9 mL, 12.2 mmol) was added. After stirring for 30 min, the resulting suspension was cold-filtered and the solvent removed in vacuo. The white residue was dissolved in THF (5 mL) and passed through a silica gel plug with 1:1 EtOAc:Hex. The white solid (1.78 g, 83%, $R_f$=0.73 EtOAc:Hex 1:1) was used without further purification. $^1$H NMR (pyridine-$d_5$, 400 MHz) δ 7.95 (s, 1 H), 3.92 (s, 3 H), 2.88 (s, 4 H); $^{13}$C NMR (pyridine-$d_5$, 100 MHz) δ 170.32, 158.62, 138.00, 64.53, 26.53; HRMS (ESI) m/z for $C_7H_9N_2O_5$ ([M+H]$^+$) 201.0526, calc. 201.0506.

6

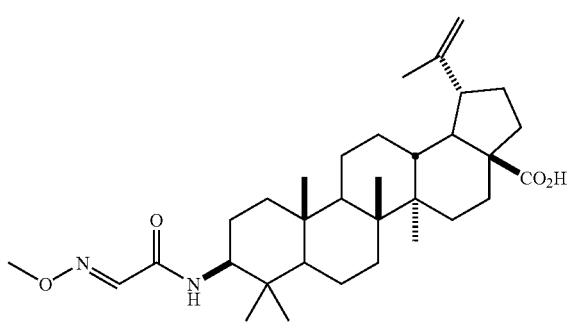

(3S)—N—(N'-Methoxyiminoacetyl)aminobetulinic acid (6). (3S)-Aminobetulinic acid (4; 208 mg, 0.456 mmol) was dissolved in pyridine (20 mL) followed by addition of activated ester 5 (107 mg, 0.535 mmol). After 1 h, the solvent was removed in vacuo and the crude material was dissolved in a minimal volume of MeOH:$CH_2Cl_2$ 1:1 and adsorbed onto silica gel. Subsequent flash chromatography ($SiO_2$, EtOAc: Hex 1:4) gave the desired purified product as a white amorphous solid (135 mg, 55%, $R_f$=0.27 EtOAc:Hex 1:4). $^1$H NMR (CDCl$_3$, 400 MHz) δ 7.41 (s, 1 H), 6.41 (d, J=10.3 Hz, 1 H), 4.75 (s, 1 H), 4.61 (s, 1 H), 3.96 (s, 3 H), 3.71 (td, J=11.0, 5.4 Hz, 1 H), 3.07-2.99 (m, 1 H), 2.32-2.18 (m, 2 H), 2.04-1.94 (m, 2 H), 1.76-1.66 (m, 5 H), 1.65-1.29 (m, 15 H), 1.22-1.16 (m, 1 H), 1.11-1.05 (m, 1 H), 0.98 (s, 3 H), 0.94 (s, 3 H), 0.88 (s, 3 H), 0.86-0.85 (m, 1 H), 0.83 (s, 3 h), 0.80 (s, 3 H); $^{13}$C NMR (CDCl$_3$, 100 MHz) δ 181.70, 171.37, 161.44, 150.66, 109.82, 63.11, 60.57, 56.69, 56.17, 50.59, 49.41, 47.12, 42.59, 40.80, 39.25, 38.52, 38.17, 37.23, 34.37, 32.38, 30.77, 29.85, 28.59, 25.60, 22.95, 20.96, 19.49, 18.68, 16.51, 16.24, 16.18, 14.78; HRMS (ESI) m/z for $C_{33}H_{52}N_2NaO_4$ ([M+Na]$^+$) 563.3809, calc. 563.3825. δ

7

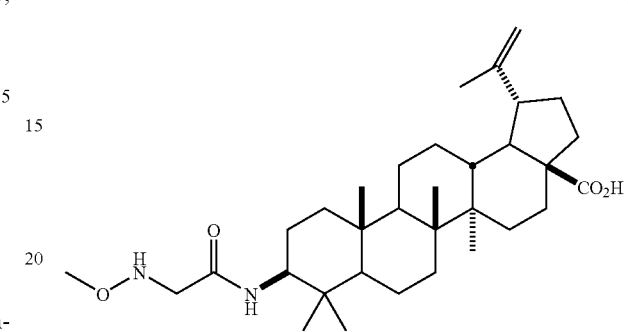

(3S)—N—(N'-Methoxyglycyl)aminobetulinic acid (7). Imine 6 (359 mg, 0.664 mmol) was dissolved in absolute ethanol (40 mL) and cooled to 0° C. $BH_3 \cdot Me_3N$ complex (484 mg, 6.63 mmol) was added in one aliquot and once fully dispersed, a 50% solution of HCl in absolute ethanol (1.11 mL, 6.71 mmol) was added, in dropwise fashion, over the course of five minutes. The reaction was allowed to warm to room temperature, dissolving the suspended material, and a second equal aliquot of ethanolic HCl was likewise added but at room temperature. After five hours, the reaction was quenched with saturated aqueous $NaHCO_3$ (20 mL) and extracted with $CH_2Cl_2$ (4×40 mL). The combined organic layers were washed with brine (20 mL) and dried over $Na_2SO_4$. Solvent removal yielded the aglycon as a flaky white solid (306 mg, 85%, $R_f$=0.43 MeOH:$CH_2Cl_2$ 5:95), which was used without further purification. $^1$H NMR (CDCl$_3$, 500 MHz) δ 6.70 (d, J=9.2 Hz, 1 H), 4.74 (s, 1 H), 4.60 (s, 1 H), 3.74-3.66 (m, 1 H), 3.56 (s, 5 H), 3.07-2.98 (m, 1 H), 2.32-2.19 (m, 2 H), 2.06-1.93 (m, 2 H), 1.76-1.65 (m, 5 H), 1.64-1.29 (m, 15 H), 1.20-1.14 (m, 1 H), 1.07-1.00 (m, 1 H), 0.97 (s, 3 H), 0.94 (s, 3 H), 0.88 (s, 3 H), 0.86 (br s, 1 H), 0.83 (s, 3 h), 0.79 (s, 3 H); $^{13}$C NMR (CDCl$_3$, 125 MHz) δ 180.98, 169.67, 150.59, 109.68, 61.99, 56.65, 56.50, 56.17, 55.11, 50.61, 49.40, 47.15, 42.61, 40.84, 39.30, 38.52, 37.93, 37.31, 37.29, 34.43, 32.46, 30.82, 29.90, 28.57, 25.68, 22.88, 21.03, 19.54, 18.75, 16.60, 16.31, 16.27, 14.86; HRMS (ESI) m/z for $C_{33}H_{55}N_2O_4$ ([M+H]$^+$) 543.4153, calc. 543.4156.

General procedure for neoglycoside library synthesis and purification. Aglycons 3 or 7 (typically 0.053-0.064 mmol) were added to 1 dram vials along with stir fleas and dissolved in $CH_2Cl_2$ (100 μL). The volumes were adjusted with MeOH (~600 μL) to provide the aglycon at a concentration of 90-100 mM. Reducing sugars (3 eq.) were added, the vials capped, and the vessels placed on a heating block/stir plate to react for 48 h at 40° C. The vial caps were removed and the solvent evaporated by a Speedvac apparatus (55° C., 3 h). Crude neoglycosides were suspended in 5:95 methanol:$CH_2Cl_2$ (250 μL) with sonication (5 min) and then purified via 2000 mg silica gel solid phase extraction (SPE) columns (Alltech, Deerfield, Ill.) prewashed with 5% methanol in chloroform. The SPEs were eluted using a vacuum manifold, collecting fractions with a volume of approximately 1.5 mL. After the initial two fractions were obtained, eluting any unreacted aglycon, the isocratic separation was continued for pentoses and substituted hexoses while a step gradient of 15% methanol in chloroform was used for hexoses or 20% methanol for glycuronosides. Typically, all neoglycoside was eluted by the seventh or eighth fraction leaving unreacted sugar on the SPE column. The fractions containing pure product were identified by TLC using p-anisaldehyde stain, then combined and dried. Compounds were assayed by $^1$H and gCOSY NMR as well as high-resolution electrospray ionization mass spectrometry. Anomeric ratios were obtained by comparison of anomeric proton integration.

BA1

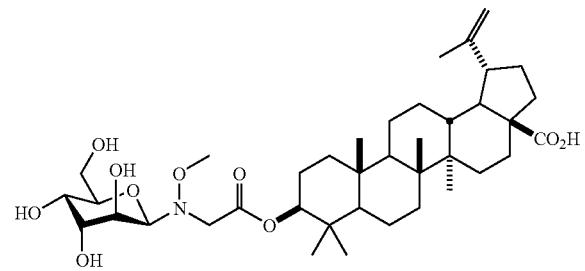

(3S)—O—(N-Methoxy-N-β-D-altrosylglycyl)betulinic acid (BA1). Using aglycon 3 (30 mg, 0.055 mmol), the product was yielded as a white solid (18 mg, 45%, $R_f$=0.36 MeOH:CH$_2$Cl$_2$ 10:90). $^1$H NMR (CD$_3$OD:acetone-d$_6$ 3:1, 500 MHz) δ 4.74 (d, J=1.7 Hz, 1 H), 4.63 (s br, 1 H), 4.57 (d, J=4.4 Hz, 0.6 H, β-H1), 4.55 (d, J=4.4 Hz, 1 H), 4.20-4.16 (m, 1.4 H, α-H1), 3.92-3.89 (m, 1.4 H, α), 3.83-3.75 (m, 1.6 H, β), 3.74-3.69 (m, 2 H, α+β), 3.68 (s, 3 H), 3.66 (s, 2 H), 3.63-3.58 (m, 1 H, 3.07, α+β), 3.06 (td, J=10.7, 4.7 Hz, 1 H), 2.35 (td, J=12.7, 3.5 Hz, 1 H), 2.27 (dt, J=12.7, 3.1 Hz, 1 H), 2.00-1.91 (m, 2 H), 1.80-1.63 (m, 8 H), 1.62-1.54 (m, 2 H), 1.52-1.38 (m, 8 H), 1.33-1.28 (m, 1 H), 1.24-1.19 (m, 1 H), 1.16-1.09 (m, 1 H), 1.06 (s, 3 H), 1.01 (s, 3 H), 0.94 (s, 3 H), 0.91 (s, 6 H), 0.88 (s br, 1 H); HRMS (ESI) m/z for C$_{39}$H$_{63}$NNaO$_{10}$ ([M+Na]$^+$) 728.4323, calc. 728.4344.

BA2

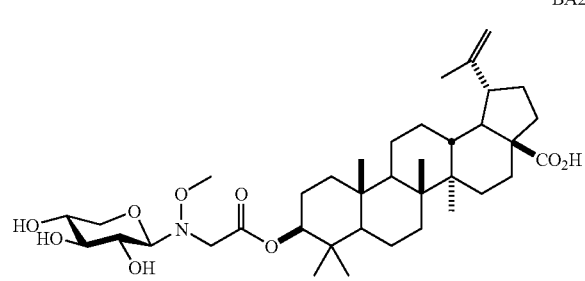

(3S)—O—(N-Methoxy-N-β-D-xylosylglycyl)betulinic acid (BA2). Using aglycon 3 (29 mg, 0.053 mmol), the product was yielded as a white solid (25 mg, 69%, $R_f$=0.23 MeOH:CH$_2$Cl$_2$ 5:95). $^1$H NMR (CD$_3$OD, 500 MHz) δ 4.74 (s br, 1 H), 4.62 (s br, 1 H), 4.60-4.58 (m, 1 H), 4.11 (d, J=8.3 Hz, 1 H), 3.91 (dd, J=11.2, 5.4 Hz, 1 H), 3.78-3.76 (m, 1 H), 3.66 (s, 2 H), 3.64 (s, 3 H), 3.52-3.45 (m, 1 H), 3.38-3.36 (m, 1 H), 3.18 (t, J=11.0 Hz, 1 H), 3.05 (td, J=10.8, 4.6 Hz, 1 H), 2.33 (td, J=12.7, 3.2 Hz, 1 H), 2.27 (dt, J=12.7, 2.9 Hz, 1 H), 1.99-1.90 (m, 2 H), 1.80-1.61 (m, 10 H), 1.61-1.53 (m, 2 H), 1.52-1.37 (m, 7 H), 1.33-1.28 (m, 1 H), 1.24-1.17 (m, 1 H), 1.10 (dd, J=13.3, 4.2 Hz, 1 H), 1.05 (s, 3 H), 1.00 (s, 3 H), 0.92 (s, 3 H), 0.90 (s, 6 H), 0.88-0.85 (m, 1 H); HRMS (ESI) m/z for C$_{39}$H$_{61}$NNaO$_9$ ([M+Na]$^+$) 698.4239, calc. 698.4257.

ABA1

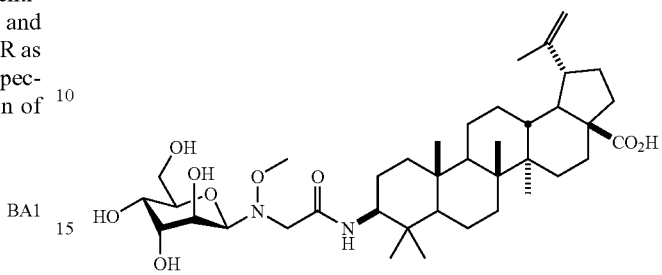

(3S)—N—(N'-Methoxy-N'-β-D-altrosylglycyl)betulinic acid (ABA1). Using aglycon 7 (47 mg, 0.087 mmol), the product was yielded as a white solid (12 mg, 20%, $R_f$=0.25 MeOH:CH$_2$Cl$_2$ 10:90). $^1$H NMR (CD$_3$OD:acetone-d$_6$ 3:1, 500 MHz) δ 4.74 (s br, 1 H), 4.63 (s br, 1 H), 4.55 (d, J=4.6 Hz, 1 H), 4.22 (t, J=5.9 Hz, 1 H), 4.17 (q, J=5.0 Hz, 1 H), 3.98-3.93 (m, 2 H), 3.87-3.78 (m, 1 H), 3.76-3.68 (m, 3 H), 3.66 (s, 3 H), 3.07 (td, J=10.7, 4.6 Hz, 1 H), 2.36 (td, J=12.7, 3.1 Hz, 1 H), 2.27 (dt, J=12.7, 3.2 Hz, 1 H), 1.98-1.91 (m, 2 H), 1.79-1.63 (m, 7 H), 1.62-1.40 (m, 12 H), 1.33-1.29 (m, 1 H), 1.24-1.21 (m, 1 H), 1.16-1.11 (m, 1 H), 1.07 (s, 3 H), 1.01 (s, 3 H), 0.95 (s br, 1 H), 0.92 (s, 6 H), 0.87 (s, 3 H); HRMS (ESI) m/z for C$_{39}$H$_{65}$N$_2$O$_9$ ([M+H]$^+$) 705.4686, calc. 705.4685.

ABA2

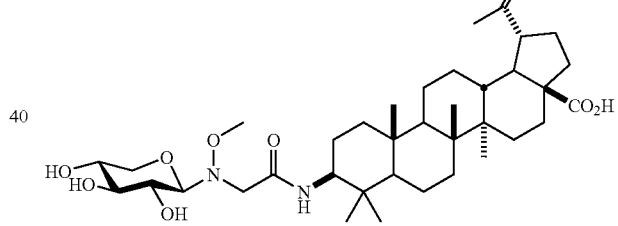

(3S)—N—(N'-Methoxy-N'-β-D-xylosylglycyl)betulinic acid (ABA2). Using aglycon 7 (48 mg, 0.088 mmol), the product was yielded as a white solid (45 mg, 75%, $R_f$=0.35 MeOH:CH$_2$Cl$_2$ 5:95). $^1$NMR (CD$_3$OD:acetone-d$_6$ 3:1, 500 MHz) δ 4.75 (s br, 1 H), 4.63 (s br, 1 H), 4.11 (d, J=8.7 Hz, 1 H), 3.90 (dd, J=11.1, 5.5 Hz, 1 H), 3.70-3.59 (m, 6 H), 3.51-3.46 (m, 1 H), 3.37 (t, J=8.9 Hz, 1 H), 3.20 (t, J=10.9 Hz, 1 H), 3.07 (td, J=10.7, 4.6 Hz, 1 H), 2.36 (td, J=12.7, 3.2 Hz, 1 H), 2.27 (dt, J=12.7, 3.1 Hz, 1 H), 2.00-1.90 (m, 2 H), 1.80-1.63 (m, 7 H), 1.62-1.38 (m, 12 H), 1.34-1.26 (m, 1 H), 1.25-1.22 (m, 1 H), 1.14-1.10 (m, 1 H), 1.07 (s, 3 H), 1.01 (s, 3 H), 0.95 (s, 1 H), 0.92 (s, 3 H), 0.90 (s, 3 H), 0.87 (s, 3 H); HRMS (ESI) m/z for C$_{38}$H$_{61}$N$_2$O$_8$ ([M-H]$^-$) 673.4435, calc. 673.4433.

ILLUSTRATIVE EMBODIMENTS

One illustrative embodiment includes a method of treating Alexander disease, the method comprising administering to a subject at risk of or with Alexander disease a therapeutically effective amount of a compound capable of downregulating the expression of a glial fibrillary acidic protein (GFAP).

In some embodiments, the compounds may be approved for human use by the FDA. For example, in some embodiments, the compounds are antidepressants, antipsychotics, serotonin inhibitors or antihistamines. In other embodiments the compounds are tricyclic. In further embodiments, the compound is a tricyclic antidepressant. In still other embodiments, the compound is amitriptyline, butriptyline, amoxapine, clomipramine, desipramine, dosulepin hydrochloride, doxepin, imipramine, dibenzepin, iprindole, lofepramine, nortriptyline, opipramol, protriptyline, trimipramine or a combination thereof. In further embodiments, the compound is diaziquone, clomipramine, chrysophanol, amitriptyline, tamoxifen, amlodipine, embelin, thioridazine, ritanserin, ketotifen, kanamycin, 4-acetamidophenyl salicylate, terfenadine and combinations thereof.

In some embodiments, administering the compound decreases the intensity of megalencephaly that is associated with Alexander disease, decreases the amount of Rosenthal fibers, decreases the intensity or frequency of seizures or two or more of the above.

Another illustrative embodiment includes a method of decreasing the expression of a glial fibrillary acidic protein (GFAP) in a cell comprising administering to the cell a compound capable of downregulating the expression of a glial fibrillary acidic protein (GFAP).

In some embodiments, the compound is an antidepressant, an antipsychotic, a serotonin inhibitor or an antihistamine. In further embodiments, the compound is tricyclic. In still other embodiments, the compound is a tricyclic antidepressant, such as amitriptyline or clomipramine. In other embodiments, the compound may be butriptyline, amoxapine, desipramine, dosulepin hydrochloride, doxepin, imipramine, dibenzepin, iprindole, lofepramine, nortriptyline, opipramol, protriptyline, trimipramine or a combination thereof. In further embodiments, the compound is diaziquone, clomipramine, chrysophanol, amitriptyline, tamoxifen, amlodipine, embelin, thioridazine, ritanserin, ketotifen, kanamycin, 4-acetamidophenyl salicylate, terfenadine and combinations thereof.

In some embodiments, the expression of the glial fibrillary acidic protein (GFAP) decreases by at least 10% in comparison to the expression of the GFAP in a similar untreated cell.

In some embodiments, the cell is in a subject; in further embodiments, the subject is a human.

A further illustrative embodiment includes a method of decreasing the intensity of megalencephaly in a patient with Alexander disease, comprising administering to the patient a therapeutically effective amount of a compound that suppresses or prevents the formation of glial fibrillary acidic protein (GFAP).

Another illustrative embodiment includes a method of decreasing the amount of Rosenthal fibers in a patient with Alexander disease, comprising administering to the patient a therapeutically effective amount of a compound that suppresses or prevents the formation of glial fibrillary acidic protein (GFAP).

Yet another illustrative embodiment includes a method of decreasing the intensity or frequency of seizures in a patient with Alexander disease, comprising administering to the patient a therapeutically effective amount of a compound that suppresses or prevents the formation of glial fibrillary acidic protein (GFAP).

Another illustrative embodiment includes methods of decreasing glial fibrillary acidic protein (GFAP) in a cell, which include administering a therapeutically effective amount of GFAP lowering compound to the cell. In some embodiments, the cell is in a subject. In some embodiments, the subject is a human and the cell is a human cell.

Another illustrative embodiment includes methods to decrease the amount of GFAP in a human subject, which includes administering a therapeutically effective amount of a GFAP lowering compound to the human subject. In some embodiments, a GFAP lowering compound is administered to a subject who has been diagnosed with gliosis, and/or who is at risk or who has been diagnosed with Alexander disease. In some embodiments, administration of a GFAP lowering compound to a subject decreases one or more symptoms, such as the intensity of megalencelphaly associated with Alexander disease, the amount of Rosenthal fibers, the frequency of seizures, and the intensity of seizures.

In another illustrative embodiment, suitable examples of GFAP lowering compounds include c-pendant amino tricyclic compounds, quinine compounds, triterpene derivatives and polyphenol compounds.

As used herein, c-pendant amino tricyclic compounds are compounds (a) having a core structure composed of three and only three contiguous ring structures and (b) a pendant aminoalkylene or aminoalkenylene group (optionally having one or more chain carbons substituted by —O— or —S—) connected to the central ring of the tricyclic core. Non-limiting examples of such compounds include amitriptyline, clomipramine, chlorprothixene, fluphenazine, ketotifen, thioridazine.

In another illustrative embodiment, suitable quinone compounds include, without limitation, chrysophanol, diaziquone and embelin.

In still other illustrative embodiments, GFAP lowering compounds include triterpenoids. In some embodiments, the triterpenoid includes, without limitation, betulinic acid.

In other illustrative embodiments, suitable polyphenol compounds include, without limitation, EGCDG, irigenol, pyrogallin, chrysophanol, ritodrine, and methylnorlichexanthone.

In further illustrative embodiments, GFAP lowering compounds include steroid compounds. Exemplary steroid compounds include, without limitation, clobetasol, estradiol and fluccinonide.

In other illustrative embodiments, suitable examples of GFAP lowering compounds include antipsychotics, antidepressants, antihistamines and antineoplastic compounds.

In other illustrative embodiments, GFAP lowering compounds include antipsychotics such as, without limitation, ritanserin, chlorprothixene, thioridazine and fluphenazine.

In other illustrative embodiments, GFAP lowering compounds include tricyclic antipsychotics such as, without limitation, chlorprothixene, thioridazine and fluphenazine.

In further illustrative embodiments, GFAP lowering compounds include phenothiazine antipsychotics such as, without limitation, thioridazine and fluphenazine. In other embodiments, GFAP lowering compounds include other known phenothiazine antipsychotics such as, without limitation, chlorpromazine, promazine, levomepromazine, triflupromazine, mesoridazine, methotrimeprazine, perphenazine, prochlorperazine and trifluoperazine.

In other illustrative embodiments, GFAP lowering compounds include thioxanthene antipsychotics. In some embodiments, suitable thioxanthene antipsychotics include chlorprothixene, flupentixol, thiothixene, zuclopenthixol.

In another illustrative embodiment, exemplary suitable GFAP lowering compounds include antidepressants such as tricyclic antidepressants. Exemplary tricyclic antidepressants include, without limitation, amitriptyline, butriptyline, amoxapine, clomipramine, desipramine, dosulepin, doxepin, imipramine, dibenzepin, iprindole, lofepramine, nortriptyline, opipramol, protriptyline, and trimipramine.

In further illustrative embodiments, GFAP lowering compounds include antihistamines. Exemplary suitable antihistamines include, without limitation, ketotifen and terfenadine.

In other illustrative embodiments, GFAP lowering compounds include antineoplastic compounds. Exemplary suitable antineoplastic compounds include, without limitation, diaziquone and tamoxifen.

In other illustrative embodiments, the GFAP lowering compound exhibits an hGFAP promoter luciferase reduction activity of at least about 10%. In other embodiments the GFAP lowering compound exhibits an hGFAP promoter luciferase reduction activity of at least about 20%, at least about 30%, at least about 35%, at least about 40%, at least about 50% or at least about 60%. In some embodiments the GFAP lowering compound exhibits an hGFAP promoter luciferase reduction activity of at least about 70%, or at least about 80%.

In other illustrative embodiments, the GFAP lowering compound exhibits a cell-based GFAP protein level reduction of at least about 5%. In other embodiments, the GFAP lowering compound exhibits a cell-based GFAP protein level reduction of at least about 8%, at least about 9%, at least about 10%, at least about 11%, at least about 12%, at least about 15%, at least about 18%, at least about 20%, or at least about 21%.

In other illustrative embodiments, the GFAP lowering compound exhibits a MTDcc of at least about 10 µM. In other embodiments, the GFAP lowering compound exhibits a MTDcc of at least about 7 µM, at least about 5 µM, or at least about 2.5 µM. In further embodiments, the GFAP lowering compound exhibits a MTDcc of at least about 15 µM or at least about 20 µM.

In other illustrative embodiments, the GFAP lowering compound exhibits a desired hGFAP promoter luciferase reduction activity in conjunction with a desired cell-based GFAP protein level reduction and/or a desired MTDcc. For example, in some embodiments, the GFAP lowering compound has an MTDcc of greater than 15 µM and hGFAP promoter luciferase reduction activity of about 15%. In other embodiments, the GFAP lowering compound exhibits a cell-based GFAP protein level of greater than about 5% and a MTDcc of at least about 10 µM.

In other illustrative embodiments, the GFAP lowering compound includes one or more of diaziquone, clomipramine, chrysophanol, amitriptyline, chlorprothixene, EGCDG, tamoxifen, mundoserone, amlodipine, embelin, thioridazine, ritanserin, irigenol, fluccinonide, hexetidine, estradiol benzoate, ketotifen, clobetasol propionate, colecalciferol, fluphenazine, pyrogallin and kanamycin.

In other illustrative embodiments, the GFAP lowering compound includes one or more of diaziquone, clomipramine, chrysophanol, amitriptyline, tamoxifen, amlodipine, embelin, thioridazine, ritanserin, ketotifen, kanamycin, 4-acetamidophenyl salicylate, and terfenadine.

In further illustrative embodiments, the GFAP lowering compound includes one or more of diaziquone, clomipramine, chrysophanol, amitriptyline, chlorprothixene, EGCDG, mundoserone, amlodipine, ritanserin, irigenol, fluccinonide, hexetidine, estradiol benzoate, ketotifin, clobetasol propionate, colecalciferol, pyrogallin, kanamycin, azinphos methyl, 4-acetamidophenyl salicylate, oxotremorine, ritodrine, NPPB, chloramphenicol, phosphocreatine, betulinic acid, methylnorlichexanthone, and coumophos.

In further illustrative embodiments, the GFAP lowering compound includes one or more of diaziquone, clomipramine, chrysophanol, amitriptyline, chlorprothixene, EGCDG, tamoxifen, mundoserone, amlodipine, embelin and thioridazine.

In other illustrative embodiments, the GFAP lowering compound includes one or more of diaziquone, clomipramine, chrysophanol, amitriptyline, tamoxifen, amlodipine, embelin, thioridazine, ritanserin, ketotifen, kanamycin, 4-acetamidophenyl salicylate, terfenadine, hexetidine, ritodrine and betulinic acid.

In further illustrative embodiments, the GFAP lowering compound includes one or more of diaziquone, clomipramine, chrysophanol, amitriptyline, chlorprothixene, EGCDG, mundoserone, amlodipine, ritanserin, irigenol, fluccinonide, hexetidine, estradiol benzoate, ketotifin, clobetasol propionate, colecalciferol, pyrogallin, kanamycin, azinphos methyl, 4-acetamidophenyl salicylate, oxotremorine, ritodrine, NPPB and chloramphenicol.

The GFAP lowering compound may include betulinic acid or a derivative thereof. Examples of suitable betulinic acid derivatives include 3-aminobetulinic acid; derivatives of 3-O-(glycyl)-betulinic acid; and derivatives of N-(glycyl)-3-aminobetulinic acid. Suitable examples of such compounds include 3-O—(N-glycosyl-N-methoxyglycyl)esters of betulinic acid and/or N—(N-glycosyl-N-methoxyglycyl) amides of 3-aminobetulinic acid, e.g., where the glycosyl group may be based on a monosaccharide (e.g., a pentosyl or hexosyl group) and/or a disaccharide. Other suitable betulinic acid derivatives include 3-O—(N-methoxyglycyl)betulinic acid (also referred to herein as "betulinic acid aglycone ester" or the "aglycone ester"); and N—(N-methoxyglycyl)-3-aminobetulinic acid (also referred to herein as "3-aminobetulinic acid aglycone amide" or the "aglycone amide").

Specific examples of suitable betulinic acid 3-O-ester glycoside derivatives include 3-O—(N-glycosyl-N-methoxyglycyl)betulinic acid compounds such as:
  3-O—(N-xylosyl-N-methoxyglycyl)betulinic acid (also referred to herein as a "betulinic acid ester D-xyloside" or "D-xyloside (ester)"); and
  3-O—(N-altrosyl-N-methoxyglycyl)betulinic acid (also referred to herein as a "betulinic acid ester D-altroside" or "D-altroside (ester)").

Specific examples of suitable 3-aminobetulinic acid amide glycosides include (N-glycosyl-N-methoxyglycyl)betulinic acid compounds such as:
  3-O—(N-xylosyl-N-methoxyglycyl)-3-aminobetulinic acid (also referred to herein as "betulinic amide D-xyloside" or "D-xyloside (amide)"); and
  3-O—(N-altrosyl-N-methoxyglycyl)-3-aminobetulinic acid (also referred to herein as "betulinic amide D-altroside" or "D-altroside (amide)").

In other illustrative embodiments, the intensity of megalencephaly in a patient with Alexander disease is decreased. The embodiment includes administering to the patient a therapeutically effective amount of a GFAP lowering compound.

In a further illustrative embodiments, the amount of Rosenthal fibers in a patient with Alexander disease is decreased. The embodiments include administering to the patient a therapeutically effective amount of a compound that suppresses or prevents the formation of glial fibrillary acidic protein (GFAP).

It is to be understood that the various embodiments disclosed herein are not limited to the particular devices, methodology, protocols, subjects, or reagents described, and as such may vary. It is also to be understood that the terminology used herein is for the purpose of describing particular embodiments, and is not intended to be limiting. Other suitable modifications and adaptations of a variety of conditions and parameters, obvious to those skilled in the art of molecular biology, molecular interactions, chemistry, biology, medicine, and medical diagnostics, are within the scope of the compositions and methods described herein. All publications, patents, and patent applications cited herein are incorporated by reference in their entirety for all purposes.

What is claimed is:

1. A method of treating Alexander disease in a subject in need thereof comprising:
   administering to a subject at risk of or diagnosed with Alexander disease a therapeutically effective amount of a glial fibrillary acidic protein (GFAP) lowering compound, wherein the GFAP lowering compound comprises a polyphenol compound selected from the group consisting of epigallocatechin 3,5-digallate EGCDG embelin, irigenol, pyrogallin, chrysophanol, ritodrine, methylnorlichexanthone and combinations thereof; and the effective amount is sufficient to reduce GFAP levels in the subject.

2. The method of claim 1, wherein the polyphenol compound is EGCDG.

3. The method of claim 1, wherein the polyphenol compound comprises EGCDG.

4. The method of claim 1, wherein the polyphenol compound comprises irigenol.

5. The method of claim 1, wherein the polyphenol compound comprises chrysophanol.

6. The method of claim 1, wherein the GFAP lowering compound further comprises a compound selected from the group consisting of chlorprothixene, mundoserone, tamoxifen citrate, amlodipine, thioridazine, ritanserin, fluccinonide, hexetidine, estradiol benzoate, ketotifen, clobetasol propionate, colecalciferol, fluphenazine, kanmycin, azinphos methyl, 4-acetamidophenyl salicylate, oxotremorine, 5-nitro-2-phenylpropyl-aminobenzoic acid (NPPB), chloramphenicol, terfenadine, phosphocreatine, betulinic acid, betulinic acid derivatives, coumophos, swietenolide-3-acetate, decarbazine, veratic acid, pantothenic acid, neamine, amylodipine besylate, 7-desacetoxy-6,7-dehydrogedunin and combinations thereof.

7. The method of claim 1, wherein the GFAP lowering compound further comprises a compound selected from the group consisting of mundoserone, amlodipine besylate, 7-desacetoxy-6,7-dehydrogedunin and combinations thereof.

8. A method of treating Alexander disease in a subject in need thereof comprising:
   administering to a subject at risk of or diagnosed with Alexander disease a therapeutically effective amount of a glial fibrillary acidic protein (GFAP) lowering compound, wherein the GFAP lowering compound comprises betulinic acid and/or a betulinic acid derivative; and the effective amount is sufficient to reduce GFAP levels in the subject;
   wherein the betulinic acid derivative is selected from the group consisting of 3-O—(N-xylosyl-N-methoxyglycyl)betulinic acid, 3-O—(N-altrosyl-N-methoxyglycyl) betulinic acid, 3-O—(N-xvlosyl-N-methoxyglycyl)-3-aminobetulinic acid, 3-O—(N-altrosyl-N-methoxyglycgl)-3-aminobetulinic acid, and 3-aminobetulinic acid.

9. The method of claim 8, wherein the GFAP lowering compound further comprises a compound selected from the group consisting of chrysophanol, chlorprothixene, EGCDG, mundoserone, tamoxifen citrate, amlodipine, embelin, thioridazine, ritanserin, irigenol, fluccinonide, hexetidine, estradiol benzoate, ketotifen, clobetasol propionate, colecalciferol, fluphenazine, pyrogallin, kanmycin, azinphos methyl, 4-acetamidophenyl salicylate, oxotremorine, ritodrine, 5-nitro-2-phenylpropyl-aminobenzoic acid (NPPB), chloramphenicol, terfenadine, phosphocreatine, methylnorlichexanthone, coumophos, swietenolide-3-acetate, decarbazine, veratic acid, pantothenic acid, neamine, amylodipine besylate, 7-desacetoxy-6,7-dehydrogedunin and combinations thereof.

10. The method of claim 8, wherein the GFAP lowering compound further comprises a compound selected from the group consisting of EGCDG, mundoserone, irigenol, amlodipine besylate, 7-desacetoxy-6, 7-dehydrogedunin and combinations thereof.

11. The method of claim 8, wherein the GFAP lowering compound further comprises a polyphenol compound selected from the group consisting of EGCDG, embelin, irigenol, pyrogallin, chrysophanol, ritodrine, methylnorlichexanthone and combinations thereof.

12. The method of claim 8, wherein the GFAP lowering compound further comprises a quinone compound selected from the group consisting of chrysophanol, embelin and combinations thereof.

13. A method of treating Alexander disease in a subject in need thereof comprising:
   administering to a subject at risk of or diagnosed with Alexander disease a therapeutically effective amount of a glial fibrillary acidic protein (GFAP) lowering compound, wherein the GFAP lowering compound comprises mundoserone; and the effective amount is sufficient to reduce GFAP levels in the subject.

14. The method of claim 13, wherein the GFAP lowering compound further comprises a compound selected from the group consisting of chrysophanol, chlorprothixene, EGCDG, tamoxifen citrate, amlodipine, embelin, thioridazine, ritanserin, irigenol, fluccinonide, hexetidine, estradiol benzoate, ketotifen, clobetasol propionate, colecalciferol, fluphenazine, pyrogallin, kanmycin, azinphos methyl, 4-acetamidophenyl salicylate, oxotremorine, ritodrine, 5-nitro-2-phenylpropyl-aminobenzoic acid (NPPB), chloramphenicol, terfenadine, phosphocreatine, betulinic acid, betulinic acid derivatives, methylnorlichexanthone, coumophos, swietenolide-3-acetate, decarbazine, veratic acid, pantothenic acid, neamine, amylodipine besylate, 7-desacetoxy-6,7-dehydrogedunin and combinations thereof.

15. The method of claim 13, wherein the GFAP lowering compound further comprises a compound selected from the group consisting of EGCDG, irigenol, amlodipine besylate, 7-desacetoxy-6,7-dehydrogedunin and combinations thereof.

16. The method of claim 13, wherein the GFAP lowering compound further comprises a c-pendant amino tricyclic compound selected from the group consisting of chlorprothixene, fluphenazine, ketotifen, thioridazine and combinations thereof.

17. The method of claim 13, wherein the GFAP lowering compound further comprises a polyphenol compound selected from the group consisting of EGCDG, embelin, irigenol, pyrogallin, chrysophanol, ritodrine, methylnorlichexanthone and combinations thereof.

* * * * *